(12) United States Patent
Hansen et al.

(10) Patent No.: US 12,371,722 B2
(45) Date of Patent: Jul. 29, 2025

(54) RECOMBINANT HOST CELLS WITH IMPROVED PRODUCTION OF L-DOPA, DOPAMINE, S-NOROCLAURINE OR DERIVATIVES THEREOF

(71) Applicant: RIVER STONE BIOTECH APS, Copenhagen (DK)

(72) Inventors: Esben Halkjaer Hansen, Copenhagen (DK); Jens Houghton-Larsen, Copenhagen (DK)

(73) Assignee: RIVER STONE BIOTECH APS, Copenhagen (DK)

( * ) Notice: Subject to any disclaimer, the term of this patent is extended or adjusted under 35 U.S.C. 154(b) by 875 days.

(21) Appl. No.: 17/421,967

(22) PCT Filed: Jan. 10, 2020

(86) PCT No.: PCT/EP2020/050610
§ 371 (c)(1),
(2) Date: Jul. 9, 2021

(87) PCT Pub. No.: WO2020/144371
PCT Pub. Date: Jul. 16, 2020

(65) Prior Publication Data
US 2022/0112528 A1    Apr. 14, 2022

(30) Foreign Application Priority Data
Jan. 11, 2019 (DK) .............................. PA201900035

(51) Int. Cl.
*C12N 9/02* (2006.01)
*C12N 15/81* (2006.01)
*C12P 13/00* (2006.01)
*C12R 1/865* (2006.01)

(52) U.S. Cl.
CPC .......... *C12P 13/001* (2013.01); *C12N 9/0071* (2013.01); *C12N 15/81* (2013.01); *C12R 2001/865* (2021.05); *C12Y 114/16002* (2013.01)

(58) Field of Classification Search
None
See application file for complete search history.

(56) References Cited

FOREIGN PATENT DOCUMENTS

| WO | WO 2015/066642 A1 | 5/2015 | |
|---|---|---|---|
| WO | WO 2016/049364 A2 | 3/2016 | |
| WO | WO 2017/122189 A1 | 7/2017 | |
| WO | WO-2018005553 A1 * | 1/2018 | ............. C12N 15/70 |
| WO | WO 2018/229305 A1 | 12/2018 | |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Polturak et al., "Elucidation of the first committed step in betalain biosynthesis enables the heterologous engineering of betalain pigments in plants", New Phytologist, vol. 210(1):269-283 (Dec. 2015).
Trenchard et al., "De novo production of the key branch point benzylisoquinoline alkaloid reticuline in yeast", Metabolic Engineering, vol. 31:74-83 (Sep. 2015).
Galanie et al., "Complete biosynthesis of opioids in yeast", Science, vol. 349(6252):1095-1100 (Sep. 2015).
Diamond et al., "Metabolic engineering for the production of plant isoquinoline alkaloids", Plant Biotechnology Journal, vol. 14(6):1319-1328 (Oct. 2015).

* cited by examiner

*Primary Examiner* — Richard G Hutson
(74) *Attorney, Agent, or Firm* — McDonnell Boehnen Hulbert & Berghoff LLP

(57) ABSTRACT

The present invention relates to a recombinant microbial host cell comprising an operative biosynthetic metabolic pathway capable of producing one or more compounds selected from the group consisting of L-dopa, dopamine, (S)-Norcoclaurine and derivatives thereof; said pathway comprising a heterologous L-tyrosine hydroxylase (TyrH) converting L-Tyrosine into L-dopa capable of increasing the cell production of the Compound compared to a reference L-tyrosine hydroxylase having the sequence set forth in SEQ ID NO: 58.

17 Claims, 3 Drawing Sheets
Specification includes a Sequence Listing.

```
                         SEQUENCE LISTING

<160> NUMBER OF SEQ ID NOS: 80

<210> SEQ ID NO 1
<211> LENGTH: 1500
<212> TYPE: DNA
<213> ORGANISM: Spinacia oleracea

<400> SEQUENCE: 1
atggaaaaca ccaccttggc cttgattttg ccaattttgt tcatctgctt ccacctgatc      60
cattccttca tttgccaatc cagaaagtcc tctaaattgc caccaggtcc aaaaagaatg     120
ccaatctttg gtaacatctt cgacttgggt gaaaagccac atagatcttt tgctaacttg     180
gctaagattc acggtccatt ggtttctttg aagttgggtt ctatcactac catcgttgtt     240
tcatcagctg aagttgccaa agaaatgttc ttgaagaacg accagttgtt gtccaacaga     300
actattccag attctgttag agctggtgat cacgataagt tgtctatgtc ttggttgcca     360
gtttctgcta aatggcgtaa cttgagaaag atttctgctg tgcagctgtt gtctaatcaa     420
agattagatg cttcccaagc tcaaagacaa gctaaagtca aacagttgtt ggcttacgtt     480
caagactgtt ctaaaaaggg tcaaccagtt gatattggta gagctgcttt tactacctcc     540
ttgaacttgt tgtcaaacac cttcttctct gttgaattgg cctctcatga atcctctgtt     600
tctcaagaat tcaagcagtt gatgtggaac atgatggaag aaattggtag accaaactac     660
gctgattact cccaattttt gggttacgtt gatcctttcg gtatcagaag aagattggct     720
gcttactttg accaattgat cgttgtgttc aagacatca tcagagaaag acaaaaagtc     780
aggtctacga atggttctaa cgctaagcaa actaacgata tcttggacac cttgttgaac     840
ttgcatggtg aaaacgaatt gtccatgggt gaaatcaatc atttgttggc cgatattttc     900
aacgctggta ctgatacaac tgcttctact ttggaatggg ctatgactga attggttaag     960
aacccaaata tgatgggtag agtccagaac gaaattgaac aagctttggg tagagattgc    1020
tcctccattc aagaatctga catcttgaaa ttgccatact gcaggccat tatcaaagag    1080 actttgagat tgcatccacc aaccgttttt tgttgccaa gaaaagctga tactgacgtc    1140
gaattgaacg ttatttggt tccaaagaac gcccaagttt tggttaattt gtgggctata    1200
ggtagagatc caaggtttg ggaaaatcca gaagttttct tgccagaacg tttcttgaac    1260
tccgaaattg atgttaaggg cagagatttt gagttgttgc catttggtgc tggtagaaga    1320
```

-continued

```
atttgtccag gtttgacatt ggcttacagg atgttgaatt tgatgttggc taccttggtt   1380
aacaactacg attggaaatt ggaggatggt atgaacccag aaaatttgga tatggacgaa   1440
aagttcggta ttaccttgca aaaggttaac ccattgagag ccattccaat tccaagatga   1500
```

<210> SEQ ID NO 2
<211> LENGTH: 499
<212> TYPE: PRT
<213> ORGANISM: Spinacia oleracea

<400> SEQUENCE: 2

| | | | | | | | | | | | | | | |
|---|---|---|---|---|---|---|---|---|---|---|---|---|---|---|
| Met | Glu | Asn | Thr | Thr | Leu | Ala | Leu | Ile | Leu | Pro | Ile | Leu | Phe | Ile | Cys |
| 1 | | | | 5 | | | | | 10 | | | | | 15 | |
| Phe | His | Leu | Ile | His | Ser | Phe | Ile | Cys | Gln | Ser | Arg | Lys | Ser | Ser | Lys |
| | | | 20 | | | | | 25 | | | | | 30 | | |
| Leu | Pro | Pro | Gly | Pro | Lys | Arg | Met | Pro | Ile | Phe | Gly | Asn | Ile | Phe | Asp |
| | | 35 | | | | | 40 | | | | | 45 | | | |
| Leu | Gly | Glu | Lys | Pro | His | Arg | Ser | Phe | Ala | Asn | Leu | Ala | Lys | Ile | His |
| | 50 | | | | | 55 | | | | | 60 | | | | |
| Gly | Pro | Leu | Val | Ser | Leu | Lys | Leu | Gly | Ser | Ile | Thr | Thr | Ile | Val | Val |
| 65 | | | | | 70 | | | | | 75 | | | | | 80 |
| Ser | Ser | Ala | Glu | Val | Ala | Lys | Glu | Met | Phe | Leu | Lys | Asn | Asp | Gln | Leu |
| | | | | 85 | | | | | 90 | | | | | 95 | |
| Leu | Ser | Asn | Arg | Thr | Ile | Pro | Asp | Ser | Val | Arg | Ala | Gly | Asp | His | Asp |
| | | | 100 | | | | | 105 | | | | | 110 | | |
| Lys | Leu | Ser | Met | Ser | Trp | Leu | Pro | Val | Ser | Ala | Lys | Trp | Arg | Asn | Leu |
| | | | 115 | | | | | 120 | | | | | 125 | | |
| Arg | Lys | Ile | Ser | Ala | Val | Gln | Leu | Leu | Ser | Asn | Gln | Arg | Leu | Asp | Ala |
| | 130 | | | | | 135 | | | | | 140 | | | | |
| Ser | Gln | Ala | Gln | Arg | Gln | Ala | Lys | Val | Lys | Gln | Leu | Leu | Ala | Tyr | Val |
| 145 | | | | | 150 | | | | | 155 | | | | | 160 |
| Gln | Asp | Cys | Ser | Lys | Lys | Gly | Gln | Pro | Val | Asp | Ile | Gly | Arg | Ala | Ala |
| | | | | 165 | | | | | 170 | | | | | 175 | |
| Phe | Thr | Thr | Ser | Leu | Asn | Leu | Leu | Ser | Asn | Thr | Phe | Phe | Ser | Val | Glu |
| | | | 180 | | | | | 185 | | | | | 190 | | |
| Leu | Ala | Ser | His | Glu | Ser | Ser | Val | Ser | Gln | Glu | Phe | Lys | Gln | Leu | Met |
| | | | 195 | | | | | 200 | | | | | 205 | | |
| Trp | Asn | Met | Met | Glu | Glu | Ile | Gly | Arg | Pro | Asn | Tyr | Ala | Asp | Tyr | Phe |
| | 210 | | | | | 215 | | | | | 220 | | | | |
| Pro | Ile | Leu | Gly | Tyr | Val | Asp | Pro | Phe | Gly | Ile | Arg | Arg | Arg | Leu | Ala |
| 225 | | | | | 230 | | | | | 235 | | | | | 240 |
| Ala | Tyr | Phe | Asp | Gln | Leu | Ile | Val | Val | Phe | Gln | Asp | Ile | Ile | Arg | Glu |
| | | | | 245 | | | | | 250 | | | | | 255 | |
| Arg | Gln | Lys | Val | Arg | Ser | Thr | Asn | Gly | Ser | Asn | Ala | Lys | Gln | Thr | Asn |
| | | | 260 | | | | | 265 | | | | | 270 | | |
| Asp | Ile | Leu | Asp | Thr | Leu | Leu | Asn | Leu | His | Gly | Glu | Asn | Glu | Leu | Ser |
| | | | 275 | | | | | 280 | | | | | 285 | | |
| Met | Gly | Glu | Ile | Asn | His | Leu | Leu | Ala | Asp | Ile | Phe | Asn | Ala | Gly | Thr |
| | 290 | | | | | 295 | | | | | 300 | | | | |
| Asp | Thr | Thr | Ala | Ser | Thr | Leu | Glu | Trp | Ala | Met | Thr | Glu | Leu | Val | Lys |
| 305 | | | | | 310 | | | | | 315 | | | | | 320 |
| Asn | Pro | Asn | Met | Met | Gly | Arg | Val | Gln | Asn | Glu | Ile | Glu | Gln | Ala | Leu |
| | | | | 325 | | | | | 330 | | | | | 335 | |
| Gly | Arg | Asp | Cys | Ser | Ser | Ile | Gln | Glu | Ser | Asp | Ile | Leu | Lys | Leu | Pro |

```
              340              345              350
Tyr Leu Gln Ala Ile Ile Lys Glu Thr Leu Arg Leu His Pro Pro Thr
            355              360              365
Val Phe Leu Leu Pro Arg Lys Ala Asp Thr Asp Val Glu Leu Asn Gly
        370              375              380
Tyr Leu Val Pro Lys Asn Ala Gln Val Leu Val Asn Leu Trp Ala Ile
385              390              395              400
Gly Arg Asp Pro Lys Val Trp Glu Asn Pro Glu Val Phe Leu Pro Glu
                405              410              415
Arg Phe Leu Asn Ser Glu Ile Asp Val Lys Gly Arg Asp Phe Glu Leu
            420              425              430
Leu Pro Phe Gly Ala Gly Arg Arg Ile Cys Pro Gly Leu Thr Leu Ala
        435              440              445
Tyr Arg Met Leu Asn Leu Met Leu Ala Thr Leu Val Asn Asn Tyr Asp
    450              455              460
Trp Lys Leu Glu Asp Gly Met Asn Pro Glu Asn Leu Asp Met Asp Glu
465              470              475              480
Lys Phe Gly Ile Thr Leu Gln Lys Val Asn Pro Leu Arg Ala Ile Pro
                485              490              495
Ile Pro Arg

<210> SEQ ID NO 3
<211> LENGTH: 1485
<212> TYPE: DNA
<213> ORGANISM: Opuntia ficus-indica

<400> SEQUENCE: 3
atggatcatg ctattttggc taccttggtc tgcattttgt tcgtttgttt tcatttgttg      60
tggcgtaggt cctacaagaa ctcttctaaa ttgccaccag gtccaaaacc agttccaatt     120
tttggtaaca tcttcgagtt gggtgaaaag ccacatagat cttttgctga tttggccaag     180
attcacggtc cattgatttc tttgaaattg ggttctgtca cgacgatcgt tgtttcttct     240
tctgatgttg ccaaagaaat gttcttgaag cacgatcaag ttttcgccaa cagaactatt     300
ccagattctg ttagagctgg taaccacgat aagttgtcta tgtcttggtt gccagtttct     360
gctaaatggc gtaacatgag aaagatttct gctgtccaac tgttgtctac ccaaagattg     420
gattctaatc aaggtttgag acaagccaag gttcaacagt tgtggaata cgttcaagaa     480
tgttgcaaaa agggtcaacc agttgatatt ggtagagctg cttttactac ctccttgaac     540
ttgttgtcta cacccttctt ctctatggaa ttggctcaac attcatcctc tgcttctcaa     600
gaattcaagc aattgatgtg gtgcatcatg aagaaattg gtagaccaaa ttacgccgat     660
tacttcccaa ttttgggtta ctttgatcca ttcggtatca gacgtagatt gactgcttac     720
ttcgacaagt tgattgccat cttccaagat atcatccacg aaagattgaa ggctagatct     780
actggttcct cttctaccaa cgatattttg gacactctgc tgaacttgta ccaagaaaac     840
gaattgtcta tggacgagat caaccacttg ttggttgata tttttgatgc cggtactgat     900
accactgctt ctacttttga atgggctatg gctgaattgg ttaagaaccc agaaattatg     960
attaaggccc aggatgagat aacgctgct ttgggtaaag attgctccgt tatccatgaa    1020
tccgatatcg ttaagttgcc atacttgcaa gccattgtca agaaaccttt gagattgcat    1080
ccaccaactg ttttttttgtt gcctagaaaa gccgatttgg atgttgagtt gtatggttac    1140
gttgttccaa agaacgccca atcttggtt aatttgtggg ctataggtag agatccaaag    1200
```

```
gtttggtcta atccagaagt tttctcacca gaaagattct tggactctac cattgatgtt    1260
aagggtagag attttgagtt gttgccattt ggtgcaggta gaagaatttg tccaggtttg    1320
actttggctt ccagaatgtt gaatttgatg ttggccactt tggtccataa cttcaactgg    1380
aaattagagg atggtatgat cccaaaggat ttggatatga ctgaaaagtt cggtattacc    1440
ttgcagaagg ttaacccatt gcaagttatt cccatccaaa agtaa                    1485
```

<210> SEQ ID NO 4
<211> LENGTH: 494
<212> TYPE: PRT
<213> ORGANISM: Opuntia ficus-indica

<400> SEQUENCE: 4

```
Met Asp His Ala Ile Leu Ala Thr Leu Val Cys Ile Leu Phe Val Cys
1               5                   10                  15

Phe His Leu Leu Trp Arg Arg Ser Tyr Lys Asn Ser Ser Lys Leu Pro
            20                  25                  30

Pro Gly Pro Lys Pro Val Pro Ile Phe Gly Asn Ile Phe Glu Leu Gly
        35                  40                  45

Glu Lys Pro His Arg Ser Phe Ala Asp Leu Ala Lys Ile His Gly Pro
    50                  55                  60

Leu Ile Ser Leu Lys Leu Gly Ser Val Thr Thr Ile Val Val Ser Ser
65                  70                  75                  80

Ser Asp Val Ala Lys Glu Met Phe Leu Lys His Asp Gln Val Phe Ala
                85                  90                  95

Asn Arg Thr Ile Pro Asp Ser Val Arg Ala Gly Asn His Asp Lys Leu
            100                 105                 110

Ser Met Ser Trp Leu Pro Val Ser Ala Lys Trp Arg Asn Met Arg Lys
        115                 120                 125

Ile Ser Ala Val Gln Leu Leu Ser Thr Gln Arg Leu Asp Ser Asn Gln
    130                 135                 140

Gly Leu Arg Gln Ala Lys Val Gln Gln Leu Leu Glu Tyr Val Gln Glu
145                 150                 155                 160

Cys Cys Lys Lys Gly Gln Pro Val Asp Ile Gly Arg Ala Ala Phe Thr
                165                 170                 175

Thr Ser Leu Asn Leu Leu Ser Asn Thr Phe Phe Ser Met Glu Leu Ala
            180                 185                 190

Gln His Ser Ser Ser Ala Ser Gln Glu Phe Lys Gln Leu Met Trp Cys
        195                 200                 205

Ile Met Glu Glu Ile Gly Arg Pro Asn Tyr Ala Asp Tyr Phe Pro Ile
    210                 215                 220

Leu Gly Tyr Phe Asp Pro Phe Gly Ile Arg Arg Arg Leu Thr Ala Tyr
225                 230                 235                 240

Phe Asp Lys Leu Ile Ala Ile Phe Gln Asp Ile Ile His Glu Arg Leu
                245                 250                 255

Lys Ala Arg Ser Thr Gly Ser Ser Thr Asn Asp Ile Leu Asp Thr
            260                 265                 270

Leu Leu Asn Leu Tyr Gln Glu Asn Glu Leu Ser Met Asp Glu Ile Asn
        275                 280                 285

His Leu Leu Val Asp Ile Phe Asp Ala Gly Thr Asp Thr Thr Ala Ser
    290                 295                 300

Thr Leu Glu Trp Ala Met Ala Glu Leu Val Lys Asn Pro Glu Ile Met
305                 310                 315                 320

Ile Lys Ala Gln Asp Glu Ile Asn Ala Ala Leu Gly Lys Asp Cys Ser
```

```
                325                 330                 335
Val Ile His Glu Ser Asp Ile Val Lys Leu Pro Tyr Leu Gln Ala Ile
            340                 345                 350
Val Lys Glu Thr Leu Arg Leu His Pro Pro Thr Val Phe Leu Leu Pro
            355                 360                 365
Arg Lys Ala Asp Leu Asp Val Glu Leu Tyr Gly Tyr Val Val Pro Lys
            370                 375                 380
Asn Ala Gln Ile Leu Val Asn Leu Trp Ala Ile Gly Arg Asp Pro Lys
385                 390                 395                 400
Val Trp Ser Asn Pro Glu Val Phe Ser Pro Glu Arg Phe Leu Asp Ser
                405                 410                 415
Thr Ile Asp Val Lys Gly Arg Asp Phe Glu Leu Leu Pro Phe Gly Ala
            420                 425                 430
Gly Arg Arg Ile Cys Pro Gly Leu Thr Leu Ala Ser Arg Met Leu Asn
            435                 440                 445
Leu Met Leu Ala Thr Leu Val His Asn Phe Asn Trp Lys Leu Glu Asp
            450                 455                 460
Gly Met Ile Pro Lys Asp Leu Asp Met Thr Glu Lys Phe Gly Ile Thr
465                 470                 475                 480
Leu Gln Lys Val Asn Pro Leu Gln Val Ile Pro Ile Gln Lys
                485                 490

<210> SEQ ID NO 5
<211> LENGTH: 1496
<212> TYPE: DNA
<213> ORGANISM: Froelichia latifolia

<400> SEQUENCE: 5
tggacaacac taccttggcc gttgttttgt ctgttatgtt cgttttgttc cacctgttga    60
aaaccatctt caccaactct tctaacaaca aattgccacc aggtccaaag agaatgccaa   120
tttttggtaa catcttcgac ttgggtgaaa agcacatag atcttttgct aacttcgcca    180
aaattcacgg tccattgatt tctttgaagt tgggttctgt tacgacgatc gttgtttctt   240
ctgcttctgt tgctgaagag atgttcttga agaatgatca agcttggcc aacagaacca    300
ttccagattc tgttagagct ggtgatcatg acaaattgtc tatgtcttgg ttgccagttt   360
ctgctaaatg gcgtaacttg agaaagattt ctgctgtcca gttgttgtct aaccagagat   420
tggatgcttc tcaaccattg agacaagcta agttaagca gttgttggcc tacgttcaaa    480
actgctctga aaagaatcaa gccgttgata ttggtagagc tgctttcact acttccttga   540
acttgttgtc caacaccttc ttctctatgg aattggcttc tcatgaatcc tctgcttccc   600
aagaattcaa acaattgatg tggaacatca tggaagaaat cggtagacca aattacgccg   660
attttttccc aatcttgggt tacattgatc cattcggtat cagaagaaga ttggctggtt   720
acttcgataa gttgatcgat gttttccagg acatcatcag agaaagacaa agattagag   780
cctctaacgc taacggtact aagcaaactt ctgatatctt ggacaccctg ttgaagttgt   840
acgaagataa cgaattatcc atgggtgaga tcaaccactt gttggttgat atttttgatg    900
ccggtactga taccactgct tctactttgg aatgggctat ggctgaattg gttaagaatc   960
cagaaatgat ggttagagcc cagaacgaaa ttgaagaagt tttgggtaaa gactgctcca  1020
acatccaaga atccgatatt tctaagttgc atacttgca ggccatcatc aaagagtctt    1080
taagattgca tccaccaacc gttttctgt tgccaagaaa agctgatgtt gatgtcgaat    1140
tatacggtta cgttgttcca agaacgcccc aagttttggt taatttgtgg gctataggta   1200
```

-continued

```
gagatccaaa ggtttggaaa aacccagaag tttctcacc agaaaggttc ttggaatgcg    1260
atattgatta caagggtaga gactttgagt tgttgccatt tggtgctggt agaagaattt    1320
gtccaggttt gactttggct tacaggatgt tgaatttgat gttggctacc ttgttgcaca    1380
actacaattg gaaattgggt gatgatatgg acccaaagga cttggatatg aagagaaat    1440 ttggtatcac cctgcagaag attaagccat gcaagttat ccagttgcc aggtaa        1496
```

<210> SEQ ID NO 6
<211> LENGTH: 498
<212> TYPE: PRT
<213> ORGANISM: Froelichia latifolia

<400> SEQUENCE: 6

```
Met Asp Asn Thr Thr Leu Ala Val Val Leu Ser Val Met Phe Val Leu
1               5                   10                  15

Phe His Leu Leu Lys Thr Ile Phe Thr Asn Ser Ser Asn Asn Lys Leu
            20                  25                  30

Pro Pro Gly Pro Lys Arg Met Pro Ile Phe Gly Asn Ile Phe Asp Leu
        35                  40                  45

Gly Glu Lys Pro His Arg Ser Phe Ala Asn Phe Ala Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
                85                  90                  95

Ala Asn Arg Thr Ile Pro Asp Ser Val Arg Ala Gly Asp His Asp Lys
            100                 105                 110

Leu Ser Met Ser Trp Leu Pro Val Ser Ala Lys Trp Arg Asn Leu Arg
        115                 120                 125

Lys Ile Ser Ala Val Gln Leu Leu Ser Asn Gln Arg Leu Asp Ala Ser
    130                 135                 140

Gln Pro Leu Arg Gln Ala Lys Val Lys Gln Leu Leu Ala Tyr Val Gln
145                 150                 155                 160

Asn Cys Ser Glu Lys Asn Gln Ala Val Asp Ile Gly Arg Ala Ala Phe
                165                 170                 175

Thr Thr Ser Leu Asn Leu Leu Ser Asn Thr Phe Phe Ser Met Glu Leu
            180                 185                 190

Ala Ser His Glu Ser Ser Ala Ser Gln Glu Phe Lys Gln Leu Met Trp
        195                 200                 205

Asn Ile Met Glu Glu Ile Gly Arg Pro Asn Tyr Ala Asp Phe Phe Pro
    210                 215                 220

Ile Leu Gly Tyr Ile Asp Pro Phe Gly Ile Arg Arg Arg Leu Ala Gly
225                 230                 235                 240

Tyr Phe Asp Lys Leu Ile Asp Val Phe Gln Asp Ile Ile Arg Glu Arg
                245                 250                 255

Gln Lys Ile Arg Ala Ser Asn Ala Asn Gly Thr Lys Gln Thr Ser Asp
            260                 265                 270

Ile Leu Asp Thr Leu Leu Lys Leu Tyr Glu Asp Asn Glu Leu Ser Met
        275                 280                 285

Gly Glu Ile Asn His Leu Leu Val Asp Ile Phe Asp Ala Gly Thr Asp
    290                 295                 300

Thr Thr Ala Ser Thr Leu Glu Trp Ala Met Ala Glu Leu Val Lys Asn
305                 310                 315                 320
```

```
Pro Glu Met Met Val Arg Ala Gln Asn Glu Ile Glu Val Leu Gly
            325                 330                 335

Lys Asp Cys Ser Asn Ile Gln Glu Ser Asp Ile Ser Lys Leu Pro Tyr
        340                 345                 350

Leu Gln Ala Ile Ile Lys Glu Ser Leu Arg Leu His Pro Pro Thr Val
        355                 360                 365

Phe Leu Leu Pro Arg Lys Ala Asp Val Asp Val Glu Leu Tyr Gly Tyr
        370                 375                 380

Val Val Pro Lys Asn Ala Gln Val Leu Val Asn Leu Trp Ala Ile Gly
385                 390                 395                 400

Arg Asp Pro Lys Val Trp Lys Asn Pro Glu Val Phe Ser Pro Glu Arg
                405                 410                 415

Phe Leu Glu Cys Asp Ile Asp Tyr Lys Gly Arg Asp Phe Glu Leu Leu
            420                 425                 430

Pro Phe Gly Ala Gly Arg Arg Ile Cys Pro Gly Leu Thr Leu Ala Tyr
        435                 440                 445

Arg Met Leu Asn Leu Met Leu Ala Thr Leu Leu His Asn Tyr Asn Trp
        450                 455                 460

Lys Leu Gly Asp Asp Met Asp Pro Lys Asp Leu Asp Met Glu Glu Lys
465                 470                 475                 480

Phe Gly Ile Thr Leu Gln Lys Ile Lys Pro Leu Gln Val Ile Pro Val
                485                 490                 495

Ala Arg

<210> SEQ ID NO 7
<211> LENGTH: 1497
<212> TYPE: DNA
<213> ORGANISM: Beta vulgaris

<400> SEQUENCE: 7
atggataacg ctaccttggc cgttatcttg tctattttgt tcgttttcta ccacatcttc      60
aagtcgttct tcaccaactc ttcatctaga agattgccac aggtccaaa accagttcca     120 atttttggta acatcttcga cttgggtgaa aagccacata gatcttttgc taacttgtcc     180
aagattcacg gtccattgat ttctttgaag ttgggttctg ttacgacgat cgttgtttct     240
tctgcttctg ttgctgaaga gatgttcttg aagaatgatc aagctttggc caacagaacc     300
attccagatt ctgttagagc tggtgatcat gacaaattgt ctatgtcttg gttgccagtt     360
tctcaaaagt ggcgtaacat gagaaagatt tctgctgttc agttgctgtc caatcaaaag     420
ttggatgctt ctcaaccatt gagacaagct aagtaagc agttgttgtc ctacgttcaa     480
gtctgctctg aaaaatgca accagttgat attggtagag ctgctttcac tacttccttg     540
aacttgttgt ctaacacctt cttctccatt gaattggcct tcatgaatc ttcagcttcc     600 caagaattca agcaattgat gtggaacatc atggaagaaa tcggtagacc aaattacgcc     660
gattttttcc aatcttggg ttacattgat ccattcggta tcagaagaag attggctggt     720
tacttcgata gttgatcga tgttttccag gacatcatca gagaaagaca gaagttgaga     780
tcctctaatt cttctggtgc taagcaaact aacgacatct ggatactttt gttgaagttg     840
cacgaagata acgagttgtc tatgccagaa atcaaccact tgttggttga tattttcgat     900
gctggtactg ataccactgc ttctactttg aatgggcta tggctgaatt ggttaagaat     960
ccagaaatga tgaccaaggt ccagatcgaa attgaacaag ctttaggtaa ggattgcttg    1020
gacatccaag aatccgatat ttctaagttg ccatacttgc aggccatcat caaagagact    1080
```

```
ttgagattgc atccaccaac cgttttttg ttgccaagaa aggctgataa cgatgttgag    1140
ttgtatggtt acgttgttcc aaagaacgct caagttttgg ttaacttgtg ggctataggt   1200
agagatccaa aggtttggaa aaacccagaa gttttctcac cagaaaggtt cttggattgc   1260
aacattgatt acaagggtag agacttcgag ttgttgccat ttggtgctgg tagaagaatt   1320
tgtccaggtt tgactttggc ttacaggatg ttgaatttga tgttggctac cttgttgcag   1380
aactacaatt ggaaattgga ggatggtatc aacccaaagg acttggatat ggacgaaaag   1440
tttggtatca ccttgcaaaa ggttaagcca ttgcaagtta ttcccgttcc aagatga     1497
```

<210> SEQ ID NO 8
<211> LENGTH: 498
<212> TYPE: PRT
<213> ORGANISM: Beta vulgaris

<400> SEQUENCE: 8

```
Met Asp Asn Ala Thr Leu Ala Val Ile Leu Ser Ile Leu Phe Val Phe
1               5                   10                  15

Tyr His Ile Phe Lys Ser Phe Phe Thr Asn Ser Ser Ser Arg Arg Leu
            20                  25                  30

Pro Pro Gly Pro Lys Pro Val Pro Ile Phe Gly Asn Ile Phe Asp Leu
        35                  40                  45

Gly Glu Lys Pro His Arg Ser Phe Ala Asn Leu Ser Lys Ile His Gly
    50                  55                  60

Pro Leu Ile Ser Leu Lys Leu Gly Ser Val Thr Thr Ile Val Val Ser
65                  70                  75                  80

Ser Ala Ser Val Ala Glu Glu Met Phe Leu Lys Asn Asp Gln Ala Leu
                85                  90                  95

Ala Asn Arg Thr Ile Pro Asp Ser Val Arg Ala Gly Asp His Asp Lys
            100                 105                 110

Leu Ser Met Ser Trp Leu Pro Val Ser Gln Lys Trp Arg Asn Met Arg
        115                 120                 125

Lys Ile Ser Ala Val Gln Leu Leu Ser Asn Gln Lys Leu Asp Ala Ser
    130                 135                 140

Gln Pro Leu Arg Gln Ala Lys Val Lys Gln Leu Leu Ser Tyr Val Gln
145                 150                 155                 160

Val Cys Ser Glu Lys Met Gln Pro Val Asp Ile Gly Arg Ala Ala Phe
                165                 170                 175

Thr Thr Ser Leu Asn Leu Leu Ser Asn Thr Phe Phe Ser Ile Glu Leu
            180                 185                 190

Ala Ser His Glu Ser Ser Ala Ser Gln Glu Phe Lys Gln Leu Met Trp
        195                 200                 205

Asn Ile Met Glu Glu Ile Gly Arg Pro Asn Tyr Ala Asp Phe Phe Pro
    210                 215                 220

Ile Leu Gly Tyr Ile Asp Pro Phe Gly Ile Arg Arg Arg Leu Ala Gly
225                 230                 235                 240

Tyr Phe Asp Lys Leu Ile Asp Val Phe Gln Asp Ile Ile Arg Glu Arg
                245                 250                 255

Gln Lys Leu Arg Ser Ser Asn Ser Ser Gly Ala Lys Gln Thr Asn Asp
            260                 265                 270

Ile Leu Asp Thr Leu Leu Lys Leu His Glu Asp Asn Glu Leu Ser Met
        275                 280                 285

Pro Glu Ile Asn His Leu Leu Val Asp Ile Phe Asp Ala Gly Thr Asp
    290                 295                 300
```

Thr Thr Ala Ser Thr Leu Glu Trp Ala Met Ala Glu Leu Val Lys Asn
305                 310                 315                 320

Pro Glu Met Met Thr Lys Val Gln Ile Glu Ile Glu Gln Ala Leu Gly
            325                 330                 335

Lys Asp Cys Leu Asp Ile Gln Glu Ser Asp Ile Ser Lys Leu Pro Tyr
            340                 345                 350

Leu Gln Ala Ile Ile Lys Glu Thr Leu Arg Leu His Pro Pro Thr Val
        355                 360                 365

Phe Leu Leu Pro Arg Lys Ala Asp Asn Asp Val Glu Leu Tyr Gly Tyr
370                 375                 380

Val Val Pro Lys Asn Ala Gln Val Leu Val Asn Leu Trp Ala Ile Gly
385                 390                 395                 400

Arg Asp Pro Lys Val Trp Lys Asn Pro Glu Val Phe Ser Pro Glu Arg
                405                 410                 415

Phe Leu Asp Cys Asn Ile Asp Tyr Lys Gly Arg Asp Phe Glu Leu Leu
                420                 425                 430

Pro Phe Gly Ala Gly Arg Arg Ile Cys Pro Gly Leu Thr Leu Ala Tyr
            435                 440                 445

Arg Met Leu Asn Leu Met Leu Ala Thr Leu Leu Gln Asn Tyr Asn Trp
450                 455                 460

Lys Leu Glu Asp Gly Ile Asn Pro Lys Asp Leu Asp Met Asp Glu Lys
465                 470                 475                 480

Phe Gly Ile Thr Leu Gln Lys Val Lys Pro Leu Gln Val Ile Pro Val
                485                 490                 495

Pro Arg

<210> SEQ ID NO 9
<211> LENGTH: 1512
<212> TYPE: DNA
<213> ORGANISM: Abronia nealleyi

<400> SEQUENCE: 9

```
atggaaaaca ccaccttggg tgttattttg ctactatttt tcttgacctt ccacatcatg      60
aagatgctgt tgtctccaaa caaagctaaa ttgccaccag gtccaagacc attgccaatt     120
attggtaaca tttttggagtt gggtgataag ccacatagat cttttgctaa cttggctaaa     180
atctacggtc cattgattac cttgagattg ggttctgtta ctaccgttgt tgtctcttca     240
tctcaagttg ccaaagaaat gttcttgaag aacgatcaat ccttggccaa cagaactatt     300
ccagattctg ttagagctgg taaccatcac aaattgtcta tgtcttggtt gccagttttct    360
gctaagtggc gtaatttcag aaagatttct gccgttgagt tgttgtcctc tcaaagattg     420
gatgcttctc aagctcatag acaagctaag gttgaacagt tgatcgaata cgtcaaagag     480
tgctctaaga ttggtcaatg cgttgatatt ggtagattgg ctttcaccac ttccttgaac     540
ttgttgtcta caccttcttt cagcaaagaa ttggcctctt tggattctaa caacgcccaa     600
gaattcaagc aattgatgtg gtgcattatg aagaaatcg gtagaccaaa ttacgctgat     660
tacttcccaa ttttgggtta cgttgatcca ttcggtgtta agaagatt gtccagatac     720
ttcgaccagt tgattgaagt gttccaagaa atcatcagag agaggttgtc taagaacaac     780
gaaaaggttg ataacaagaa cgacattttg gccactttgc tgcacttgta caaacagaat     840
gaattgtcca tggatgagat caaccacttg ttggttgata ttttcgatgc tggtactgat     900
accactgctt ctactttgga atgggctatg tctgaattga tcaagaaccc acatattatg     960
tccaaggctc aagctgaagt tagaagggct actgttttctc atggtggtgc tactgttgct    1020
```

```
gctgttcaag aatctgatat ttccaacttg ccttacatcc agtccatcat caaagaaact      1080
ttgagattgc atccaccaac cgttttttg ttgccaagaa aagctgatgt tgacgttcag       1140
ttgtacggtt atgttgttcc aaagaacgct caagttttgg ttaacttgtg ggcaattggt      1200
agagatccaa atgtttggcc agatccagaa gttttagac cagaaaggtt tatggattgc       1260
ggtgttgatg ttaagggtag agactttgaa ttattgccat tggtgccgg tagaagaatt      1320 tgtcctggtt tgtctttggc ttacaggatg ttgaatctga tgttggctaa tctgttcac      1380 tctttcgatt ggaaattgcc agattccggt aatggttttg gttctgatcc taatggtttg     1440
gacatggacg aaaagtttgg tatcaccttg caaaaagtcg aaccattgaa ggttattcca     1500
acgccaagat ga                                                         1512
```

<210> SEQ ID NO 10
<211> LENGTH: 503
<212> TYPE: PRT
<213> ORGANISM: Abronia nealleyi

<400> SEQUENCE: 10

```
Met Glu Asn Thr Thr Leu Gly Val Ile Leu Ala Thr Ile Phe Leu Thr
1               5                   10                  15

Phe His Ile Met Lys Met Leu Leu Ser Pro Asn Lys Ala Lys Leu Pro
            20                  25                  30

Pro Gly Pro Arg Pro Leu Pro Ile Ile Gly Asn Ile Leu Glu Leu Gly
        35                  40                  45

Asp Lys Pro His Arg Ser Phe Ala Asn Leu Ala Lys Ile Tyr Gly Pro
    50                  55                  60

Leu Ile Thr Leu Arg Leu Gly Ser Val Thr Thr Val Val Ser Ser
65                  70                  75                  80

Ser Gln Val Ala Lys Glu Met Phe Leu Lys Asn Asp Gln Ser Leu Ala
                85                  90                  95

Asn Arg Thr Ile Pro Asp Ser Val Arg Ala Gly Asn His His Lys Leu
            100                 105                 110

Ser Met Ser Trp Leu Pro Val Ser Ala Lys Trp Arg Asn Phe Arg Lys
        115                 120                 125

Ile Ser Ala Val Glu Leu Leu Ser Ser Gln Arg Leu Asp Ala Ser Gln
    130                 135                 140

Ala His Arg Gln Ala Lys Val Glu Gln Leu Ile Glu Tyr Val Lys Glu
145                 150                 155                 160

Cys Ser Lys Ile Gly Gln Cys Val Asp Ile Gly Arg Leu Ala Phe Thr
                165                 170                 175

Thr Ser Leu Asn Leu Leu Ser Asn Thr Phe Phe Ser Lys Glu Leu Ala
            180                 185                 190

Ser Leu Asp Ser Asn Asn Ala Gln Glu Phe Lys Gln Leu Met Trp Cys
        195                 200                 205

Ile Met Glu Glu Ile Gly Arg Pro Asn Tyr Ala Asp Tyr Phe Pro Ile
    210                 215                 220

Leu Gly Tyr Val Asp Pro Phe Gly Val Arg Arg Leu Ser Arg Tyr
225                 230                 235                 240

Phe Asp Gln Leu Ile Glu Val Phe Gln Glu Ile Arg Glu Arg Leu
                245                 250                 255

Ser Lys Asn Asn Glu Lys Val Asp Asn Lys Asn Asp Ile Leu Ala Thr
            260                 265                 270

Leu Leu His Leu Tyr Lys Gln Asn Glu Leu Ser Met Asp Glu Ile Asn
```

```
                275                 280                 285
His Leu Leu Val Asp Ile Phe Asp Ala Gly Thr Asp Thr Thr Ala Ser
    290                 295                 300

Thr Leu Glu Trp Ala Met Ser Glu Leu Ile Lys Asn Pro His Ile Met
305                 310                 315                 320

Ser Lys Ala Gln Ala Glu Val Arg Arg Ala Thr Val Ser His Gly Gly
                325                 330                 335

Ala Thr Val Ala Ala Val Gln Glu Ser Asp Ile Ser Asn Leu Pro Tyr
            340                 345                 350

Ile Gln Ser Ile Ile Lys Glu Thr Leu Arg Leu His Pro Pro Thr Val
                355                 360                 365

Phe Leu Leu Pro Arg Lys Ala Asp Val Asp Val Gln Leu Tyr Gly Tyr
370                 375                 380

Val Val Pro Lys Asn Ala Gln Val Leu Val Asn Leu Trp Ala Ile Gly
385                 390                 395                 400

Arg Asp Pro Asn Val Trp Pro Asp Pro Glu Val Phe Arg Pro Glu Arg
                405                 410                 415

Phe Met Asp Cys Gly Val Asp Val Lys Gly Arg Asp Phe Glu Leu Leu
                420                 425                 430

Pro Phe Gly Ala Gly Arg Arg Ile Cys Pro Gly Leu Ser Leu Ala Tyr
            435                 440                 445

Arg Met Leu Asn Leu Met Leu Ala Asn Leu Val His Ser Phe Asp Trp
450                 455                 460

Lys Leu Pro Asp Ser Gly Asn Gly Phe Gly Ser Asp Pro Asn Gly Leu
465                 470                 475                 480

Asp Met Asp Glu Lys Phe Gly Ile Thr Leu Gln Lys Val Glu Pro Leu
                485                 490                 495

Lys Val Ile Pro Thr Pro Arg
            500

<210> SEQ ID NO 11
<211> LENGTH: 1500
<212> TYPE: DNA
<213> ORGANISM: Beta vulgaris

<400> SEQUENCE: 11
atggacaaca ctaccttggc cttgatcttg tcatctttgt tcgtttgctt ccagttgatc      60
aggtctttca ttaaccatac caagaagtcc aacaaattgc caccaggtcc aaaaagaatg     120
ccaattttcg gtaacatctt cgacttgggt gaaaagccac atagatcttt tgctaacttg     180
gctaagattc acggtccatt ggtttcttta caattgggtt ctgttactac cgtcgttgtt     240
tcttctgctg atgttgctaa agaaatgttc ttgaagaacg atcaagcttt ggccaacaga     300
actattccag attctgttag agctggtgat cacgataagt tgtctatgtc ttggttgcca     360
gtttctgcta atggcgtaa cttgagaaag atttctgctg ccaactgtt gtctacccaa      420 agattggatg cttctcaagc tcatagacaa tctaaggttc aacagttgtt ggaatacgtt     480
cacgattgct ctaaaaaggg tcaaccagtt gatattggta gagctgcttt tactacctcc     540
ttgaacttgt tgtctaacac cttcttctct gttgaattgg cctctcatga atcttcagct     600
tcccaagaat tcaagcaatt gatgtggaac atcatggaag aaatcggtag accaaattac     660
gccgattttt tcccaatttt gggttacttg atccattcg gtatcagaag aagattggct     720
ggttacttcg accaattgat tgctgttttc caagacatca ttggtgagag acaaaaaatc     780
agatccgcta atttgtctgg tggtaagcaa actaacgata tcttggatac cctgctgaac     840
```

```
ttgtacgacg aaaaagaatt atccatgggt gagatcaacc acttgttggt tgatattttt    900
gatgccggta ctgataccac tgcttctact ttggaatggg ctatggctga attggttaag    960
aacccatata tgatggttaa ggtccaggac gaaattgaaa aggctattgg taaaggttgc   1020
tccatggttc aagaatccga tatttctaag ttgccatact tgcaggccat catcaaagaa   1080
actttgagat tgcatccacc aaccgttttt tgttgccaa gaaagctga tgcagatgtt    1140
gagttgtatg ttacatcgt tccaaagaat gctcaagtct tggttaactt gtgggctata   1200
ggtagagatc caaggtttg gaaaaaccca gaagttttct caccagaaag gttcttggaa   1260
tccaacattg attacaaggg tagagacttt gagttgttgc catttggtgc tggtagaaga   1320
atttgtccag gtttgacttt ggcttacagg atgttgaact taatgatggc caacttcttg   1380
cactcttacg attggaaatt ggaagatggt atgcacccta aggatttgga tatggacgaa   1440
aagtttggta tcaccttgca aaaggttaag ccattgcaag ttattccagt gccaagatga   1500
```

<210> SEQ ID NO 12
<211> LENGTH: 499
<212> TYPE: PRT
<213> ORGANISM: Beta vulgaris

<400> SEQUENCE: 12

```
Met Asp Asn Thr Thr Leu Ala Leu Ile Leu Ser Ser Leu Phe Val Cys
1               5                   10                  15

Phe Gln Leu Ile Arg Ser Phe Ile Asn His Thr Lys Lys Ser Asn Lys
            20                  25                  30

Leu Pro Pro Gly Pro Lys Arg Met Pro Ile Phe Gly Asn Ile Phe Asp
        35                  40                  45

Leu Gly Glu Lys Pro His Arg Ser Phe Ala Asn Leu Ala Lys Ile His
    50                  55                  60

Gly Pro Leu Val Ser Leu Gln Leu Gly Ser Val Thr Thr Val Val Val
65                  70                  75                  80

Ser Ser Ala Asp Val Ala Lys Glu Met Phe Leu Lys Asn Asp Gln Ala
                85                  90                  95

Leu Ala Asn Arg Thr Ile Pro Asp Ser Val Arg Ala Gly Asp His Asp
            100                 105                 110

Lys Leu Ser Met Ser Trp Leu Pro Val Ser Ala Lys Trp Arg Asn Leu
        115                 120                 125

Arg Lys Ile Ser Ala Val Gln Leu Leu Ser Thr Gln Arg Leu Asp Ala
    130                 135                 140

Ser Gln Ala His Arg Gln Ser Lys Val Gln Gln Leu Leu Glu Tyr Val
145                 150                 155                 160

His Asp Cys Ser Lys Lys Gly Gln Pro Val Asp Ile Gly Arg Ala Ala
                165                 170                 175

Phe Thr Thr Ser Leu Asn Leu Leu Ser Asn Thr Phe Phe Ser Val Glu
            180                 185                 190

Leu Ala Ser His Glu Ser Ser Ala Ser Gln Glu Phe Lys Gln Leu Met
        195                 200                 205

Trp Asn Ile Met Glu Glu Ile Gly Arg Pro Asn Tyr Ala Asp Phe Phe
    210                 215                 220

Pro Ile Leu Gly Tyr Leu Asp Pro Phe Gly Ile Arg Arg Arg Leu Ala
225                 230                 235                 240

Gly Tyr Phe Asp Gln Leu Ile Ala Val Phe Gln Asp Ile Ile Gly Glu
                245                 250                 255
```

```
Arg Gln Lys Ile Arg Ser Ala Asn Leu Ser Gly Gly Lys Gln Thr Asn
                260                 265                 270
Asp Ile Leu Asp Thr Leu Leu Asn Leu Tyr Asp Glu Lys Glu Leu Ser
            275                 280                 285
Met Gly Glu Ile Asn His Leu Leu Val Asp Ile Phe Asp Ala Gly Thr
290                 295                 300
Asp Thr Thr Ala Ser Thr Leu Glu Trp Ala Met Ala Glu Leu Val Lys
305                 310                 315                 320
Asn Pro Tyr Met Met Val Lys Val Gln Asp Glu Ile Glu Lys Ala Ile
                325                 330                 335
Gly Lys Gly Cys Ser Met Val Gln Glu Ser Asp Ile Ser Lys Leu Pro
                340                 345                 350
Tyr Leu Gln Ala Ile Ile Lys Glu Thr Leu Arg Leu His Pro Pro Thr
                355                 360                 365
Val Phe Leu Leu Pro Arg Lys Ala Asp Ala Asp Val Glu Leu Tyr Gly
            370                 375                 380
Tyr Ile Val Pro Lys Asn Ala Gln Val Leu Val Asn Leu Trp Ala Ile
385                 390                 395                 400
Gly Arg Asp Pro Lys Val Trp Lys Asn Pro Glu Val Phe Ser Pro Glu
                405                 410                 415
Arg Phe Leu Glu Ser Asn Ile Asp Tyr Lys Gly Arg Asp Phe Glu Leu
                420                 425                 430
Leu Pro Phe Gly Ala Gly Arg Arg Ile Cys Pro Gly Leu Thr Leu Ala
            435                 440                 445
Tyr Arg Met Leu Asn Leu Met Met Ala Asn Phe Leu His Ser Tyr Asp
450                 455                 460
Trp Lys Leu Glu Asp Gly Met His Pro Lys Asp Leu Asp Met Asp Glu
465                 470                 475                 480
Lys Phe Gly Ile Thr Leu Gln Lys Val Lys Pro Leu Gln Val Ile Pro
                485                 490                 495
Val Pro Arg

<210> SEQ ID NO 13
<211> LENGTH: 1503
<212> TYPE: DNA
<213> ORGANISM: Beta vulgaris

<400> SEQUENCE: 13
atggacaaca ctaccttggc cttgatcttg tcatctttgt tcgtttgctt ccagttgatc     60
aggtccttta ttaaccatgc caagaagtct aacaaattgc caccaggtcc aaagagaatg    120
ccaattttg gtaacatctt cgacttgggt gaaaagccac atagatcttt tgctaacttg    180
gctaagattc acggtccatt ggtttcttta caattgggtt ctgttactac cgtcgttgtt    240
tcttctgctg atgttgctaa agaaatgttc ttgaagaacg atcaagcttt ggccaacaga    300
actattccag attctgttag agctggtgat cacgataagt tgtctatgtc ttggttgcca    360
gtttctgcta atggcgtaa cttgagaaag atttctgctg tccaactgtt gtctacccaa    420
agattggatg cttctcaagc tcatagacaa tctaaggttc aacagttgtt ggaatacgtt    480
cacgattgct ctaaaaaggg tcaaccagtt gatattggta gagctgcttt tactacctcc    540
ttgaacttgt tgtctaacac cttcttctct gttgaattgg cctctcatga atcttcagct    600
tcccaagaat tcaagcaatt gatgtggaac atcatggaag aaatcggtag accaaaattac    660
gccgattttt tcccaatttt gggttacttg gatccattcg gtatcagaag aagattggct    720
```

```
ggttacttcg accaattgat tgctgttttc caagacatca ttggtgagag acaaaaaatc    780
agatccgcta atttgtctgg tggtaagcaa actaccaacg atattttgga taccctgctg    840
aacttgtacg acgagaaaga attatctatg ggtgagatca accacttgtt ggttgatatt    900
tttgatgccg gtactgatac cactgcttct actttggaat gggctatggc tgaattggtt    960
aagaatccag atatgatggt taaggtccag gacgaaattg aacaagctat tggtaaaggt   1020
tgctccatgg ttcaagaatc tgatatctct aagttgccat acttgcaggc cattatcaaa   1080
gaaaccttga gattgcatcc accaaccgtt tttttgttgc aagaaaagc tgatgcagat    1140
gttgagttgt atggttacgt tgttccaaag aatgctcaag tcttggttaa cttgtgggct   1200
ataggtagag atccaaaggt ttggaaaaac ccagaagttt tctcaccaga aaggttcttg   1260
gaatccaaca ttgattacaa gggtagagac tttgagttgt tgccatttgg tgctggtaga   1320
agaatttgtc aggtttgac tttggcttac aggatgttga atttgatgat ggccaacttc    1380
ttgcactctt acgattggaa attggaagat ggtatgcacc ctaaggattt ggatatggac   1440
gaaaagtttg gtatcacctt gcaaaaggtt aagccattgc aagttattcc agtgccaaga   1500
tga                                                                 1503

<210> SEQ ID NO 14
<211> LENGTH: 500
<212> TYPE: PRT
<213> ORGANISM: Beta vulgaris

<400> SEQUENCE: 14

Met Asp Asn Thr Thr Leu Ala Leu Ile Leu Ser Ser Leu Phe Val Cys
1               5                   10                  15

Phe Gln Leu Ile Arg Ser Phe Ile Asn His Ala Lys Lys Ser Asn Lys
            20                  25                  30

Leu Pro Pro Gly Pro Lys Arg Met Pro Ile Phe Gly Asn Ile Phe Asp
        35                  40                  45

Leu Gly Glu Lys Pro His Arg Ser Phe Ala Asn Leu Ala Lys Ile His
    50                  55                  60

Gly Pro Leu Val Ser Leu Gln Leu Gly Ser Val Thr Thr Val Val Val
65                  70                  75                  80

Ser Ser Ala Asp Val Ala Lys Glu Met Phe Leu Lys Asn Asp Gln Ala
                85                  90                  95

Leu Ala Asn Arg Thr Ile Pro Asp Ser Val Arg Ala Gly Asp His Asp
            100                 105                 110

Lys Leu Ser Met Ser Trp Leu Pro Val Ser Ala Lys Trp Arg Asn Leu
        115                 120                 125

Arg Lys Ile Ser Ala Val Gln Leu Leu Ser Thr Gln Arg Leu Asp Ala
    130                 135                 140

Ser Gln Ala His Arg Gln Ser Lys Val Gln Gln Leu Leu Glu Tyr Val
145                 150                 155                 160

His Asp Cys Ser Lys Lys Gly Gln Pro Val Asp Ile Gly Arg Ala Ala
                165                 170                 175

Phe Thr Thr Ser Leu Asn Leu Leu Ser Asn Thr Phe Phe Ser Val Glu
            180                 185                 190

Leu Ala Ser His Glu Ser Ser Ala Ser Gln Glu Phe Lys Gln Leu Met
        195                 200                 205

Trp Asn Ile Met Glu Glu Ile Gly Arg Pro Asn Tyr Ala Asp Phe Phe
    210                 215                 220

Pro Ile Leu Gly Tyr Leu Asp Pro Phe Gly Ile Arg Arg Arg Leu Ala
```

```
                    225                 230                 235                 240
        Gly Tyr Phe Asp Gln Leu Ile Ala Val Phe Gln Asp Ile Ile Gly Glu
                        245                 250                 255
        Arg Gln Lys Ile Arg Ser Ala Asn Leu Ser Gly Gly Lys Gln Thr Thr
                        260                 265                 270
        Asn Asp Ile Leu Asp Thr Leu Leu Asn Leu Tyr Asp Glu Lys Glu Leu
                        275                 280                 285
        Ser Met Gly Glu Ile Asn His Leu Leu Val Asp Ile Phe Asp Ala Gly
                        290                 295                 300
        Thr Asp Thr Thr Ala Ser Thr Leu Glu Trp Ala Met Ala Glu Leu Val
        305                 310                 315                 320
        Lys Asn Pro Asp Met Met Val Lys Val Gln Asp Glu Ile Glu Gln Ala
                        325                 330                 335
        Ile Gly Lys Gly Cys Ser Met Val Gln Glu Ser Asp Ile Ser Lys Leu
                        340                 345                 350
        Pro Tyr Leu Gln Ala Ile Ile Lys Glu Thr Leu Arg Leu His Pro Pro
                        355                 360                 365
        Thr Val Phe Leu Leu Pro Arg Lys Ala Asp Ala Asp Val Glu Leu Tyr
                        370                 375                 380
        Gly Tyr Val Val Pro Lys Asn Ala Gln Val Leu Val Asn Leu Trp Ala
        385                 390                 395                 400
        Ile Gly Arg Asp Pro Lys Val Trp Lys Asn Pro Glu Val Phe Ser Pro
                        405                 410                 415
        Glu Arg Phe Leu Glu Ser Asn Ile Asp Tyr Lys Gly Arg Asp Phe Glu
                        420                 425                 430
        Leu Leu Pro Phe Gly Ala Gly Arg Arg Ile Cys Pro Gly Leu Thr Leu
                        435                 440                 445
        Ala Tyr Arg Met Leu Asn Leu Met Met Ala Asn Phe Leu His Ser Tyr
                        450                 455                 460
        Asp Trp Lys Leu Glu Asp Gly Met His Pro Lys Asp Leu Asp Met Asp
        465                 470                 475                 480
        Glu Lys Phe Gly Ile Thr Leu Gln Lys Val Lys Pro Leu Gln Val Ile
                        485                 490                 495
        Pro Val Pro Arg
                500

<210> SEQ ID NO 15
<211> LENGTH: 1500
<212> TYPE: DNA
<213> ORGANISM: Beta vulgaris

<400> SEQUENCE: 15
atggacaaca ctaccttggc cttgatcttg tcatctttgt tcgtttgctt ccagttgatc        60
aggtccttta ttaaccatgc caagaagtct aacaaattgc caccaggtcc aaagagaatg      120 ccaattttg gtaacatctt cgacttgggt gaaaagccac atagatcttt tgctaacttg       180
gctaagattc acggtccatt ggtttcttta caattgggtt ctgttactac cgtcgttgtt      240
tcttctgctg atgttgctaa agaaatgttc ttgaagaacg atcaagcttt ggccaacaga      300
actattccag attctgttag agctggtgat cacgataagt tgtctatgtc ttggttgcca      360
gtttctgcta aatggcgtaa cttgagaaag atttctgctg tccaactgtt gtctacccaa      420
agattggatg cttctcaagc tcatagacaa tctaaggttc aacagttgtt ggaatacgtt      480
cacgattgct ctaaaaaggg tcaaccagtt gatattggta gagctgcttt tactacctcc      540
```

```
ttgaacttgt tgtctaacac cttcttctct gttgaattgg cctctcatga atcttcagct    600
tcccaagaat tcaagcaatt gatgtggaac atcatggaag aaatcggtag accaaattac    660
gccgattttt tcccaatttt gggttacttg gatccattcg gtatcagaag aagattggct    720
ggttacttcg accaattgat tgctgttttc caagacatca ttggtgagag acaaaaaatc    780
agatccgcta atttgtctgg tggtaagcaa actaacgata tcttggatac cctgctgaac    840
ttgtacgacg aaaagaatt atccatgggt gagatcaacc acttgttggt tgatattttt    900
gatgccggta ctgataccac tgcttctact ttggaatggg ctatggctga attggttaag    960
aatccagata tgatggttaa ggtccaggac gaaattgaac aagctattgg taaaggttgc   1020
tccatggttc aagaatctga tatctctaag ttgccatact gcaggccat tatcaaagaa    1080 accttgagat tgcatccacc aaccgttttt ttgttgccaa gaaaagctga tgcagatgtt   1140
gagttgtatg gttacgttgt tccaaagaat gctcaagtct tggttaactt gtgggctata   1200
ggtagagatc caaggtttg gaaaaaccca gaagttttct caccagaaag gttcttggaa    1260
tccaacattg attacaaggg tagagacttt gagttgttgc catttggtgc tggtagaaga   1320
atttgtccag gtttgacttt ggcttacagg atgttgaatt tgatgatggc caacttcttg   1380
cactcttacg attggaaatt ggaagatggt atgcaccta aggatttgga tatggacgaa    1440
aagtttggta tcaccttgca aaaggttaag ccattgcaag ttattccagt gccaagatga   1500
```

<210> SEQ ID NO 16
<211> LENGTH: 499
<212> TYPE: PRT
<213> ORGANISM: Beta vulgaris

<400> SEQUENCE: 16

Met Asp Asn Thr Thr Leu Ala Leu Ile Leu Ser Ser Leu Phe Val Cys
1               5                   10                  15

Phe Gln Leu Ile Arg Ser Phe Ile Asn His Ala Lys Lys Ser Asn Lys
                20                  25                  30

Leu Pro Pro Gly Pro Lys Arg Met Pro Ile Phe Gly Asn Ile Phe Asp
            35                  40                  45

Leu Gly Glu Lys Pro His Arg Ser Phe Ala Asn Leu Ala Lys Ile His
        50                  55                  60

Gly Pro Leu Val Ser Leu Gln Leu Gly Ser Val Thr Thr Val Val Val
65                  70                  75                  80

Ser Ser Ala Asp Val Ala Lys Glu Met Phe Leu Lys Asn Asp Gln Ala
                85                  90                  95

Leu Ala Asn Arg Thr Ile Pro Asp Ser Val Arg Ala Gly Asp His Asp
            100                 105                 110

Lys Leu Ser Met Ser Trp Leu Pro Val Ser Ala Lys Trp Arg Asn Leu
        115                 120                 125

Arg Lys Ile Ser Ala Val Gln Leu Leu Ser Thr Gln Arg Leu Asp Ala
    130                 135                 140

Ser Gln Ala His Arg Gln Ser Lys Val Gln Gln Leu Leu Glu Tyr Val
145                 150                 155                 160

His Asp Cys Ser Lys Lys Gly Gln Pro Val Asp Ile Gly Arg Ala Ala
                165                 170                 175

Phe Thr Thr Ser Leu Asn Leu Leu Ser Asn Thr Phe Phe Ser Val Glu
            180                 185                 190

Leu Ala Ser His Glu Ser Ser Ala Ser Gln Glu Phe Lys Gln Leu Met
        195                 200                 205

```
Trp Asn Ile Met Glu Glu Ile Gly Arg Pro Asn Tyr Ala Asp Phe Phe
    210                 215                 220
Pro Ile Leu Gly Tyr Leu Asp Pro Phe Gly Ile Arg Arg Leu Ala
225                 230                 235                 240
Gly Tyr Phe Asp Gln Leu Ile Ala Val Phe Gln Asp Ile Ile Gly Glu
                    245                 250                 255
Arg Gln Lys Ile Arg Ser Ala Asn Leu Ser Gly Gly Lys Gln Thr Asn
                260                 265                 270
Asp Ile Leu Asp Thr Leu Leu Asn Leu Tyr Asp Glu Lys Glu Leu Ser
            275                 280                 285
Met Gly Glu Ile Asn His Leu Leu Val Asp Ile Phe Asp Ala Gly Thr
290                 295                 300
Asp Thr Thr Ala Ser Thr Leu Glu Trp Ala Met Ala Glu Leu Val Lys
305                 310                 315                 320
Asn Pro Asp Met Met Lys Val Gln Asp Glu Ile Glu Gln Ala Ile
                325                 330                 335
Gly Lys Gly Cys Ser Met Val Gln Glu Ser Asp Ile Ser Lys Leu Pro
                340                 345                 350
Tyr Leu Gln Ala Ile Ile Lys Glu Thr Leu Arg Leu His Pro Pro Thr
            355                 360                 365
Val Phe Leu Leu Pro Arg Lys Ala Asp Ala Asp Val Glu Leu Tyr Gly
370                 375                 380
Tyr Val Val Pro Lys Asn Ala Gln Val Leu Val Asn Leu Trp Ala Ile
385                 390                 395                 400
Gly Arg Asp Pro Lys Val Trp Lys Asn Pro Glu Val Phe Ser Pro Glu
                405                 410                 415
Arg Phe Leu Glu Ser Asn Ile Asp Tyr Lys Gly Arg Asp Phe Glu Leu
            420                 425                 430
Leu Pro Phe Gly Ala Gly Arg Arg Ile Cys Pro Gly Leu Thr Leu Ala
        435                 440                 445
Tyr Arg Met Leu Asn Leu Met Met Ala Asn Phe Leu His Ser Tyr Asp
    450                 455                 460
Trp Lys Leu Glu Asp Gly Met His Pro Lys Asp Leu Asp Met Asp Glu
465                 470                 475                 480
Lys Phe Gly Ile Thr Leu Gln Lys Val Lys Pro Leu Gln Val Ile Pro
                485                 490                 495
Val Pro Arg

<210> SEQ ID NO 17
<211> LENGTH: 1488
<212> TYPE: DNA
<213> ORGANISM: Cleretum bellidiforme

<400> SEQUENCE: 17
atggactaca ccaccttggt catgattctg tctattgtgt tcttctgcta caacctgttc      60
aacttgttgt tcactagaaa gaacactaag ttgccaccag gtccaaagac tattccaatt     120
ttcggtaaca tcttcgagtt gggtaaaaag ccacatcaat cttttgctaa cttggctaag     180
attcacggtc cattgatgtc tttgaaattg ggttctgtta cgaccatcgt tgtttcatct     240
gctgaagttg ctagagaaat gttcttgaag aacgaccagt tgttgtccaa tagaactgtt     300
ccaaattctg ttaccgctgg tgatcatcat aagactacta tgtcttggtt gccagtttct     360
caaaagtggc gtaacttcag aaagattacc gctgttcatt tgttgtcccc acaaagattg     420
gattcttgtc aagctttgag acaagctaag gttaagcagt tgttcaacta catccatgaa     480
```

```
tgtgctcaaa agggtgaagc tgttgatatt ggtaaagctg cttcaccac ttccttgaac    540 ttgttgagca atttgttctt ctccgttgaa ttggccaacc acaaatcttc atcttcccaa    600
gaattcaagc agctgatctg aacattatg gaagatatcg gtaagccaaa ctacgctgat    660
tactttccag ttttgaagta cgttgatcca tccggtatta gaagaagatt ggcttctaac    720
ttcaacaagc tgatcgatgt tttccagggt ttcatcagat tgagaatgtc taccaattct    780
tcttgcggtg ctactaatcc aaatgatgtt ttggatgtcc tgctgaactt gtacaaaggt    840
gatgatttga acatggacga gatcaaccat tgttggttg atattttcga tgccggtact    900
gataccactt cttctacttt tgaatgggct atggctgaat tggttaagaa cccaaaaatg    960
atgaagaagg cccaagccga atccaacaa gttttgggta agactccat catcagagaa   1020 tccgatattc aaatatgcc atacttgcag gccatcatca aagagacttt gagattgcat   1080
ccaccaaccg ttttttttgtt gccaagaaaa gctgatgctg atgttgagtt gtatggttac   1140
gttgttccaa gaacgcccca atcttggtt aatttgtggg cttgggtag agatcctttg   1200 gtttggaaat ctcctaatgt gttcaagcca gaaaggttct tgggttccga aattgatttc   1260
aagggaagag attttggctt gttgccattt ggtgctggta agaatttg tccaggtatg   1320 aatttggcct acagaatgtt gactttgatg ttggctactc tgttgcaatc tttcgattgg   1380
aaagttgctg atggtacaaa cccacaagat atggatatgg acgaaaagtt tggtatcgcc   1440
ttgcaaaaaa ctacccccatt gcaaattatc cccgtctaca agtactga                 1488
```

<210> SEQ ID NO 18
<211> LENGTH: 495
<212> TYPE: PRT
<213> ORGANISM: Cleretum bellidiforme

<400> SEQUENCE: 18

```
Met Asp Tyr Thr Thr Leu Val Met Ile Leu Ser Ile Val Phe Phe Cys
1               5                   10                  15

Tyr Asn Leu Phe Asn Leu Leu Phe Thr Arg Lys Asn Thr Lys Leu Pro
            20                  25                  30

Pro Gly Pro Lys Thr Ile Pro Ile Phe Gly Asn Ile Phe Glu Leu Gly
        35                  40                  45

Lys Lys Pro His Gln Ser Phe Ala Asn Leu Ala Lys Ile His Gly Pro
    50                  55                  60

Leu Met Ser Leu Lys Leu Gly Ser Val Thr Thr Ile Val Val Ser Ser
65                  70                  75                  80

Ala Glu Val Ala Arg Glu Met Phe Leu Lys Asn Asp Gln Leu Leu Ser
                85                  90                  95

Asn Arg Thr Val Pro Asn Ser Val Thr Ala Gly Asp His His Lys Thr
            100                 105                 110

Thr Met Ser Trp Leu Pro Val Ser Gln Lys Trp Arg Asn Phe Arg Lys
        115                 120                 125

Ile Thr Ala Val His Leu Leu Ser Pro Gln Arg Leu Asp Ser Cys Gln
    130                 135                 140

Ala Leu Arg Gln Ala Lys Val Lys Gln Leu Phe Asn Tyr Ile His Glu
145                 150                 155                 160

Cys Ala Gln Lys Gly Glu Ala Val Asp Ile Gly Lys Ala Ala Phe Thr
                165                 170                 175

Thr Ser Leu Asn Leu Leu Ser Asn Leu Phe Phe Ser Val Glu Leu Ala
            180                 185                 190
```

```
Asn His Lys Ser Ser Ser Gln Glu Phe Lys Gln Leu Ile Trp Asn
            195                 200                 205
Ile Met Glu Asp Ile Gly Lys Pro Asn Tyr Ala Asp Tyr Phe Pro Val
    210                 215                 220
Leu Lys Tyr Val Asp Pro Ser Gly Ile Arg Arg Leu Ala Ser Asn
225                 230                 235                 240
Phe Asn Lys Leu Ile Asp Val Phe Gln Gly Phe Ile Arg Leu Arg Met
                245                 250                 255
Ser Thr Asn Ser Ser Cys Gly Ala Thr Asn Pro Asn Asp Val Leu Asp
            260                 265                 270
Val Leu Leu Asn Leu Tyr Lys Gly Asp Asp Leu Asn Met Asp Glu Ile
        275                 280                 285
Asn His Leu Leu Val Asp Ile Phe Asp Ala Gly Thr Asp Thr Thr Ser
    290                 295                 300
Ser Thr Phe Glu Trp Ala Met Ala Glu Leu Val Lys Asn Pro Lys Met
305                 310                 315                 320
Met Lys Lys Ala Gln Ala Glu Ile Gln Gln Val Leu Gly Lys Asp Ser
                325                 330                 335
Ile Ile Arg Glu Ser Asp Ile Pro Asn Met Pro Tyr Leu Gln Ala Ile
            340                 345                 350
Ile Lys Glu Thr Leu Arg Leu His Pro Pro Thr Val Phe Leu Leu Pro
        355                 360                 365
Arg Lys Ala Asp Ala Asp Val Glu Leu Tyr Gly Tyr Val Val Pro Lys
    370                 375                 380
Asn Ala Gln Ile Leu Val Asn Leu Trp Ala Leu Gly Arg Asp Pro Leu
385                 390                 395                 400
Val Trp Lys Ser Pro Asn Val Phe Lys Pro Glu Arg Phe Leu Gly Ser
                405                 410                 415
Glu Ile Asp Phe Lys Gly Arg Asp Phe Gly Leu Leu Pro Phe Gly Ala
            420                 425                 430
Gly Arg Arg Ile Cys Pro Gly Met Asn Leu Ala Tyr Arg Met Leu Thr
        435                 440                 445
Leu Met Leu Ala Thr Leu Leu Gln Ser Phe Asp Trp Lys Val Ala Asp
    450                 455                 460
Gly Thr Asn Pro Gln Asp Met Asp Met Asp Glu Lys Phe Gly Ile Ala
465                 470                 475                 480
Leu Gln Lys Thr Thr Pro Leu Gln Ile Ile Pro Val Tyr Lys Tyr
                485                 490                 495

<210> SEQ ID NO 19
<211> LENGTH: 1485
<212> TYPE: DNA
<213> ORGANISM: Ercilla volubilis

<400> SEQUENCE: 19
atggatcata ccaccttggc catgattttg tctgctattt tcctgttgta caatttggcc      60
aaggccatct tttctcattc taacacaaaa ttgccaccag gtccaaaacc agttccaatt     120
tttggtaaca tcttcgagtt gggtgaaaag ccacatagat cttttgctaa cttggctaag     180
attcacggtc cattgattac tttgaagttg ggttctgtta cgaccatcgt tgtttcatct     240
gctgaagttg ctaaagaaat gttcctgaag aacgatttgc cattggctaa tagaaacgtt     300
ccaaactctg ttactgctgg tgatcatcat aagttgacta tgtcttggtt gccagtttct     360
ccaaagtgga aaccttcag aaagattacc gctgttcatt tgttgtcccc acaaagattg     420
```

-continued

```
gattcttgtc aagctttgag acacaccaag gttaagcaat tgcatcaata cgttcaagaa    480
tgcgctaaaa gaggtgaacc agttgatatt ggtaaggctg cttttactac ctccttgaac    540
ttgttgtcta acctgttctt ctctgttgaa ttggctaacc atacctcctc atcttcccaa    600
gaattcaaag aattgatctg ggagatcatg gaagatatcg gtaagccaaa ttacgctgat    660
tacttcccaa ttttgaagtg cgttgatcca tggggtatta agaagattg gcttctaac    720
ttcgacaagt tgatcgaggt ttttcagggt ttcatcagaa agagattgtc taccggttcc    780
ttttctgcta ttactccaaa tgatgttctg gacgtgttgc tgaatctgtt gaaagaaaaa    840
gaactgaaca tgggcgaaat caaccacttg ttggttgata tttttgatgc cggtactgat    900
accacttctt ctacatttga atgggctatg gctgagttgg tcagaaatca agaaatgatg    960
aagaaggccc aagacgaaat cgaacaagtt ttgggtaaag atgccatcat ccaagaatcc   1020
gatattccaa aaatgccata cttgcaggcc attatcaaag aaaccttgag attgcatcca   1080
ccaaccgttt ttttgttgcc aagaaaggct acttctaacg ttgagttgta tggttacgtt   1140
gttccaaaga acgcccaaat cttggttaat ttgtgggcta ttggtagaga tccaaaggtt   1200
tgggataatc caaacatgtt ctctccagaa aggttcttga actccgaaat tgatgttaag   1260
ggtagagact ttggtttgtt gccttttggt gctggtagaa gaatttgtcc aggtatgaat   1320
ttggcctaca aatgttgac tttgatgttg ctactctgt tgcaatcttt cgattggaaa   1380
ttaggtgatg gtgttaaccc aaaggatttg gacatggaag aaaagtttgg tatcgccttg   1440
caaaagacta agccattgca agttattccc gtcttgaagt actga              1485
```

<210> SEQ ID NO 20
<211> LENGTH: 494
<212> TYPE: PRT
<213> ORGANISM: Ercilla volubilis

<400> SEQUENCE: 20

```
Met Asp His Thr Thr Leu Ala Met Ile Leu Ser Ala Ile Phe Leu Leu
1               5                   10                  15

Tyr Asn Leu Ala Lys Ala Ile Phe Ser His Ser Asn Thr Lys Leu Pro
            20                  25                  30

Pro Gly Pro Lys Pro Val Pro Ile Phe Gly Asn Ile Phe Glu Leu Gly
        35                  40                  45

Glu Lys Pro His Arg Ser Phe Ala Asn Leu Ala Lys Ile His Gly Pro
    50                  55                  60

Leu Ile Thr Leu Lys Leu Gly Ser Val Thr Thr Ile Val Val Ser Ser
65                  70                  75                  80

Ala Glu Val Ala Lys Glu Met Phe Leu Lys Asn Asp Leu Pro Leu Ala
                85                  90                  95

Asn Arg Asn Val Pro Asn Ser Val Thr Ala Gly Asp His His Lys Leu
            100                 105                 110

Thr Met Ser Trp Leu Pro Val Ser Pro Lys Trp Lys Thr Phe Arg Lys
        115                 120                 125

Ile Thr Ala Val His Leu Leu Ser Pro Gln Arg Leu Asp Ser Cys Gln
    130                 135                 140

Ala Leu Arg His Thr Lys Val Lys Gln Leu His Gln Tyr Val Gln Glu
145                 150                 155                 160

Cys Ala Lys Arg Gly Glu Pro Val Asp Ile Gly Lys Ala Ala Phe Thr
                165                 170                 175

Thr Ser Leu Asn Leu Leu Ser Asn Leu Phe Phe Ser Val Glu Leu Ala
            180                 185                 190
```

```
Asn His Thr Ser Ser Ser Gln Glu Phe Lys Glu Leu Ile Trp Glu
            195                 200                 205
Ile Met Glu Asp Ile Gly Lys Pro Asn Tyr Ala Asp Tyr Phe Pro Ile
210                 215                 220
Leu Lys Cys Val Asp Pro Trp Gly Ile Arg Arg Leu Ala Ser Asn
225                 230                 235                 240
Phe Asp Lys Leu Ile Glu Val Phe Gln Gly Phe Ile Arg Lys Arg Leu
                245                 250                 255
Ser Thr Gly Ser Phe Ser Ala Ile Thr Pro Asn Asp Val Leu Asp Val
            260                 265                 270
Leu Leu Asn Leu Leu Lys Glu Lys Glu Leu Asn Met Gly Glu Ile Asn
            275                 280                 285
His Leu Leu Val Asp Ile Phe Asp Ala Gly Thr Asp Thr Thr Ser Ser
290                 295                 300
Thr Phe Glu Trp Ala Met Ala Glu Leu Val Arg Asn Gln Glu Met Met
305                 310                 315                 320
Lys Lys Ala Gln Asp Glu Ile Glu Gln Val Leu Gly Lys Asp Ala Ile
                325                 330                 335
Ile Gln Glu Ser Asp Ile Pro Lys Met Pro Tyr Leu Gln Ala Ile Ile
            340                 345                 350
Lys Glu Thr Leu Arg Leu His Pro Pro Thr Val Phe Leu Leu Pro Arg
            355                 360                 365
Lys Ala Thr Ser Asn Val Glu Leu Tyr Gly Tyr Val Val Pro Lys Asn
370                 375                 380
Ala Gln Ile Leu Val Asn Leu Trp Ala Ile Gly Arg Asp Pro Lys Val
385                 390                 395                 400
Trp Asp Asn Pro Asn Met Phe Ser Pro Glu Arg Phe Leu Asn Ser Glu
                405                 410                 415
Ile Asp Val Lys Gly Arg Asp Phe Gly Leu Leu Pro Phe Gly Ala Gly
            420                 425                 430
Arg Arg Ile Cys Pro Gly Met Asn Leu Ala Tyr Arg Met Leu Thr Leu
            435                 440                 445
Met Leu Ala Thr Leu Leu Gln Ser Phe Asp Trp Lys Leu Gly Asp Gly
450                 455                 460
Val Asn Pro Lys Asp Leu Asp Met Glu Glu Lys Phe Gly Ile Ala Leu
465                 470                 475                 480
Gln Lys Thr Lys Pro Leu Gln Val Ile Pro Val Leu Lys Tyr
                485                 490
```

<210> SEQ ID NO 21
<211> LENGTH: 1494
<212> TYPE: DNA
<213> ORGANISM: Phytolacca dioica

<400> SEQUENCE: 21

```
atggatcata ccaccttggc catgattttg tctgctattt tcctgctgta caacttggtt      60
aagttggcca ttttctctca gtctaacaca aaattgccac aggtccaaa accattgcca      120 attttggta acatcttcga gttgggtgat aagccacata gatcttttgc taacttggct      180
aagattcacg gtccattgat tactttgaag ttgggttcta tcacgaccat cgttgtttca      240
tctgctgaag ttgctaaaga aatgttcttg aagaacgatc aaccactggc taatagaaac      300
gttccaaatt ctgttactgc tggtgatcat cataagttga ctatgtcttg gttgccagtt      360
tctccaaagt ggaaaacctt cagaaagatt accgctgttc atttgttgtc cccacaaaga      420
```

```
ttggatgctt gtcaagcttt gagacatacc aacgttaagc aattgcacga atacgttcaa    480
gaatgtgctc aaagaggtca accagttgat attggtaaag ctgctttcac cacttccttg    540
aacttgttgt ctaacttgtt cttctccgtt gaattggcta accatacctc ttctaactcc    600
caagaattca agaattgat ctgggacatc atggaagata tcggtaagcc aaattacgct     660
gattacttcc cagttttgaa gtgtgttgat ccatggggta ttagaagaag gttggaatct    720
aacttcgaca gttgatcga ggtctttcaa ggtttcatca gaaagagatt gtctaccggt     780
tctttctctg cttctgaaac tactccaaat gatgttttgg acgtcctgct gaatctgttc    840
aaagaaaaag aactgaacat gggcgagatc aaccatttgt tggttgatat ttttgatgcc    900
ggtactgata ccacttcttc tacttttgaa tgggctatgg ctgaattggt tagaaaccca    960
gatatgatga agaaggccca agacgaaatt gaacaagttt ggggtagaga tgccatcatc   1020
caagaatctg atattccaaa gatgccatac ttgcaggcca ttatcaaaga aactttgaga   1080
ttgcatccac caaccgtttt tttgttgcca agaaaggcta ctaccaatgt tgacttgtat   1140
ggttacgttg ttccaaagaa cgcccaaatc ttggttaatt tgtgggctat ggtagagat   1200
ccaactgttt gggataatcc aaatatgttc tctccagaga ggttcttgaa ctccgatatt   1260
gatgtaaagg gtagagactt tggtttgttg ccttttggtg ctggtagaag aatttgtcca   1320
ggtatgaatt tggcctacag aatgttgaca ttgatgttgg ctactctgtt gcaatctttc   1380
aactggaaat taggtgatgg tgttaaccca aaggatttgg atatggacga aagtttggt    1440
atcgccttgc aaaaaactaa gccattgcaa gtcattcccg tgttcaagta ctaa          1494

<210> SEQ ID NO 22
<211> LENGTH: 497
<212> TYPE: PRT
<213> ORGANISM: Phytolacca dioica

<400> SEQUENCE: 22

Met Asp His Thr Thr Leu Ala Met Ile Leu Ser Ala Ile Phe Leu Leu
1               5                   10                  15

Tyr Asn Leu Val Lys Leu Ala Ile Phe Ser Gln Ser Asn Thr Lys Leu
            20                  25                  30

Pro Pro Gly Pro Lys Pro Leu Pro Ile Phe Gly Asn Ile Phe Glu Leu
        35                  40                  45

Gly Asp Lys Pro His Arg Ser Phe Ala Asn Leu Ala Lys Ile His Gly
    50                  55                  60

Pro Leu Ile Thr Leu Lys Leu Gly Ser Ile Thr Thr Ile Val Val Ser
65                  70                  75                  80

Ser Ala Glu Val Ala Lys Glu Met Phe Leu Lys Asn Asp Gln Pro Leu
                85                  90                  95

Ala Asn Arg Asn Val Pro Asn Ser Val Thr Ala Gly Asp His His Lys
            100                 105                 110

Leu Thr Met Ser Trp Leu Pro Val Ser Pro Lys Trp Lys Thr Phe Arg
        115                 120                 125

Lys Ile Thr Ala Val His Leu Leu Ser Pro Gln Arg Leu Asp Ala Cys
    130                 135                 140

Gln Ala Leu Arg His Thr Asn Val Lys Gln Leu His Glu Tyr Val Gln
145                 150                 155                 160

Glu Cys Ala Gln Arg Gly Gln Pro Val Asp Ile Gly Lys Ala Ala Phe
                165                 170                 175

Thr Thr Ser Leu Asn Leu Leu Ser Asn Leu Phe Phe Ser Val Glu Leu
```

```
            180                 185                 190
Ala Asn His Thr Ser Asn Ser Gln Glu Phe Lys Glu Leu Ile Trp
                195                 200                 205
Asp Ile Met Glu Asp Ile Gly Lys Pro Asn Tyr Ala Asp Tyr Phe Pro
        210                 215                 220
Val Leu Lys Cys Val Asp Pro Trp Gly Ile Arg Arg Leu Glu Ser
225                 230                 235                 240
Asn Phe Asp Lys Leu Ile Glu Val Phe Gln Gly Phe Ile Arg Lys Arg
                245                 250                 255
Leu Ser Thr Gly Ser Phe Ser Ala Ser Glu Thr Thr Pro Asn Asp Val
            260                 265                 270
Leu Asp Val Leu Leu Asn Leu Phe Lys Glu Lys Glu Leu Asn Met Gly
        275                 280                 285
Glu Ile Asn His Leu Leu Val Asp Ile Phe Asp Ala Gly Thr Asp Thr
            290                 295                 300
Thr Ser Ser Thr Phe Glu Trp Ala Met Ala Glu Leu Val Arg Asn Pro
305                 310                 315                 320
Asp Met Met Lys Lys Ala Gln Asp Glu Ile Glu Gln Val Leu Gly Arg
                325                 330                 335
Asp Ala Ile Ile Gln Glu Ser Asp Ile Pro Lys Met Pro Tyr Leu Gln
            340                 345                 350
Ala Ile Ile Lys Glu Thr Leu Arg Leu His Pro Pro Thr Val Phe Leu
        355                 360                 365
Leu Pro Arg Lys Ala Thr Thr Asn Val Asp Leu Tyr Gly Tyr Val Val
370                 375                 380
Pro Lys Asn Ala Gln Ile Leu Val Asn Leu Trp Ala Ile Gly Arg Asp
                385                 390                 395                 400
Pro Thr Val Trp Asp Asn Pro Asn Met Phe Ser Pro Glu Arg Phe Leu
                    405                 410                 415
Asn Ser Asp Ile Asp Val Lys Gly Arg Asp Phe Gly Leu Leu Pro Phe
                420                 425                 430
Gly Ala Gly Arg Arg Ile Cys Pro Gly Met Asn Leu Ala Tyr Arg Met
            435                 440                 445
Leu Thr Leu Met Leu Ala Thr Leu Leu Gln Ser Phe Asn Trp Lys Leu
        450                 455                 460
Gly Asp Gly Val Asn Pro Lys Asp Leu Asp Met Asp Glu Lys Phe Gly
465                 470                 475                 480
Ile Ala Leu Gln Lys Thr Lys Pro Leu Gln Val Ile Pro Val Phe Lys
                485                 490                 495
Tyr

<210> SEQ ID NO 23
<211> LENGTH: 1512
<212> TYPE: DNA
<213> ORGANISM: Acleisanthes obtuse

<400> SEQUENCE: 23
atggaaaaca ccaccttggg tgttattctg gccattattt tcttgacctt ccacgtcatg      60
aagctgttgt tgtcatctaa caaagctaaa ttgccaccag gtccaaaacc attgccaatt     120
attggtaaca tcttggagtt gggtgataag ccacatagat cttttgctaa cttggctaag    180
attcacggtc cattgattac tttgaagttg ggttctgtta cgactatcgt tgtctcttca     240
tctgaagttg ccaaagaaat gttcttgaag aacgatcaag ctttggccaa cagaactatt    300
```

-continued

```
ccagattctg ttagagctgg taaccacgat aagttgtcta tgtcttggtt gccagtttct    360
ccaaaatggc gtaacttgag aaagatttct gccgttcaac tgctgtcatc tcaaagattg    420
gatgcttctc aagctcacag acaagttaag gttgaacagt tgatcgaata cgtcaaagag    480
tgctctaaga ttggtcaatg cgttgatatt ggtagagttg ctttcaccac ttccttgaac    540
ttgttgtcta acaccttctt cagcaaagaa ttggcctctt cgattctaa caacgcccaa     600 gaattcaagc aattgatgtg gtgcattatg aagaaatcg gtagaccaaa ttacgccgat     660
tactttccaa ttttgggtta cgttgatcca ttcggtgtta aagaagatt gtccagatac     720 ttcgaccagt tgattgaagt gttccaacag atcattagag agaggttgtc taaggataac     780
aagatcgtcg ataacaacaa cgatgttttg gctactttgc tgcacttgta caaacagaac    840
gaattgtcta tggacgagat caaccatttg ttggttgata ttttcgatgc cggtactgat    900
acaactgctt ctactttgga tgggctatg tccgaattga ttaagaaccc acatattatg     960
attaaggccc aagccgaagt tagacaagct acttcttcta gaggtggtgc tactgttgtt   1020
gatgttcaag aatccgatat caacaacttg ccttacattc aggccatcat caaagaatcc   1080
ttgagattgc atccaccaac cgttttttg ttgccaagaa aagctgatgt tgacgttcag    1140
ttgtacggtt atttggttcc aaagaatgcc aagttttgg ttaacttgtg ggctataggt    1200
agagatccaa atgtttggcc agatccagaa gttttttagac cagaaagatt cttggattgc   1260
gaagttgatg ttaagggtag agattttgag ttgttgccat tggtgctgg tagaagaatt    1320 tgtcctggtt tgtctttggc ttacaggatg ttgaatctga tgttggctaa tctggttcat    1380
tccttcgatt ggaaattgcc aaacgtcgaa acaagtctg gttctgatcc agatgaattg    1440
gatatggacg aaaagttcgg tatcaccttg caaaaagtta agccattgca aatcatcccc    1500
atgtccagat ga                                                        1512

<210> SEQ ID NO 24
<211> LENGTH: 503
<212> TYPE: PRT
<213> ORGANISM: Acleisanthes obtuse

<400> SEQUENCE: 24

Met Glu Asn Thr Thr Leu Gly Val Ile Leu Ala Ile Ile Phe Leu Thr
1               5                   10                  15

Phe His Val Met Lys Leu Leu Ser Ser Asn Lys Ala Lys Leu Pro
            20                  25                  30

Pro Gly Pro Lys Pro Leu Pro Ile Ile Gly Asn Ile Leu Glu Leu Gly
        35                  40                  45

Asp Lys Pro His Arg Ser Phe Ala Asn Leu Ala Lys Ile His Gly Pro
    50                  55                  60

Leu Ile Thr Leu Lys Leu Gly Ser Val Thr Thr Ile Val Val Ser Ser
65                  70                  75                  80

Ser Glu Val Ala Lys Glu Met Phe Leu Lys Asn Asp Gln Ala Leu Ala
                85                  90                  95

Asn Arg Thr Ile Pro Asp Ser Val Arg Ala Gly Asn His Asp Lys Leu
            100                 105                 110

Ser Met Ser Trp Leu Pro Val Ser Pro Lys Trp Arg Asn Leu Arg Lys
        115                 120                 125

Ile Ser Ala Val Gln Leu Leu Ser Ser Gln Arg Leu Asp Ala Ser Gln
    130                 135                 140

Ala His Arg Gln Val Lys Val Glu Gln Leu Ile Glu Tyr Val Lys Glu
145                 150                 155                 160
```

Cys Ser Lys Ile Gly Gln Cys Val Asp Ile Gly Arg Val Ala Phe Thr
            165                 170                 175

Thr Ser Leu Asn Leu Leu Ser Asn Thr Phe Phe Ser Lys Glu Leu Ala
            180                 185                 190

Ser Phe Asp Ser Asn Asn Ala Gln Glu Phe Lys Gln Leu Met Trp Cys
            195                 200                 205

Ile Met Glu Glu Ile Gly Arg Pro Asn Tyr Ala Asp Tyr Phe Pro Ile
            210                 215                 220

Leu Gly Tyr Val Asp Pro Phe Gly Val Arg Arg Leu Ser Arg Tyr
225                 230                 235                 240

Phe Asp Gln Leu Ile Glu Val Phe Gln Gln Ile Ile Arg Glu Arg Leu
            245                 250                 255

Ser Lys Asp Asn Lys Ile Val Asp Asn Asn Asp Val Leu Ala Thr
            260                 265                 270

Leu Leu His Leu Tyr Lys Gln Asn Glu Leu Ser Met Asp Glu Ile Asn
            275                 280                 285

His Leu Leu Val Asp Ile Phe Asp Ala Gly Thr Asp Thr Thr Ala Ser
            290                 295                 300

Thr Leu Glu Trp Ala Met Ser Glu Leu Ile Lys Asn Pro His Ile Met
305                 310                 315                 320

Ile Lys Ala Gln Ala Glu Val Arg Gln Ala Thr Ser Ser Arg Gly Gly
            325                 330                 335

Ala Thr Val Val Asp Val Gln Glu Ser Asp Ile Asn Asn Leu Pro Tyr
            340                 345                 350

Ile Gln Ala Ile Ile Lys Glu Ser Leu Arg Leu His Pro Pro Thr Val
            355                 360                 365

Phe Leu Leu Pro Arg Lys Ala Asp Val Asp Val Gln Leu Tyr Gly Tyr
            370                 375                 380

Leu Val Pro Lys Asn Ala Gln Val Leu Val Asn Leu Trp Ala Ile Gly
385                 390                 395                 400

Arg Asp Pro Asn Val Trp Pro Asp Pro Glu Val Phe Arg Pro Glu Arg
            405                 410                 415

Phe Leu Asp Cys Glu Val Asp Val Lys Gly Arg Asp Phe Glu Leu Leu
            420                 425                 430

Pro Phe Gly Ala Gly Arg Arg Ile Cys Pro Gly Leu Ser Leu Ala Tyr
            435                 440                 445

Arg Met Leu Asn Leu Met Leu Ala Asn Leu Val His Ser Phe Asp Trp
            450                 455                 460

Lys Leu Pro Asn Val Glu Asn Lys Ser Gly Ser Asp Pro Asp Glu Leu
465                 470                 475                 480

Asp Met Asp Glu Lys Phe Gly Ile Thr Leu Gln Lys Val Lys Pro Leu
            485                 490                 495

Gln Ile Ile Pro Met Ser Arg
            500

<210> SEQ ID NO 25
<211> LENGTH: 1512
<212> TYPE: DNA
<213> ORGANISM: Mirabilis multiflora

<400> SEQUENCE: 25
atggaaaaca ccatgttggg tgttattctg gctactattt tcttgacctt ccacatcatg      60
aagatgttct tgtctccatc taaagctaaa ttgccaccag gtccaagacc attgccaatt     120

-continued

| | |
|---|---|
| attggtaaca ttttggagtt gggtgataag ccacatagat cttttgctaa cttggctaag | 180 |
| attcacggtc cattggttac tttgaaattg ggttctgtta cgactatcgt cgtgtcatct | 240 |
| tctgaagttg ctaaagaaat gttcctgaag aacgatcaac cattggccaa cagaactatt | 300 |
| ccagattctg ttagagctgg taaccacgat aagttgtcta tgtcttggtt gccagtttca | 360 |
| ccaaaatggc gtaacttgag aaagatttct gctgtccaac tgttgtctac ccaaagattg | 420 |
| gatgcttctc aagctcatag acaagccaag attcaacaat tgatcgagta catcaagaag | 480 |
| tgctccaaga ttggtcaata cgttgatatt ggtcaagttg ccttcaccac ttctttgaac | 540 |
| ttgttgtcta caccttcttt cagcaaagaa ttggcctctt tcgattctaa caacgcccaa | 600 |
| gagtttaagc aattgatgtg gtgcattatg gaagaaatcg gtagaccaaa ttacgccgat | 660 |
| tactttccta ttttgggtta cgttgatcca ttcggtgcta agaagatt gtctagatac | 720 |
| ttcgaccagt tgatcgaagt tttccaagtc atcattagag aaaggttgac ccacgataac | 780 |
| aacatcgttg gtaacaacaa cgatatttg gctaccttgc tggacttgta caaacagaat | 840 |
| gaattgtcca tggatgagat caaccacttg ttggttgata ttttcgatgc tggtactgat | 900 |
| accactgctt ctactttgga atgggctatg tctgaattga tcaagaaccc acatattatg | 960 |
| gtcaaggccc aagaagaagt tagacaagct actatgtcta gaggtggtgc tactgttgct | 1020 |
| gaaattcaag aatccgatat caacaacttg ccctacattc agtccattgt caaagaaacc | 1080 |
| ttgagattgc atccaccaac tgttttttg ttgccaagaa aggctgaagt tgatgttcag | 1140 |
| ttgttcggtt atgttgttcc aaagaacgct caagttttgg ttaacttgtg ggctattggt | 1200 |
| agagatccaa atgtttggcc agatccagaa gtttttaagc cagaaagatt catggattgc | 1260 |
| gaaatcgatg ttaagggtag agattttgag ttgttgccat tggtgctgg tagaagaatt | 1320 |
| tgtccaggtt tgtctttggc ttacaggatg ttgaatttga tgttggctaa catggtccat | 1380 |
| tccttcgaat ggaaattgcc aggtgttgaa aatggtttcg gttccgaaat ggattctttg | 1440 |
| gatatggacg aaaagttcgg tatcaccttg caaaaagttc agccattgaa ggttatccca | 1500 |
| gtctctagat aa | 1512 |

<210> SEQ ID NO 26
<211> LENGTH: 503
<212> TYPE: PRT
<213> ORGANISM: Mirabilis multiflora

<400> SEQUENCE: 26

Met Glu Asn Thr Met Leu Gly Val Ile Leu Ala Thr Ile Phe Leu Thr
1               5                   10                  15

Phe His Ile Met Lys Met Phe Leu Ser Pro Ser Lys Ala Lys Leu Pro
            20                  25                  30

Pro Gly Pro Arg Pro Leu Pro Ile Gly Asn Ile Leu Glu Leu Gly
        35                  40                  45

Asp Lys Pro His Arg Ser Phe Ala Asn Leu Ala Lys Ile His Gly Pro
    50                  55                  60

Leu Val Thr Leu Lys Leu Gly Ser Val Thr Thr Ile Val Val Ser Ser
65                  70                  75                  80

Ser Glu Val Ala Lys Glu Met Phe Leu Lys Asn Asp Gln Pro Leu Ala
                85                  90                  95

Asn Arg Thr Ile Pro Asp Ser Val Arg Ala Gly Asn His Asp Lys Leu
            100                 105                 110

Ser Met Ser Trp Leu Pro Val Ser Pro Lys Trp Arg Asn Leu Arg Lys
        115                 120                 125

-continued

Ile Ser Ala Val Gln Leu Leu Ser Thr Gln Arg Leu Asp Ala Ser Gln
    130                 135                 140

Ala His Arg Gln Ala Lys Ile Gln Gln Leu Ile Glu Tyr Ile Lys Lys
145                 150                 155                 160

Cys Ser Lys Ile Gly Gln Tyr Val Asp Ile Gly Gln Val Ala Phe Thr
                165                 170                 175

Thr Ser Leu Asn Leu Leu Ser Asn Thr Phe Phe Ser Lys Glu Leu Ala
            180                 185                 190

Ser Phe Asp Ser Asn Asn Ala Gln Glu Phe Lys Gln Leu Met Trp Cys
        195                 200                 205

Ile Met Glu Glu Ile Gly Arg Pro Asn Tyr Ala Asp Tyr Phe Pro Ile
    210                 215                 220

Leu Gly Tyr Val Asp Pro Phe Gly Ala Arg Arg Leu Ser Arg Tyr
225                 230                 235                 240

Phe Asp Gln Leu Ile Glu Val Phe Gln Val Ile Ile Arg Glu Arg Leu
                245                 250                 255

Thr His Asp Asn Asn Ile Val Gly Asn Asn Asp Ile Leu Ala Thr
            260                 265                 270

Leu Leu Asp Leu Tyr Lys Gln Asn Glu Leu Ser Met Asp Glu Ile Asn
        275                 280                 285

His Leu Leu Val Asp Ile Phe Asp Ala Gly Thr Asp Thr Thr Ala Ser
    290                 295                 300

Thr Leu Glu Trp Ala Met Ser Glu Leu Ile Lys Asn Pro His Ile Met
305                 310                 315                 320

Val Lys Ala Gln Glu Glu Val Arg Gln Ala Thr Met Ser Arg Gly Gly
                325                 330                 335

Ala Thr Val Ala Glu Ile Gln Glu Ser Asp Ile Asn Asn Leu Pro Tyr
            340                 345                 350

Ile Gln Ser Ile Val Lys Glu Thr Leu Arg Leu His Pro Pro Thr Val
        355                 360                 365

Phe Leu Leu Pro Arg Lys Ala Glu Val Asp Val Gln Leu Phe Gly Tyr
    370                 375                 380

Val Val Pro Lys Asn Ala Gln Val Leu Val Asn Leu Trp Ala Ile Gly
385                 390                 395                 400

Arg Asp Pro Asn Val Trp Pro Asp Pro Glu Val Phe Lys Pro Glu Arg
                405                 410                 415

Phe Met Asp Cys Glu Ile Asp Val Lys Gly Arg Asp Phe Glu Leu Leu
            420                 425                 430

Pro Phe Gly Ala Gly Arg Arg Ile Cys Pro Gly Leu Ser Leu Ala Tyr
        435                 440                 445

Arg Met Leu Asn Leu Met Leu Ala Asn Met Val His Ser Phe Glu Trp
    450                 455                 460

Lys Leu Pro Gly Val Glu Asn Gly Phe Gly Ser Glu Met Asp Ser Leu
465                 470                 475                 480

Asp Met Asp Glu Lys Phe Gly Ile Thr Leu Gln Lys Val Gln Pro Leu
                485                 490                 495

Lys Val Ile Pro Val Ser Arg
            500

<210> SEQ ID NO 27
<211> LENGTH: 1485
<212> TYPE: DNA
<213> ORGANISM: Acleisanthes obtuse

<400> SEQUENCE: 27

```
atggaccaaa ctaccttggc catgttgttg tctgcattat acctgctgta caacctgtac      60
aaggttatct tcactcagtc caattctaaa ttgccaccag gtccaaaacc attgccaatt     120
ttgggtaaca ttttcgaggt tggtaacaag ccacatagag cttttgctaa cttggctaag     180
attcacggtc cattgattac tttgaagttg ggttctgtta cgaccatcgt tgtttcttca     240
gctaaagttg ccgaagagat gttcttgaag aatgatttgc cattggccaa cagaaacgtt     300
ccaaattctg ttactgctgg tgatcatcat aagttgacta tgtcttggtt gccagtttct     360
ccaaagtgga aaaccttcag aaagattacc gctgttcatt tgttgtcccc acaaagattg     420
gatgcttgtc aagctttgag acatgctaag gttaagcaat gcacgaata cgttcaagat      480
tgtgctaaaa agggtcaagc cgttgatatt ggtaaagctg cttttactac ctccttgaac     540
ttgctgtcta acttgttctt ctctgttgaa ttggctcaac acacctcttc atcttcccaa     600
catttcaaag aattgatctg ggacatcatg gaagatatcg gtaagccaaa ttacgctgat     660
tatttcccag ctttgaagtg tgttgatcca tggggtatta agaagaagatt ggctgctaat    720
ttcgaaaggt tgatcgatgt tttccagggt ttcattagac agaggttgtc cattaactct     780
tctactgtta cttctgcctc tgatgtttg gatgtcttgc tgaacttgta caagaaaaaa      840
gaactgaaca tgggcgagat caaccatttg ttggttgata ttttgatgc cggtactgat      900
accacttctt ctacatttga atgggctatg gctgaattgg ttagacatcc agaaattatg     960
aagaaggccc aagacgaaat cgaacaagtt ttaggtaagg atgccattat ccaagaagcc    1020
gatattccaa aaatgccata cttgcaagcc atcatcaaag aaaccttgag attgcatcca    1080
ccaaccgttt ttttgttgcc aagaaaggct actaccaacg tcgaattata tggttacgtt    1140
gttccaaaga acgcccaaat cttggttaat ttgtgggcta ttggtagaga tccattggtt    1200
tgggataatc caaacaagtt ctctccagaa aggttcttga actccgatat tgatgttaag    1260
ggtagagact ttggtttgtt gccttttggt gctggtagaa gaatttgtcc aggtatgaat    1320
ttggcctaca gaatcttgac tttgatgttg gcaactctgt tgcaatcttt cgaatggatg    1380
gttgaaaatg gtgaaaaccc tgaagatttg gacatggacg aaaaatttgg tatcgccttg    1440
caaaagacta agccattgga aattatccca gtcatcaagc actga                    1485
```

<210> SEQ ID NO 28
<211> LENGTH: 434
<212> TYPE: PRT
<213> ORGANISM: Acleisanthes obtuse

<400> SEQUENCE: 28

```
Ile His Gly Pro Leu Ile Thr Leu Lys Leu Gly Ser Val Thr Thr Ile
1               5                   10                  15

Val Val Ser Ser Ala Lys Val Ala Glu Glu Met Phe Leu Lys Asn Asp
            20                  25                  30

Leu Pro Leu Ala Asn Arg Asn Val Pro Asn Ser Val Thr Ala Gly Asp
        35                  40                  45

His His Lys Leu Thr Met Ser Trp Leu Pro Val Ser Pro Lys Trp Lys
    50                  55                  60

Thr Phe Arg Lys Ile Thr Ala Val His Leu Leu Ser Pro Gln Arg Leu
65                  70                  75                  80

Asp Ala Cys Gln Ala Leu Arg His Ala Lys Val Lys Gln Leu His Glu
                85                  90                  95

Tyr Val Gln Asp Cys Ala Lys Lys Gly Gln Ala Val Asp Ile Gly Lys
```

```
               100                 105                 110
Ala Ala Phe Thr Thr Ser Leu Asn Leu Leu Ser Asn Leu Phe Phe Ser
            115                 120                 125

Val Glu Leu Ala Gln His Thr Ser Ser Ser Gln His Phe Lys Glu
130                 135                 140

Leu Ile Trp Asp Ile Met Glu Asp Ile Gly Lys Pro Asn Tyr Ala Asp
145                 150                 155                 160

Tyr Phe Pro Ala Leu Lys Cys Val Asp Pro Trp Gly Ile Arg Arg Arg
                165                 170                 175

Leu Ala Ala Asn Phe Glu Arg Leu Ile Asp Val Phe Gln Gly Phe Ile
            180                 185                 190

Arg Gln Arg Leu Ser Ile Asn Ser Ser Thr Val Thr Ser Ala Ser Asp
        195                 200                 205

Val Leu Asp Val Leu Leu Asn Leu Tyr Lys Glu Lys Glu Leu Asn Met
    210                 215                 220

Gly Glu Ile Asn His Leu Leu Val Asp Ile Phe Asp Ala Gly Thr Asp
225                 230                 235                 240

Thr Thr Ser Ser Thr Phe Glu Trp Ala Met Ala Glu Leu Val Arg His
                245                 250                 255

Pro Glu Ile Met Lys Lys Ala Gln Asp Glu Ile Glu Gln Val Leu Gly
            260                 265                 270

Lys Asp Ala Ile Ile Gln Glu Ala Asp Ile Pro Lys Met Pro Tyr Leu
        275                 280                 285

Gln Ala Ile Ile Lys Glu Thr Leu Arg Leu His Pro Pro Thr Val Phe
    290                 295                 300

Leu Leu Pro Arg Lys Ala Thr Thr Asn Val Glu Leu Tyr Gly Tyr Val
305                 310                 315                 320

Val Pro Lys Asn Ala Gln Ile Leu Val Asn Leu Trp Ala Ile Gly Arg
                325                 330                 335

Asp Pro Leu Val Trp Asp Asn Pro Asn Lys Phe Ser Pro Glu Arg Phe
            340                 345                 350

Leu Asn Ser Asp Ile Asp Val Lys Gly Arg Asp Phe Gly Leu Leu Pro
        355                 360                 365

Phe Gly Ala Gly Arg Arg Ile Cys Pro Gly Met Asn Leu Ala Tyr Arg
    370                 375                 380

Ile Leu Thr Leu Met Leu Ala Thr Leu Leu Gln Ser Phe Glu Trp Met
385                 390                 395                 400

Val Glu Asn Gly Glu Asn Pro Glu Asp Leu Asp Met Asp Glu Lys Phe
                405                 410                 415

Gly Ile Ala Leu Gln Lys Thr Lys Pro Leu Glu Ile Ile Pro Val Ile
            420                 425                 430

Lys His

<210> SEQ ID NO 29
<211> LENGTH: 1488
<212> TYPE: DNA
<213> ORGANISM: Abronia nealleyi

<400> SEQUENCE: 29
atggactact tgaccatcgt catgttggtg tctatcgttt tcttcctgta ctccttgttg      60
aagatgatgt tcatcactca ttccaacgct caattgccac caggtccaaa acctatgcca     120
ttgattggta acattttgga gattggtgaa aagccacata gatcctttgc taacttggct     180
aaatctcatg gtccattgat gtctttgaga ttgggtagag ttactaccat cgttgtttca     240
```

```
tctgctgaag ttgccaaaga aatgttcttg aagaacgacc aatctttgtc gatagatgt     300
gttccaaatt ctgttactgc tggtgatcat cataagttga ctatgtcttg gttgccagtt    360
tcaccaaagt ggaagaactt cagaaagatt accgctgttc atttgttgtc tccacaaaga    420
ctagatgctt gtcatgcttt gagacatgct aaagttaagc agttgtacga gtacattcaa    480
gaatgcgcta ttaagggtga agccgttgat attggtaaag ctgcttttac tacctccttg    540
aacttgctgt ctaacttgtt cttctctgtt gaattggctc atcatacctc taacacctct    600
caagaattca agcaattgat ctgggacatc atggaagata tcggtaagcc aaattacgct    660
gattacttcc cactgttgaa atacgttgat ccattgggta tcagacatag attggctgct    720
aatttcgata agctgatcga cgttttccag tcctttatta gaaagaggct gctgtcctct    780
tattcttctg ctacttcttt gaacgatgtc ttggacgttt tgttgaagct gtacaaagaa    840
aaggctttga acatgggtga atcaaccac ttgttggttg atattttcga tgctggtact     900
gataccacct ctaatacttt tgaatgggct atggccgaat tgatcagaca tccaattatg    960
atgagaaggg cccaaactga aattgctttg gttttgggta agacccaac catcaaagaa    1020
gctgacgttg ctaatatgcc atacttgcaa gccattatca agaaaccttt gagattgcat    1080
ccaccaaccg tttttttgtt gccaagaaag gctattaccg acgttaagtt gtatggttac    1140
gttgtcccaa agaactccca aatcttggtt aatttgtggg ccattggtag agatccaaag    1200
gtttggaaca atccaaacga attcatgcca gacagattct gaactccga tattgatgtt    1260
aagggtagag actttggttt gttgccttttt ggtgctggta agaatttg tccaggtatg    1320
aatttggcct acagaatgtt gactttgatg ttggctactc tgttgcaatc tttcgattgg    1380
aaattgccac atggtattac ccctaaggat ttggatatgg acgaaaagtt cggtatctcc    1440
ttgcaaaaaa ctaagccatt gcagttgatc cccatcttga agtactaa                 1488
```

<210> SEQ ID NO 30
<211> LENGTH: 495
<212> TYPE: PRT
<213> ORGANISM: Abronia nealleyi

<400> SEQUENCE: 30

```
Met Asp Tyr Leu Thr Ile Val Met Leu Val Ser Ile Val Phe Phe Leu
1               5                   10                  15

Tyr Ser Leu Leu Lys Met Met Phe Ile Thr His Ser Asn Ala Gln Leu
            20                  25                  30

Pro Pro Gly Pro Lys Pro Met Pro Leu Ile Gly Asn Ile Leu Glu Ile
        35                  40                  45

Gly Glu Lys Pro His Arg Ser Phe Ala Asn Leu Ala Lys Ser His Gly
    50                  55                  60

Pro Leu Met Ser Leu Arg Leu Gly Arg Val Thr Thr Ile Val Val Ser
65                  70                  75                  80

Ser Ala Glu Val Ala Lys Glu Met Phe Leu Lys Asn Asp Gln Ser Leu
                85                  90                  95

Cys Asp Arg Cys Val Pro Asn Ser Val Thr Ala Gly Asp His His Lys
            100                 105                 110

Leu Thr Met Ser Trp Leu Pro Val Ser Pro Lys Trp Lys Asn Phe Arg
        115                 120                 125

Lys Ile Thr Ala Val His Leu Leu Ser Pro Gln Arg Leu Asp Ala Cys
    130                 135                 140

His Ala Leu Arg His Ala Lys Val Lys Gln Leu Tyr Glu Tyr Ile Gln
```

```
                    145                 150                 155                 160
            Glu Cys Ala Ile Lys Gly Glu Ala Val Asp Ile Gly Lys Ala Ala Phe
                            165                 170                 175

Thr Thr Ser Leu Asn Leu Leu Ser Asn Leu Phe Phe Ser Val Glu Leu
                            180                 185                 190

Ala His His Thr Ser Asn Thr Ser Gln Glu Phe Lys Gln Leu Ile Trp
                            195                 200                 205

Asp Ile Met Glu Asp Ile Gly Lys Pro Asn Tyr Ala Asp Tyr Phe Pro
                210                 215                 220

Leu Leu Lys Tyr Val Asp Pro Leu Gly Ile Arg His Arg Leu Ala Ala
            225                 230                 235                 240

Asn Phe Asp Lys Leu Ile Asp Val Phe Gln Ser Phe Ile Arg Lys Arg
                            245                 250                 255

Leu Leu Ser Ser Tyr Ser Ser Ala Thr Ser Leu Asn Asp Val Leu Asp
                            260                 265                 270

Val Leu Leu Lys Leu Tyr Lys Glu Lys Ala Leu Asn Met Gly Glu Ile
                            275                 280                 285

Asn His Leu Leu Val Asp Ile Phe Asp Ala Gly Thr Asp Thr Thr Ser
                290                 295                 300

Asn Thr Phe Glu Trp Ala Met Ala Glu Leu Ile Arg His Pro Ile Met
            305                 310                 315                 320

Met Arg Arg Ala Gln Thr Glu Ile Ala Leu Val Leu Gly Lys Asp Pro
                            325                 330                 335

Thr Ile Lys Glu Ala Asp Val Ala Asn Met Pro Tyr Leu Gln Ala Ile
                            340                 345                 350

Ile Lys Glu Thr Leu Arg Leu His Pro Pro Thr Val Phe Leu Leu Pro
                            355                 360                 365

Arg Lys Ala Ile Thr Asp Val Lys Leu Tyr Gly Tyr Val Val Pro Lys
                            370                 375                 380

Asn Ser Gln Ile Leu Val Asn Leu Trp Ala Ile Gly Arg Asp Pro Lys
            385                 390                 395                 400

Val Trp Asn Asn Pro Asn Glu Phe Met Pro Asp Arg Phe Leu Asn Ser
                            405                 410                 415

Asp Ile Asp Val Lys Gly Arg Asp Phe Gly Leu Leu Pro Phe Gly Ala
                            420                 425                 430

Gly Arg Arg Ile Cys Pro Gly Met Asn Leu Ala Tyr Arg Met Leu Thr
                            435                 440                 445

Leu Met Leu Ala Thr Leu Leu Gln Ser Phe Asp Trp Lys Leu Pro His
            450                 455                 460

Gly Ile Thr Pro Lys Asp Leu Asp Met Asp Glu Lys Phe Gly Ile Ser
            465                 470                 475                 480

Leu Gln Lys Thr Lys Pro Leu Gln Leu Ile Pro Ile Leu Lys Tyr
                            485                 490                 495

<210> SEQ ID NO 31
<211> LENGTH: 1491
<212> TYPE: DNA
<213> ORGANISM: Phytolacca Americana

<400> SEQUENCE: 31
atggatcata ccaccttggc catgatcttg tctgttattt tcctgctgta caacttggtt      60
aaggccatct tttctcaatc caacacaaaa ttgccaccag gtccaaaacc agttccaatt     120
tttggtaaca tcttcgagtt gggtgataag ccacatagat cttttgctaa cttggctaag     180
```

```
attcacggtc cattgattac tttgaagttg ggttctgtta cgaccatcgt tgtttcatct    240
gctgaagttg ctaaagaaat gttcttgacc aacgatcagt tgctggctaa tagaaacgtt    300
ccaaattctg ttactgctgg tgatcatcat aagttgacta tgtcttggtt gccagtttct    360
ccaaagtgga aaaccttcag aaagattacc gctgttcatt tgttgtcccc acaaagattg    420
gatgcttgtc aagctttgag acataccaaa gttaagcagt tgtacgaata cgttcaagaa    480
tgtgctaaaa gaggtgaagc cgttgatatt ggtaaagctg cttttactac ctccttgaac    540
ttgctgtcta acttgttctt ctctgttgaa ttggctaacc acacctcttc atcttcccaa    600
gaattcaaag aattgatctg ggacatcatg aagatatcg gtaagccaaa ttacgctgat     660
tacttcccag ttttgaagtg tgttgatcca tggggtatta aagaaggtt ggaatctaac     720
ttcgacaagt tgatcgaggt gttccagtct ttcattagaa agagattgtc taccgaacca    780
ttttctgcct ctgctaaaac tccaaatgat gttttggacg tgctgctgaa cttgttgaaa    840
gaagaggaat tgaacatggg tgagatcaac catttgttgg ttgatatttt cgatgccggt    900
actgatacca cttcttctac atttgaatgg gctatggctg aattggttag aaacccagaa    960
atgatgaaga aggcccaaga cgaaattgaa caagttttgg gtaaagacgc catcatccaa   1020
gaatctgata ttccaaaaat gccatacttg caggccatta tcaaagaaac cttgagattg   1080
catccaccaa ccgttttttt gttgccaaga aaagcctctt ctaacgttga gttgtatggt   1140
tacgttgttc aaagaacgc ccaaatcttg gttaatttgt gggctattgg tagagatcca    1200
actgtttggg ataatccaaa tatgttctct ccagagaggt tcttgaactc cgatattgat   1260
gttaagggta gagactttgg tttgttgcct tttggtgctg gtagaagaat ttgtccaggt   1320
atgaatttgg cctacagaat gttgactttg atgttggcta ctctgttgca atctttcgat   1380
tggaaattag gtgatggtgt taacccaaag gatttggata tggacgaaaa gtttggtatc   1440
gccttgcaaa aaactaagcc attgcaagtc attcccgtct gaagtacta a              1491
```

<210> SEQ ID NO 32
<211> LENGTH: 496
<212> TYPE: PRT
<213> ORGANISM: Phytolacca Americana

<400> SEQUENCE: 32

```
Met Asp His Thr Thr Leu Ala Met Ile Leu Ser Val Ile Phe Leu Leu
1               5                   10                  15

Tyr Asn Leu Val Lys Ala Ile Phe Ser Gln Ser Asn Thr Lys Leu Pro
            20                  25                  30

Pro Gly Pro Lys Pro Val Pro Ile Phe Gly Asn Ile Phe Glu Leu Gly
        35                  40                  45

Asp Lys Pro His Arg Ser Phe Ala Asn Leu Ala Lys Ile His Gly Pro
    50                  55                  60

Leu Ile Thr Leu Lys Leu Gly Ser Val Thr Thr Ile Val Val Ser Ser
65                  70                  75                  80

Ala Glu Val Ala Lys Glu Met Phe Leu Thr Asn Asp Gln Leu Leu Ala
                85                  90                  95

Asn Arg Asn Val Pro Asn Ser Val Thr Ala Gly Asp His His Lys Leu
            100                 105                 110

Thr Met Ser Trp Leu Pro Val Ser Pro Lys Trp Lys Thr Phe Arg Lys
        115                 120                 125

Ile Thr Ala Val His Leu Leu Ser Pro Gln Arg Leu Asp Ala Cys Gln
    130                 135                 140
```

-continued

Ala Leu Arg His Thr Lys Val Lys Gln Leu Tyr Glu Tyr Val Gln Glu
145                 150                 155                 160

Cys Ala Lys Arg Gly Glu Ala Val Asp Ile Gly Lys Ala Ala Phe Thr
                165                 170                 175

Thr Ser Leu Asn Leu Leu Ser Asn Leu Phe Phe Ser Val Glu Leu Ala
            180                 185                 190

Asn His Thr Ser Ser Ser Gln Glu Phe Lys Glu Leu Ile Trp Asp
        195                 200                 205

Ile Met Glu Asp Ile Gly Lys Pro Asn Tyr Ala Asp Tyr Phe Pro Val
210                 215                 220

Leu Lys Cys Val Asp Pro Trp Gly Ile Arg Arg Leu Glu Ser Asn
225                 230                 235                 240

Phe Asp Lys Leu Ile Glu Val Phe Gln Ser Phe Ile Arg Lys Arg Leu
                245                 250                 255

Ser Thr Glu Pro Phe Ser Ala Ser Ala Lys Thr Pro Asn Asp Val Leu
            260                 265                 270

Asp Val Leu Leu Asn Leu Leu Lys Glu Glu Leu Asn Met Gly Glu
        275                 280                 285

Ile Asn His Leu Leu Val Asp Ile Phe Asp Ala Gly Thr Asp Thr Thr
290                 295                 300

Ser Ser Thr Phe Glu Trp Ala Met Ala Glu Leu Val Arg Asn Pro Glu
305                 310                 315                 320

Met Met Lys Lys Ala Gln Asp Glu Ile Glu Gln Val Leu Gly Lys Asp
                325                 330                 335

Ala Ile Ile Gln Glu Ser Asp Ile Pro Lys Met Pro Tyr Leu Gln Ala
            340                 345                 350

Ile Ile Lys Glu Thr Leu Arg Leu His Pro Pro Thr Val Phe Leu Leu
        355                 360                 365

Pro Arg Lys Ala Ser Ser Asn Val Glu Leu Tyr Gly Tyr Val Val Pro
370                 375                 380

Lys Asn Ala Gln Ile Leu Val Asn Leu Trp Ala Ile Gly Arg Asp Pro
385                 390                 395                 400

Thr Val Trp Asp Asn Pro Asn Met Phe Ser Pro Glu Arg Phe Leu Asn
                405                 410                 415

Ser Asp Ile Asp Val Lys Gly Arg Asp Phe Gly Leu Leu Pro Phe Gly
            420                 425                 430

Ala Gly Arg Arg Ile Cys Pro Gly Met Asn Leu Ala Tyr Arg Met Leu
        435                 440                 445

Thr Leu Met Leu Ala Thr Leu Leu Gln Ser Phe Asp Trp Lys Leu Gly
450                 455                 460

Asp Gly Val Asn Pro Lys Asp Leu Asp Met Asp Glu Lys Phe Gly Ile
465                 470                 475                 480

Ala Leu Gln Lys Thr Lys Pro Leu Gln Val Ile Pro Val Leu Lys Tyr
                485                 490                 495

<210> SEQ ID NO 33
<211> LENGTH: 1500
<212> TYPE: DNA
<213> ORGANISM: Chenopodium quinoa

<400> SEQUENCE: 33
atggaacata ccaccttggc cttgatcttg tccattttgt tcatttgctt ccacttggtc    60
aggtcctttg tttctcattc tactaagtct aacaagttgc caccaggtcc aaaaagaatg   120 ccaatttttcg gtaacatctt ggacttgggt gaaaagccac atagatcttt tgctaacttg   180

```
gctaagattc acggtccatt ggtttctttta caattgggtt ctatcacgac catcatcgtt    240
tcttcagctg atgttgctaa agaaatgttc ttgaagaacg atcagttgtt ggctaacaga    300
accattccag attctgttag agctggtaac catgacaaat tgtctatgtc ttggttgcca    360
atttctgcta agtggcgtaa cttgagaaag atttccgctg tccaactgtt gtccaatcaa    420
agattggatg cttctcaagc tcatagacaa gctaaagttg aacaactgtt ggcttacgtt    480
caagactgtt ctaaaaaagg tcaaccagtt gatattggta gagctgcttt tactacctcc    540
ttgaacttgt tgtctaacac cttcttctct accgaattgg cttctcatga atccaacaac    600
tctcaagaat tcaagcagtt gatgtggaac atcatggaag aaattggtag accaaactac    660
gctgattact tcccaatttt gggttacgtt gatccattcg cattagaaag aagattggct    720
gcatacttcg ataagttgat tgctgttttc caagacatca tctgcgaaag acaaaagatc    780
aggtctacga aggtttcctc tgaaaaacaa accggtgata tcttggatac cctgttgaac    840
ttatacgacg aaaacgaatt atccatgggt gagatcaacc acttgttggt tgatattttt    900
gatgccggta ctgataccac tgcttctact ttggaatggg ctatggctga attggttaag    960
aatccaggta tgatgatcag agtccagaac gaaattgaat tggctattgg taagggttgc   1020
tccatggttc aagaagctga tatttctaag ttgccatact tgcaggccat catcaaagaa   1080
actttgagat tgcatccacc aaccgttttt ttgttgccaa gaaaggctga tatcgatgtt   1140
gagttgtacg gttatgttgt tccaaagaac gctcaagttt tggttaactt gtgggctata   1200
ggtagagatc caaaggtttg gaaaaaccca gaaatcttct caccagaaag attcttgggt   1260
tgcgatattg atttcaaggg tagagatttt gagttgttgc catttggtgc tggtagaaga   1320
atttgtccag gttgactttt ggcttacagg atgttgaatc taatgatggc caacttcgtt   1380
cactctttcg attggaaatt ggaggatggt atgaaccctta aggatttgga tatggacgaa   1440
aagttcggta tcaccttgca aaaagttaag ccattgcaag ttatcccagt ccacagataa   1500
```

<210> SEQ ID NO 34
<211> LENGTH: 499
<212> TYPE: PRT
<213> ORGANISM: Chenopodium quinoa

<400> SEQUENCE: 34

```
Met Glu His Thr Thr Leu Ala Leu Ile Leu Ser Ile Leu Phe Ile Cys
1               5                   10                  15

Phe His Leu Val Arg Ser Phe Val Ser His Ser Thr Lys Ser Asn Lys
            20                  25                  30

Leu Pro Pro Gly Pro Lys Arg Met Pro Ile Phe Gly Asn Ile Leu Asp
        35                  40                  45

Leu Gly Glu Lys Pro His Arg Ser Phe Ala Asn Leu Ala Lys Ile His
    50                  55                  60

Gly Pro Leu Val Ser Leu Gln Leu Gly Ser Ile Thr Thr Ile Ile Val
65                  70                  75                  80

Ser Ser Ala Asp Val Ala Lys Glu Met Phe Leu Lys Asn Asp Gln Leu
                85                  90                  95

Leu Ala Asn Arg Thr Ile Pro Asp Ser Val Arg Ala Gly Asn His Asp
            100                 105                 110

Lys Leu Ser Met Ser Trp Leu Pro Ile Ser Ala Lys Trp Arg Asn Leu
        115                 120                 125

Arg Lys Ile Ser Ala Val Gln Leu Leu Ser Asn Gln Arg Leu Asp Ala
    130                 135                 140
```

```
Ser Gln Ala His Arg Gln Ala Lys Val Glu Gln Leu Leu Ala Tyr Val
145                 150                 155                 160

Gln Asp Cys Ser Lys Gly Gln Pro Val Asp Ile Gly Arg Ala Ala
            165                 170                 175

Phe Thr Thr Ser Leu Asn Leu Leu Ser Asn Thr Phe Phe Ser Thr Glu
            180                 185                 190

Leu Ala Ser His Glu Ser Asn Asn Ser Gln Glu Phe Lys Gln Leu Met
            195                 200                 205

Trp Asn Ile Met Glu Glu Ile Gly Arg Pro Asn Tyr Ala Asp Tyr Phe
210                 215                 220

Pro Ile Leu Gly Tyr Val Asp Pro Phe Gly Ile Arg Arg Arg Leu Ala
225                 230                 235                 240

Ala Tyr Phe Asp Lys Leu Ile Ala Val Phe Gln Asp Ile Ile Cys Glu
            245                 250                 255

Arg Gln Lys Ile Arg Ser Thr Lys Val Ser Ser Glu Lys Gln Thr Gly
            260                 265                 270

Asp Ile Leu Asp Thr Leu Leu Asn Leu Tyr Asp Glu Asn Glu Leu Ser
            275                 280                 285

Met Gly Glu Ile Asn His Leu Leu Val Asp Ile Phe Asp Ala Gly Thr
            290                 295                 300

Asp Thr Thr Ala Ser Thr Leu Glu Trp Ala Met Ala Glu Leu Val Lys
305                 310                 315                 320

Asn Pro Gly Met Met Ile Arg Val Gln Asn Glu Ile Glu Leu Ala Ile
                325                 330                 335

Gly Lys Gly Cys Ser Met Val Gln Glu Ala Asp Ile Ser Lys Leu Pro
            340                 345                 350

Tyr Leu Gln Ala Ile Ile Lys Glu Thr Leu Arg Leu His Pro Pro Thr
            355                 360                 365

Val Phe Leu Leu Pro Arg Lys Ala Asp Ile Asp Val Glu Leu Tyr Gly
370                 375                 380

Tyr Val Val Pro Lys Asn Ala Gln Val Leu Val Asn Leu Trp Ala Ile
385                 390                 395                 400

Gly Arg Asp Pro Lys Val Trp Lys Asn Pro Glu Ile Phe Ser Pro Glu
                405                 410                 415

Arg Phe Leu Gly Cys Asp Ile Asp Phe Lys Gly Arg Asp Phe Glu Leu
            420                 425                 430

Leu Pro Phe Gly Ala Gly Arg Arg Ile Cys Pro Gly Leu Thr Leu Ala
            435                 440                 445

Tyr Arg Met Leu Asn Leu Met Met Ala Asn Phe Val His Ser Phe Asp
            450                 455                 460

Trp Lys Leu Glu Asp Gly Met Asn Pro Lys Asp Leu Asp Met Asp Glu
465                 470                 475                 480

Lys Phe Gly Ile Thr Leu Gln Lys Val Lys Pro Leu Gln Val Ile Pro
                485                 490                 495

Val His Arg
```

<210> SEQ ID NO 35
<211> LENGTH: 1485
<212> TYPE: DNA
<213> ORGANISM: Mirabilis multiflora

<400> SEQUENCE: 35
atggaccaaa ctaccttggc catgttgttg tctgcattat acctgctgta caacttgttc    60

```
aaggttatct tcacccagtc caattctaaa ttgccaccag gtccaaaacc attgccaatt    120
ttgggtaaca ttttcgagtt gggtgataag ccacataggt cttttaacaa cttggctaag    180
attcacggtc cattgattac tttgaagttg ggttctgtta cgaccatcgt tgtttcttca    240
gctaaagttg ccgaagagat gttcttgaag aatgatttgc cattggccaa cagaaacgtt    300
ccaaattctg ttactgctgg tgatcatcat aagttgacta tgtcttggtt gccagtttct    360
ccaaagtgga aaaccttcag aaagattacc gctgttcatt tgttgtcccc acaaagattg    420
gatgcttgtc aagctttgag acatgctaaa gttaagcagt tgtaccaata cgttcaagat    480
tgtgctaaaa agggtgaagc cgttgatatt ggtaaagctg cctttactac ttccctgaac    540
tgttgtctta acctgttctt ctctgttgaa ttggctcaac atacctcctc ttcatcccaa    600
catttcaaag aattgatctg ggacatcatg aagatatcg gtaagccaaa ttacgctgat    660
tatttcccag ctttgaagtg tgttgatcca tggggtatta agaagagatt ggctgctaat    720
ttcgaaaggt tgatccaagt gttccagaac ttcattagac agagattgtc taccgatcca    780
tcttctgtta caaatgcttc tgatgttttg gacgtcctgc tgaacctata caagaaaaaa    840
gaactgaaca tgggcgagat caaccatttg ttggttgata ttttgatgc cggtactgat    900 accacttctt ctacatttga atgggctatg gctgaattgg ttagacatcc agaaattatg    960
aagaaggccc aagacgaaat cgaacaagtt ttaggtaagg atgccaccat tcaagaagct    1020
gatattccaa aaatgccata cttgcaggcc atcatcaaag aaactttgag attgcatcca    1080
ccaaccgttt ttttgttgcc aagaaaggct actaccaacg tcgaattata tggttacgtt    1140
gttccaaaga acgcccaaat cttggttaat ttgtgggcta ttggtagaga tccattggtt    1200
tgggatcagc caaacaaatt ttctccagaa aggttcttga actccgatat cgatgttaag    1260
ggtagagatt ttggtttgtt gcctttggt gctggtagaa gaatttgtcc aggtatgaat    1320
ttggcctaca gaatgttgac tttgatgttg gctactctgt tgcaatcttt cgaatggaag    1380
gttcaaaatg gtgaaaagcc tgaagatttg gacatggacg aaaaatttgg tatcgccttg    1440
caaaagacta agccattgga aattattccc gtcctgaagt actga               1485

<210> SEQ ID NO 36
<211> LENGTH: 494
<212> TYPE: PRT
<213> ORGANISM: Mirabilis multiflora

<400> SEQUENCE: 36

Met Asp Gln Thr Thr Leu Ala Met Leu Leu Ser Ala Leu Tyr Leu Leu
1               5                   10                  15

Tyr Asn Leu Phe Lys Val Ile Phe Thr Gln Ser Asn Ser Lys Leu Pro
            20                  25                  30

Pro Gly Pro Lys Pro Leu Pro Ile Leu Gly Asn Ile Phe Glu Leu Gly
        35                  40                  45

Asp Lys Pro His Arg Ser Phe Asn Asn Leu Ala Lys Ile His Gly Pro
    50                  55                  60

Leu Ile Thr Leu Lys Leu Gly Ser Val Thr Thr Ile Val Val Ser Ser
65                  70                  75                  80

Ala Lys Val Ala Glu Glu Met Phe Leu Lys Asn Asp Leu Pro Leu Ala
                85                  90                  95

Asn Arg Asn Val Pro Asn Ser Val Thr Ala Gly Asp His His Lys Leu
            100                 105                 110

Thr Met Ser Trp Leu Pro Val Ser Pro Lys Trp Lys Thr Phe Arg Lys
        115                 120                 125
```

Ile Thr Ala Val His Leu Leu Ser Pro Gln Arg Leu Asp Ala Cys Gln
        130                 135                 140

Ala Leu Arg His Ala Lys Val Lys Gln Leu Tyr Gln Tyr Val Gln Asp
145                 150                 155                 160

Cys Ala Lys Lys Gly Glu Ala Val Asp Ile Gly Lys Ala Ala Phe Thr
                165                 170                 175

Thr Ser Leu Asn Leu Leu Ser Asn Leu Phe Phe Ser Val Glu Leu Ala
                180                 185                 190

Gln His Thr Ser Ser Ser Gln His Phe Lys Glu Leu Ile Trp Asp
            195                 200                 205

Ile Met Glu Asp Ile Gly Lys Pro Asn Tyr Ala Asp Tyr Phe Pro Ala
210                 215                 220

Leu Lys Cys Val Asp Pro Trp Gly Ile Arg Arg Leu Ala Ala Asn
225                 230                 235                 240

Phe Glu Arg Leu Ile Gln Val Phe Gln Asn Phe Ile Arg Gln Arg Leu
                245                 250                 255

Ser Thr Asp Pro Ser Ser Val Thr Asn Ala Ser Asp Val Leu Asp Val
                260                 265                 270

Leu Leu Asn Leu Tyr Lys Glu Lys Glu Leu Asn Met Gly Glu Ile Asn
                275                 280                 285

His Leu Leu Val Asp Ile Phe Asp Ala Gly Thr Asp Thr Thr Ser Ser
            290                 295                 300

Thr Phe Glu Trp Ala Met Ala Glu Leu Val Arg His Pro Glu Ile Met
305                 310                 315                 320

Lys Lys Ala Gln Asp Glu Ile Glu Gln Val Leu Gly Lys Asp Ala Thr
                325                 330                 335

Ile Gln Glu Ala Asp Ile Pro Lys Met Pro Tyr Leu Gln Ala Ile Ile
                340                 345                 350

Lys Glu Thr Leu Arg Leu His Pro Pro Thr Val Phe Leu Leu Pro Arg
                355                 360                 365

Lys Ala Thr Thr Asn Val Glu Leu Tyr Gly Tyr Val Val Pro Lys Asn
370                 375                 380

Ala Gln Ile Leu Val Asn Leu Trp Ala Ile Gly Arg Asp Pro Leu Val
385                 390                 395                 400

Trp Asp Gln Pro Asn Lys Phe Ser Pro Glu Arg Phe Leu Asn Ser Asp
                405                 410                 415

Ile Asp Val Lys Gly Arg Asp Phe Gly Leu Leu Pro Phe Gly Ala Gly
                420                 425                 430

Arg Arg Ile Cys Pro Gly Met Asn Leu Ala Tyr Arg Met Leu Thr Leu
            435                 440                 445

Met Leu Ala Thr Leu Leu Gln Ser Phe Glu Trp Lys Val Gln Asn Gly
450                 455                 460

Glu Lys Pro Glu Asp Leu Asp Met Asp Glu Lys Phe Gly Ile Ala Leu
465                 470                 475                 480

Gln Lys Thr Lys Pro Leu Glu Ile Ile Pro Val Leu Lys Tyr
                485                 490

<210> SEQ ID NO 37
<211> LENGTH: 1500
<212> TYPE: DNA
<213> ORGANISM: Chenopodium quinoa

<400> SEQUENCE: 37
atggaacata ccatcctggc cttgatcttg tccattttgt tcatttgctt ccacttggtc    60

-continued

```
aggtcctttg tttctcattc tactaagtct aacaagttgc caccaggtcc aaaaagaatg      120
ccaattttcg gtaacatctt cgacttgggt gaaaagccac atagatcttt tgctaacttg      180
gctaagattc acggtccatt ggtttcttta caattgggtt ctatcacgac catcgttgtt      240
tcttcagctg atgttgctaa agaaatgttc ttgaagaacg atcaagcttt ggccaacaga      300
actattccag attctgttag agctggtgat cacgataagt tgtctatgtc ttggttgcca      360
atttctgcta agtggcgtaa cttgagaaag atttccgctg tccaactgtt gtccaatcaa      420
agattggatg cttctcaagc tcatagacaa gctaaagttg aacagttgtt ggcttacgtt      480
caagactgtt ctaaaaaggg tcaaccagtt gatattggta gagctgcttt tactacctcc      540
ttgaacttgt tgtctaacac cttcttctct accgaattgg cttctcatga atccaacaac      600
tctcaagaat tcaagcagtt gatgtggaac atcatggaag aaattggtaa gccaaactac      660
gctgatttct tcccaatttt gggttacgtt gatccattcg gcattagaag aagattggct      720
ggttacttcg acaagttgat tgctgttttc caagacatca tttgcgagag acaaaagatt      780
aggtctacca aggtttcctc tgaaaagcaa actggtgata tcttggatac cctgttgaac      840
ttatacgacg aaaacgaatt gtccatgggt gaaatcaacc acttgttggt tgatattttc      900
gatgctggta ctgataccac tgcttctact ttggaatggg ctatggctga attggttaag      960
aatccaggta tgatgatcag agtccagaac gaaattgaat tggctattgg taagggttgc     1020
tccatggttc aagaatctga tatttctaag ctgccatact gcaggccat  tatcaaagaa     1080
actttgagat tgcatccacc aaccgttttt ttgttgccaa gaaagcaga  tgttgacgtt     1140
gagttgtacg gttatgttgt tccaaagaat gctcaagtct tggttaactt gtgggctata     1200
ggtagagatc caaggttttg gaaaaaccca gaaatcttta gcccagaaag attcattggt     1260
tgcgatatcg atttcaaggg tagagatttc gagttgttgc catttggtgc tggtagaaga     1320
atttgtccag gtttgacttt ggcatacagg atgttgaatt tgatgatggc ttacttcgtt     1380
cactccttcg attggaaatt ggaagatggt atgaacccaa aggacttgga tatggacgaa     1440
aagtttggta tcaccttgca aaaggttaag ccattgcaag ttatcccagt ccaaagatga     1500
```

<210> SEQ ID NO 38
<211> LENGTH: 499
<212> TYPE: PRT
<213> ORGANISM: Chenopodium quinoa

<400> SEQUENCE: 38

```
Met Glu His Thr Ile Leu Ala Leu Ile Leu Ser Ile Leu Phe Ile Cys
1               5                   10                  15

Phe His Leu Val Arg Ser Phe Val Ser His Ser Thr Lys Ser Asn Lys
            20                  25                  30

Leu Pro Pro Gly Pro Lys Arg Met Pro Ile Phe Gly Asn Ile Phe Asp
        35                  40                  45

Leu Gly Glu Lys Pro His Arg Ser Phe Ala Asn Leu Ala Lys Ile His
    50                  55                  60

Gly Pro Leu Val Ser Leu Gln Leu Gly Ser Ile Thr Thr Ile Val Val
65                  70                  75                  80

Ser Ser Ala Asp Val Ala Lys Glu Met Phe Leu Lys Asn Asp Gln Ala
                85                  90                  95

Leu Ala Asn Arg Thr Ile Pro Asp Ser Val Arg Ala Gly Asp His Asp
            100                 105                 110

Lys Leu Ser Met Ser Trp Leu Pro Ile Ser Ala Lys Trp Arg Asn Leu
```

```
                115                 120                 125
Arg Lys Ile Ser Ala Val Gln Leu Leu Ser Asn Gln Arg Leu Asp Ala
            130                 135                 140

Ser Gln Ala His Arg Gln Ala Lys Val Glu Gln Leu Leu Ala Tyr Val
145                 150                 155                 160

Gln Asp Cys Ser Lys Lys Gly Gln Pro Val Asp Ile Gly Arg Ala Ala
                165                 170                 175

Phe Thr Thr Ser Leu Asn Leu Leu Ser Asn Thr Phe Phe Ser Thr Glu
            180                 185                 190

Leu Ala Ser His Glu Ser Asn Asn Ser Gln Glu Phe Lys Gln Leu Met
            195                 200                 205

Trp Asn Ile Met Glu Ile Gly Lys Pro Asn Tyr Ala Asp Phe Phe
        210                 215                 220

Pro Ile Leu Gly Tyr Val Asp Pro Phe Gly Ile Arg Arg Arg Leu Ala
225                 230                 235                 240

Gly Tyr Phe Asp Lys Leu Ile Ala Val Phe Gln Asp Ile Ile Cys Glu
                245                 250                 255

Arg Gln Lys Ile Arg Ser Thr Lys Val Ser Ser Glu Lys Gln Thr Gly
            260                 265                 270

Asp Ile Leu Asp Thr Leu Leu Asn Leu Tyr Asp Glu Asn Glu Leu Ser
        275                 280                 285

Met Gly Glu Ile Asn His Leu Leu Val Asp Ile Phe Asp Ala Gly Thr
    290                 295                 300

Asp Thr Thr Ala Ser Thr Leu Glu Trp Ala Met Ala Glu Leu Val Lys
305                 310                 315                 320

Asn Pro Gly Met Met Ile Arg Val Gln Asn Glu Ile Glu Leu Ala Ile
                325                 330                 335

Gly Lys Gly Cys Ser Met Val Gln Glu Ser Asp Ile Ser Lys Leu Pro
            340                 345                 350

Tyr Leu Gln Ala Ile Ile Lys Glu Thr Leu Arg Leu His Pro Pro Thr
        355                 360                 365

Val Phe Leu Leu Pro Arg Lys Ala Asp Val Asp Val Glu Leu Tyr Gly
    370                 375                 380

Tyr Val Val Pro Lys Asn Ala Gln Val Leu Val Asn Leu Trp Ala Ile
385                 390                 395                 400

Gly Arg Asp Pro Lys Val Trp Lys Asn Pro Glu Ile Phe Ser Pro Glu
                405                 410                 415

Arg Phe Ile Gly Cys Asp Ile Asp Phe Lys Gly Arg Asp Phe Glu Leu
            420                 425                 430

Leu Pro Phe Gly Ala Gly Arg Arg Ile Cys Pro Gly Leu Thr Leu Ala
        435                 440                 445

Tyr Arg Met Leu Asn Leu Met Met Ala Tyr Phe Val His Ser Phe Asp
    450                 455                 460

Trp Lys Leu Glu Asp Gly Met Asn Pro Lys Asp Leu Asp Met Asp Glu
465                 470                 475                 480

Lys Phe Gly Ile Thr Leu Gln Lys Val Lys Pro Leu Gln Val Ile Pro
                485                 490                 495

Val Gln Arg

<210> SEQ ID NO 39
<211> LENGTH: 1503
<212> TYPE: DNA
<213> ORGANISM: Phytolacca Americana
```

<400> SEQUENCE: 39

```
atggaccata ccaccattgc catgttggtt tctatcgttt tcttgtgctt ccacctgatc      60
aagtctttct catctcattc taagaaccca tctcaattgc caccaggtcc aaaaccatta    120
ccaattttcg gtaacatctt cgagttgggt gaaaagccac atagatcttt tgctagattg    180
gccaaaattc acggtccatt gatttctttg aagttgggtt ctgttacgac atcgttgtc     240
tcttcatctg aagttgccaa agaaatgttc ttgaagcacg atcaagtttt ggctaacaga    300
actatcccag attctgttag agctggtaac catgataagt tgtctatgtc ttggttgcca    360
gtttctgtta agtggcgttc tttgagaaag atcgttgttg ttcagttgtt ctctacccaa    420
agattggatg tctctcaatc tttgagacat gccaaggttc aacaattgca tgagtacatt    480
accgagtgtt ctaaaaaggg tgaaccagtt gatattggta gagctgcttt tactacctcc    540
ttgaacttgt tgtctaacac cttcttctct atggaattgg ccaaccattc ttcatcagct    600
tctcaagaat tcaagcaatt gatgtggtgc atcatggaag aaattggtag accaaattac    660
gccgatttct tcccaatttt gggttacgtt gatccattcg gtatcagaag aagattggct    720
gtttacttcg ataagttgat cgctgtgttc caagaaatca tcagagaaag acaaaaggcc    780
agattcacta acttgtctac taccaacgat gttttggaca ccttgctgaa cttgtaccaa    840
gaaaatgaat tgagcatgga cgagatcaac cacttgttgg ttgatatttt tgatgccggt    900
actgatacca ctgcttctac aatggaatgg gctatggctg aattggttaa gaatccagat    960
attatgttga aggccaggat cgaaatcaaa caagctttgg gtaatgactc cagcttgatc   1020
attcaagaat ctgatattgc caagctgcca tacttgcaag ctattgtcaa agaaaccttg   1080
agattgcatc caccaaccgt ttttttgttg ccaagaaaag ctgaagctaa cgtccaatta   1140
tacggctact tgattccaaa gaatgcccag ttgttggtta acttgtgggc tataggtaga   1200
gatccaaatg tttggaatga ccccttggtt ttttcaccag aaagattctt ggcttcctcc   1260
tcttgtgaaa ttgatgttaa gggtagacac tttgagttgt tgccatttgg tgctggtaga   1320
agaatttgtc aggtttgac tttggcatac aggatgttga atttgatgtt ggtgactctg    1380
gttaactcct tcgattggaa attggaagat gtcacttctg ccaaggatt ggatatggac    1440
gaaaagtttg gtatccactt gcaaaaggtt aagccattgc aattgatccc cattccaaag   1500
tga                                                                  1503
```

<210> SEQ ID NO 40
<211> LENGTH: 500
<212> TYPE: PRT
<213> ORGANISM: Phytolacca Americana

<400> SEQUENCE: 40

```
Met Asp His Thr Thr Ile Ala Met Leu Val Ser Ile Val Phe Leu Cys
1               5                  10                  15

Phe His Leu Ile Lys Ser Phe Ser Ser His Ser Lys Asn Pro Ser Gln
            20                  25                  30

Leu Pro Pro Gly Pro Lys Pro Leu Pro Ile Phe Gly Asn Ile Phe Glu
        35                  40                  45

Leu Gly Glu Lys Pro His Arg Ser Phe Ala Arg Leu Ala Lys Ile His
    50                  55                  60

Gly Pro Leu Ile Ser Leu Lys Leu Gly Ser Val Thr Thr Ile Val Val
65                  70                  75                  80

Ser Ser Ser Glu Val Ala Lys Glu Met Phe Leu Lys His Asp Gln Val
                85                  90                  95
```

```
Leu Ala Asn Arg Thr Ile Pro Asp Ser Val Arg Ala Gly Asn His Asp
            100                 105                 110

Lys Leu Ser Met Ser Trp Leu Pro Val Ser Val Lys Trp Arg Ser Leu
            115                 120                 125

Arg Lys Ile Val Val Gln Leu Phe Ser Thr Gln Arg Leu Asp Val
            130                 135                 140

Ser Gln Ser Leu Arg His Ala Lys Val Gln Gln Leu His Glu Tyr Ile
145                 150                 155                 160

Thr Glu Cys Ser Lys Lys Gly Glu Pro Val Asp Ile Gly Arg Ala Ala
                165                 170                 175

Phe Thr Thr Ser Leu Asn Leu Ser Asn Thr Phe Phe Ser Met Glu
                180                 185                 190

Leu Ala Asn His Ser Ser Ser Ala Ser Gln Glu Phe Lys Gln Leu Met
            195                 200                 205

Trp Cys Ile Met Glu Glu Ile Gly Arg Pro Asn Tyr Ala Asp Phe Phe
            210                 215                 220

Pro Ile Leu Gly Tyr Val Asp Pro Phe Gly Ile Arg Arg Leu Ala
225                 230                 235                 240

Val Tyr Phe Asp Lys Leu Ile Ala Val Phe Gln Glu Ile Ile Arg Glu
                245                 250                 255

Arg Gln Lys Ala Arg Phe Thr Asn Leu Ser Thr Thr Asn Asp Val Leu
            260                 265                 270

Asp Thr Leu Leu Asn Leu Tyr Gln Glu Asn Glu Leu Ser Met Asp Glu
            275                 280                 285

Ile Asn His Leu Leu Val Asp Ile Phe Asp Ala Gly Thr Asp Thr Thr
            290                 295                 300

Ala Ser Thr Met Glu Trp Ala Met Ala Glu Leu Val Lys Asn Pro Asp
305                 310                 315                 320

Ile Met Leu Lys Ala Arg Ile Glu Ile Lys Gln Ala Leu Gly Asn Asp
            325                 330                 335

Ser Ser Leu Ile Ile Gln Glu Ser Asp Ile Ala Lys Leu Pro Tyr Leu
            340                 345                 350

Gln Ala Ile Val Lys Glu Thr Leu Arg Leu His Pro Pro Thr Val Phe
            355                 360                 365

Leu Leu Pro Arg Lys Ala Glu Ala Asn Val Gln Leu Tyr Gly Tyr Leu
            370                 375                 380

Ile Pro Lys Asn Ala Gln Leu Leu Val Asn Leu Trp Ala Ile Gly Arg
385                 390                 395                 400

Asp Pro Asn Val Trp Asn Asp Pro Leu Val Phe Ser Pro Glu Arg Phe
                405                 410                 415

Leu Ala Ser Ser Ser Cys Glu Ile Asp Val Lys Gly Arg His Phe Glu
                420                 425                 430

Leu Leu Pro Phe Gly Ala Gly Arg Arg Ile Cys Pro Gly Leu Thr Leu
            435                 440                 445

Ala Tyr Arg Met Leu Asn Leu Met Leu Val Thr Leu Val Asn Ser Phe
            450                 455                 460

Asp Trp Lys Leu Glu Asp Val Thr Ser Ala Lys Asp Leu Asp Met Asp
465                 470                 475                 480

Glu Lys Phe Gly Ile Thr Leu Gln Lys Val Lys Pro Leu Gln Leu Ile
                485                 490                 495

Pro Ile Pro Lys
            500
```

<210> SEQ ID NO 41
<211> LENGTH: 1485
<212> TYPE: DNA
<213> ORGANISM: Abronia nealleyi

<400> SEQUENCE: 41

```
atggaccaaa ctaccttggc catgttgttg tctgcattat acctgctgta caacctgtac     60
aaggttatct tcactcagtc caattctaaa ttgccaccag gtccaaaacc attgccaatt    120
tttggtaaca tctctgaatt gggtgctaag ccacatagat cttttgctaa cttggctaag    180
attcacggtc cattgattac tttgaagttg ggttctgtta cgaccatcgt tgtttcttca    240
gctaaagttg ccgaagagat gttcttgaag aatgatttgc cattggccaa cagaaacgtt    300
ccaaattctg ttactgctgg tgatcatcat aagttgacta tgtcttggtt gccagtttct    360
ccaaagtgga aaaccttcag aaagattacc gctgttcatt tgttgtcccc acaaagattg    420
gatgcttgtc aagctttgag acatgctaaa gttaagcagt tgtacgaata cgtttacgat    480
tgtgctaaaa agggtgaagc cgttgatatt ggtaaagctg cttttactac ctccttgaac    540
ttgctgtcta acttgttctt ctctgttgaa ttggctcaac atacctctac ctcttcacaa    600
catttcaagc aattgatctg ggacatcatg gaagatatcg gtaagccaaa ttacgctgat    660
tatttcccag ctttgaagtg tgttgatcca tggggtatta gaagaagatt ggctgctaat    720
ttcgaaaggt tgatcgatgt tttccaggac ttcattagac caaggttgtc tatgaatcca    780
tcctctgtta cttcagcttc tgatgttttg gatgtcctgc tgaacttgta caaagaaaaa    840
gaattgaaca tgggcgaagt caaccacttg ttggttgata tttttgatgc tggtactgac    900
accacttctt ctacatttga atgggctatg gctgaattgg ttagacatcc agaaactatg    960
aagaaggccc aagacgaaat tgaacaagtt ttgggtaaag atgccaccat tcaagaagct   1020
gatattccaa aaatgccata cttgcaggcc atcatcaaag aaactttgag attgcatcca   1080
ccaaccgttt ttttgttgcc aagaaaagct gctaccaacg tcgaattata tggttacgtt   1140
gttccaaagg atgcccaaat cttggttaat ttgtgggcta ttggtagaga tccattggtt   1200
tgggatcaac ctaatgtttt ctcaccagaa aggttcttga actccgatgt tgatgttaag   1260
ggtagagatt ttggtttgtt gccttttggt gcaggtagaa gaatttgtcc aggtatgaat   1320
ttggcctaca gaatgttgac tttgatgttg gctactctgt tgcaatcttt cgaatggaag   1380
gttgaaaatg gtgaaaaggc cgaagatttg gatatggacg aaaaatttgg tatcgccttg   1440
caaaagacta agccattgca aattattccc gtcctgaagt actga                   1485
```

<210> SEQ ID NO 42
<211> LENGTH: 494
<212> TYPE: PRT
<213> ORGANISM: Abronia nealleyi

<400> SEQUENCE: 42

```
Met Asp Gln Thr Thr Leu Ala Met Leu Leu Ser Ala Leu Tyr Leu Leu
1               5                   10                  15

Tyr Asn Leu Tyr Lys Val Ile Phe Thr Gln Ser Asn Ser Lys Leu Pro
            20                  25                  30

Pro Gly Pro Lys Pro Leu Pro Ile Phe Gly Asn Ile Ser Glu Leu Gly
        35                  40                  45

Ala Lys Pro His Arg Ser Phe Ala Asn Leu Ala Lys Ile His Gly Pro
    50                  55                  60

Leu Ile Thr Leu Lys Leu Gly Ser Val Thr Thr Ile Val Val Ser Ser
```

```
            65                  70                  75                  80
Ala Lys Val Ala Glu Glu Met Phe Leu Lys Asn Asp Leu Pro Leu Ala
                85                  90                  95

Asn Arg Asn Val Pro Asn Ser Val Thr Ala Gly Asp His His Lys Leu
                100                 105                 110

Thr Met Ser Trp Leu Pro Val Ser Pro Lys Trp Lys Thr Phe Arg Lys
                115                 120                 125

Ile Thr Ala Val His Leu Leu Ser Pro Gln Arg Leu Asp Ala Cys Gln
    130                 135                 140

Ala Leu Arg His Ala Lys Val Lys Gln Leu Tyr Glu Tyr Val Tyr Asp
145                 150                 155                 160

Cys Ala Lys Lys Gly Glu Ala Val Asp Ile Gly Lys Ala Ala Phe Thr
                165                 170                 175

Thr Ser Leu Asn Leu Leu Ser Asn Leu Phe Phe Ser Val Glu Leu Ala
                180                 185                 190

Gln His Thr Ser Thr Ser Ser Gln His Phe Lys Gln Leu Ile Trp Asp
                195                 200                 205

Ile Met Glu Asp Ile Gly Lys Pro Asn Tyr Ala Asp Tyr Phe Pro Ala
    210                 215                 220

Leu Lys Cys Val Asp Pro Trp Gly Ile Arg Arg Leu Ala Ala Asn
225                 230                 235                 240

Phe Glu Arg Leu Ile Asp Val Phe Gln Asp Phe Ile Arg Pro Arg Leu
                245                 250                 255

Ser Met Asn Pro Ser Ser Val Thr Ser Ala Ser Asp Val Leu Asp Val
                260                 265                 270

Leu Leu Asn Leu Tyr Lys Glu Lys Glu Leu Asn Met Gly Glu Val Asn
                275                 280                 285

His Leu Leu Val Asp Ile Phe Asp Ala Gly Thr Asp Thr Thr Ser Ser
                290                 295                 300

Thr Phe Glu Trp Ala Met Ala Glu Leu Val Arg His Pro Glu Thr Met
305                 310                 315                 320

Lys Lys Ala Gln Asp Glu Ile Glu Gln Val Leu Gly Lys Asp Ala Thr
                325                 330                 335

Ile Gln Glu Ala Asp Ile Pro Lys Met Pro Tyr Leu Gln Ala Ile Ile
                340                 345                 350

Lys Glu Thr Leu Arg Leu His Pro Pro Thr Val Phe Leu Leu Pro Arg
                355                 360                 365

Lys Ala Ala Thr Asn Val Glu Leu Tyr Gly Tyr Val Val Pro Lys Asp
                370                 375                 380

Ala Gln Ile Leu Val Asn Leu Trp Ala Ile Gly Arg Asp Pro Leu Val
385                 390                 395                 400

Trp Asp Gln Pro Asn Val Phe Ser Pro Glu Arg Phe Leu Asn Ser Asp
                405                 410                 415

Val Asp Val Lys Gly Arg Asp Phe Gly Leu Leu Pro Phe Gly Ala Gly
                420                 425                 430

Arg Arg Ile Cys Pro Gly Met Asn Leu Ala Tyr Arg Met Leu Thr Leu
                435                 440                 445

Met Leu Ala Thr Leu Leu Gln Ser Phe Glu Trp Lys Val Glu Asn Gly
450                 455                 460

Glu Lys Ala Glu Asp Leu Asp Met Asp Glu Lys Phe Gly Ile Ala Leu
                470                 475                 480

Gln Lys Thr Lys Pro Leu Gln Ile Ile Pro Val Leu Lys Tyr
                485                 490
```

<210> SEQ ID NO 43
<211> LENGTH: 1494
<212> TYPE: DNA
<213> ORGANISM: Spinacia oleracea

<400> SEQUENCE: 43

```
atggaagata ccaccttggc catcttgttg tctatttctt tcgtttgctt ccacgtcatc    60
aggtcctttg tttctaagac cagatccaag tcatctgaat gccaccagg tccaaaaaga    120
atgccaattt tcggtaacat cttcgacttg ggtgataagc cacatagatc ttttgctaac    180
ttgtccaaga ttcacggtcc attggtttct ttgaagttgg gttctatcac taccatcgtt    240
gtttcttcag ctgatgttgc tagagaaatg ttcttgaaga atgatttggc tttggccaac    300
agaaccattc cagattctgt tagagctggt gatcatgaca aattgtctat gtcttggttg    360
ccagtttctg ctaaatggcg taacttgaga agatttctg ctgtccagct gttgtccaat    420
caaagattgg atgcttctca agctcataga caagctaaag ttgacagtt gttgacctac    480
gttaaggact gttctaaaaa cggtttgcca gttgatattg tagagctgc ttttactacc    540
tccttgaact tgttgtcaaa caccttcttc tctgttgaat tggcctctca tgaatcttca    600
gcttcccaag aattcaagca attgatgtgg aacatcatgg aagaaatcgg taagccaaat    660
tacgctgatt acttcccaat tttgggttac gttgatccat tcggtatcag aagaagattg    720
gctgcatact tcgaccaatt gattgctgtt ttccagaaca tcatccaaga gagacaaaag    780
attagatcca ccaacgctaa gcaaactaac gatattttgg acaccttgtt gaacttgcac    840
gacgaaaatg aattatccat gggtgaaatc aaccacttgt tggttgatat tttcgatgct    900
ggtactgata ccactgcttc tactttggaa tgggctatgg ctgaattggt taagaatcca    960
gaaatgatga ccaaggtcca gaacgaaatt gaacaagcta ttggtaagga ttgcgccacc    1020
attcaagaat ctgatattgc taaattgcca tacttgcagg ccattatcaa agagactttg    1080
agattgcatc cacctaccgt tttttgttg ccaagaaaag cagatgttga cgttgagttg    1140
tacggttatg ttgttccaaa gaacgctcaa gttttggtta acttgtgggc tataggtaga    1200
gatccaaagg tttggaaaaa cccagaagtt ttctcaccag aaaggttctt ggaatgcgat    1260
attgattaca gggtagaga cttcgagttg ttgccatttg gtgctggtag aagaatttgt    1320
ccaggtttga ctttggcata caggatgtga aatttgatga tgggtaactt cttgcactcc    1380
ttcgattgga aattggaaga tggtatgtct ccaaaggact tggatatgga cgaaaagttt    1440
ggtatcacct tgcaaaaggt taagccattg caagttattc cagtgccaag atga    1494
```

<210> SEQ ID NO 44
<211> LENGTH: 497
<212> TYPE: PRT
<213> ORGANISM: Spinacia oleracea

<400> SEQUENCE: 44

```
Met Glu Asp Thr Thr Leu Ala Ile Leu Leu Ser Ile Ser Phe Val Cys
 1               5                  10                  15

Phe His Val Ile Arg Ser Phe Val Ser Lys Thr Arg Ser Lys Ser Ser
            20                  25                  30

Glu Leu Pro Pro Gly Pro Lys Arg Met Pro Ile Phe Gly Asn Ile Phe
        35                  40                  45

Asp Leu Gly Asp Lys Pro His Arg Ser Phe Ala Asn Leu Ser Lys Ile
    50                  55                  60
```

```
His Gly Pro Leu Val Ser Leu Lys Leu Gly Ser Ile Thr Thr Ile Val
 65                  70                  75                  80

Val Ser Ser Ala Asp Val Ala Arg Glu Met Phe Leu Lys Asn Asp Leu
                 85                  90                  95

Ala Leu Ala Asn Arg Thr Ile Pro Asp Ser Val Arg Ala Gly Asp His
                100                 105                 110

Asp Lys Leu Ser Met Ser Trp Leu Pro Val Ser Ala Lys Trp Arg Asn
            115                 120                 125

Leu Arg Lys Ile Ser Ala Val Gln Leu Leu Ser Asn Gln Arg Leu Asp
        130                 135                 140

Ala Ser Gln Ala His Arg Gln Ala Lys Val Glu Gln Leu Leu Thr Tyr
145                 150                 155                 160

Val Lys Asp Cys Ser Lys Asn Gly Leu Pro Val Asp Ile Gly Arg Ala
                165                 170                 175

Ala Phe Thr Thr Ser Leu Asn Leu Leu Ser Asn Thr Phe Phe Ser Val
                180                 185                 190

Glu Leu Ala Ser His Glu Ser Ser Ala Ser Gln Glu Phe Lys Gln Leu
            195                 200                 205

Met Trp Asn Ile Met Glu Glu Ile Gly Lys Pro Asn Tyr Ala Asp Tyr
        210                 215                 220

Phe Pro Ile Leu Gly Tyr Val Asp Pro Phe Gly Ile Arg Arg Arg Leu
225                 230                 235                 240

Ala Ala Tyr Phe Asp Gln Leu Ile Ala Val Phe Gln Asn Ile Ile Gln
                245                 250                 255

Glu Arg Gln Lys Ile Arg Ser Thr Asn Ala Lys Gln Thr Asn Asp Ile
                260                 265                 270

Leu Asp Thr Leu Leu Asn Leu His Asp Glu Asn Glu Leu Ser Met Gly
            275                 280                 285

Glu Ile Asn His Leu Leu Val Asp Ile Phe Asp Ala Gly Thr Asp Thr
        290                 295                 300

Thr Ala Ser Thr Leu Glu Trp Ala Met Ala Glu Leu Val Lys Asn Pro
305                 310                 315                 320

Glu Met Met Thr Lys Val Gln Asn Glu Ile Glu Gln Ala Ile Gly Lys
                325                 330                 335

Asp Cys Ala Thr Ile Gln Glu Ser Asp Ile Ala Lys Leu Pro Tyr Leu
                340                 345                 350

Gln Ala Ile Ile Lys Glu Thr Leu Arg Leu His Pro Pro Thr Val Phe
            355                 360                 365

Leu Leu Pro Arg Lys Ala Asp Val Asp Val Glu Leu Tyr Gly Tyr Val
        370                 375                 380

Val Pro Lys Asn Ala Gln Val Leu Val Asn Leu Trp Ala Ile Gly Arg
385                 390                 395                 400

Asp Pro Lys Val Trp Lys Asn Pro Glu Val Phe Ser Pro Glu Arg Phe
                405                 410                 415

Leu Glu Cys Asp Ile Asp Tyr Lys Gly Arg Asp Phe Glu Leu Leu Pro
                420                 425                 430

Phe Gly Ala Gly Arg Arg Ile Cys Pro Gly Leu Thr Leu Ala Tyr Arg
            435                 440                 445

Met Leu Asn Leu Met Gly Asn Phe Leu His Ser Phe Asp Trp Lys
        450                 455                 460

Leu Glu Asp Gly Met Ser Pro Lys Asp Leu Asp Met Asp Glu Lys Phe
465                 470                 475                 480

Gly Ile Thr Leu Gln Lys Val Lys Pro Leu Gln Val Ile Pro Val Pro
```

|  | 485 | 490 | 495 |
|---|---|---|---|

Arg

<210> SEQ ID NO 45
<211> LENGTH: 1503
<212> TYPE: DNA
<213> ORGANISM: Spinacia oleracea

<400> SEQUENCE: 45

| atggaaaaca ccaccttggc cttgatcttg tctatttctt ttgtttgctt gcacgtcatc | 60 |
|---|---|
| aggtcttttt tgggtaaagc ttcctccaag tcatctaaat gccaccagg tccaaaaga | 120 |
| atgccaattt tcggtaacat cttcgacttg ggtgaaaagc cacatagatc ttttgctaac | 180 |
| ttggctaaga ttcacggtcc attggtttct tgaagttgg ttctatcac taccatcgtt | 240 |
| gtttcatctg ctgaagttgc caaagaaatg ttcttgaaga cgatcaagt tttggccaac | 300 |
| agaaccattc cagattctgt tagagctggt gatcatgaca aattgtctat gtcttggttg | 360 |
| ccagtttctg ctaaatggcg taacttgaga aagatttctg ctgtccagtt gttgtctaac | 420 |
| cagagattgg atgcttctca agctcataga caagctaaag ttgaacagtt gttgacctac | 480 |
| gttcaagact gttctaaaaa gggttttgcca gttgatattg gtagagctgc ttttactacc | 540 |
| tccttgaact tgttgtccaa caccttttc tctgttgaat tggcctctca tgaatcctct | 600 |
| gcttcacaag aattcaagca attgatgtgg aacatcatgg aagaaatcgg taagccaaat | 660 |
| tacgctgatt acttcccaat tttgggttac gttgatccat tcggtatcag aagaagattg | 720 |
| gctgcttact tcgaccaatt gattgctgtt ttccagaaca tcatccaaga gagacaaaag | 780 |
| attaggtcta ccaatggttc taacgccaag caaactaacg atatcttgga taccttgttg | 840 |
| aacttgcacg acgaaaacga attatccatg ggtgaaatca accacttgtt ggttgatatt | 900 |
| ttcgatgctg gtactgatac cactgcttct actttggaat gggctatggc tgaattgatt | 960 |
| aagaacccag aaatgatgac caaggtccag aacgaaattg aacaagctgt tggtaaagat | 1020 |
| tgctccgcca ttcaagaatc tgatattgca aaattgccct acctgcagtc cattatcaaa | 1080 |
| gagactttga ttgcatcc accaaccgtt tttttgttgc caagaaaagc tgatgttgac | 1140 |
| gttgagttgt acggttatgt tgttccaaag aatgctcaag tcttggttaa cttgtgggct | 1200 |
| ataggtagag atccaaaggt ttggaaaaac ccagagattt tctcaccaga aaggttcttg | 1260 |
| gaatgcgata ttgattacaa gggtagagac ttcgagttgt tgccatttgg tgctggtaga | 1320 |
| agaatttgtc caggtttgac tttggcatac aggatgttga atttgatgat gggtaacttc | 1380 |
| ttgcactcct tcgattggaa attggaagat ggtatgaacc caaggacttt ggatatggac | 1440 |
| gaaaagtttg gtatcacctt gcaaaaggtt aagccattgc aagttatccc agtctctaga | 1500 |
| tga | 1503 |

<210> SEQ ID NO 46
<211> LENGTH: 500
<212> TYPE: PRT
<213> ORGANISM: Spinacia oleracea

<400> SEQUENCE: 46

Met Glu Asn Thr Thr Leu Ala Leu Ile Leu Ser Ile Ser Phe Val Cys
1               5                   10                  15

Leu His Val Ile Arg Ser Phe Leu Gly Lys Ala Ser Ser Lys Ser Ser
            20                  25                  30

Lys Leu Pro Pro Gly Pro Lys Arg Met Pro Ile Phe Gly Asn Ile Phe

```
            35                  40                  45
Asp Leu Gly Glu Lys Pro His Arg Ser Phe Ala Asn Leu Ala Lys Ile
 50                  55                  60

His Gly Pro Leu Val Ser Leu Lys Leu Gly Ser Ile Thr Thr Ile Val
 65                  70                  75                  80

Val Ser Ser Ala Glu Val Ala Lys Glu Met Phe Leu Lys Asn Asp Gln
                 85                  90                  95

Val Leu Ala Asn Arg Thr Ile Pro Asp Ser Val Arg Ala Gly Asp His
                100                 105                 110

Asp Lys Leu Ser Met Ser Trp Leu Pro Val Ser Ala Lys Trp Arg Asn
            115                 120                 125

Leu Arg Lys Ile Ser Ala Val Gln Leu Leu Ser Asn Gln Arg Leu Asp
        130                 135                 140

Ala Ser Gln Ala His Arg Gln Ala Lys Val Glu Gln Leu Leu Thr Tyr
145                 150                 155                 160

Val Gln Asp Cys Ser Lys Lys Gly Leu Pro Val Asp Ile Gly Arg Ala
                165                 170                 175

Ala Phe Thr Thr Ser Leu Asn Leu Leu Ser Asn Thr Phe Phe Ser Val
                180                 185                 190

Glu Leu Ala Ser His Glu Ser Ser Ala Ser Gln Glu Phe Lys Gln Leu
            195                 200                 205

Met Trp Asn Ile Met Glu Glu Ile Gly Lys Pro Asn Tyr Ala Asp Tyr
        210                 215                 220

Phe Pro Ile Leu Gly Tyr Val Asp Pro Phe Gly Ile Arg Arg Arg Leu
225                 230                 235                 240

Ala Ala Tyr Phe Asp Gln Leu Ile Ala Val Phe Gln Asn Ile Ile Gln
                245                 250                 255

Glu Arg Gln Lys Ile Arg Ser Thr Asn Gly Ser Asn Ala Lys Gln Thr
                260                 265                 270

Asn Asp Ile Leu Asp Thr Leu Leu Asn Leu His Asp Glu Asn Glu Leu
            275                 280                 285

Ser Met Gly Glu Ile Asn His Leu Leu Val Asp Ile Phe Asp Ala Gly
        290                 295                 300

Thr Asp Thr Thr Ala Ser Thr Leu Glu Trp Ala Met Ala Glu Leu Ile
305                 310                 315                 320

Lys Asn Pro Glu Met Met Thr Lys Val Gln Asn Glu Ile Glu Gln Ala
                325                 330                 335

Val Gly Lys Asp Cys Ser Ala Ile Gln Glu Ser Asp Ile Ala Lys Leu
            340                 345                 350

Pro Tyr Leu Gln Ser Ile Ile Lys Glu Thr Leu Arg Leu His Pro Pro
        355                 360                 365

Thr Val Phe Leu Leu Pro Arg Lys Ala Asp Val Asp Val Glu Leu Tyr
370                 375                 380

Gly Tyr Val Val Pro Lys Asn Ala Gln Val Leu Val Asn Leu Trp Ala
385                 390                 395                 400

Ile Gly Arg Asp Pro Lys Val Trp Lys Asn Pro Glu Ile Phe Ser Pro
                405                 410                 415

Glu Arg Phe Leu Glu Cys Asp Ile Asp Tyr Lys Gly Arg Asp Phe Glu
            420                 425                 430

Leu Leu Pro Phe Gly Ala Gly Arg Arg Ile Cys Pro Gly Leu Thr Leu
        435                 440                 445

Ala Tyr Arg Met Leu Asn Leu Met Met Gly Asn Phe Leu His Ser Phe
450                 455                 460
```

Asp Trp Lys Leu Glu Asp Gly Met Asn Pro Lys Asp Leu Asp Met Asp
465                 470                 475                 480

Glu Lys Phe Gly Ile Thr Leu Gln Lys Val Lys Pro Leu Gln Val Ile
            485                 490                 495

Pro Val Ser Arg
            500

<210> SEQ ID NO 47
<211> LENGTH: 1497
<212> TYPE: DNA
<213> ORGANISM: Spinacia oleracea

<400> SEQUENCE: 47

| | | | | | |
|---|---|---|---|---|---|
| atggaaaaca | ccaccttggc | cttcatcttg | tctatttctt | tcgtttgctt | ccacgtcatc | 60 |
| aggtcccttta | tttctaaggc | cagatccaag | tcatctaaat | tgccaccagg | tccaaaaaga | 120 |
| atgccaattt | tcggtaacat | cttcgacttg | ggtgaaaagc | cacatagatc | ttttgctaac | 180 |
| ttgtccaaga | ttcacggtcc | attgattcct | ttgaagttgg | gttctatcac | gaccatcgtt | 240 |
| gtttcttcag | ctgatgttgc | taaagaaatg | ttcttgaaga | cgatcaagc | tttggccaac | 300 |
| agaactattc | cagattctgt | tagagctggt | gatcacgata | agttgtcaat | tcttggttg | 360 |
| ccagttctg | ctaagtggcg | taatttgaga | aagatttctg | ctgtccagtt | gttgtctaac | 420 |
| cagagattgg | atgcttctca | agctcataga | caagctaaag | ttgaacagtt | gttgacctac | 480 |
| gttaaggact | gttctaaaaa | gggtttgcca | gttgatattg | gtagagctgc | ttttactacc | 540 |
| tccttgaact | tgttgtccaa | caccttttc | tctgttgaat | tggcctctca | tgaatcctct | 600 |
| gcttcacaag | aattcaagca | attgatgtgg | aacatcatgg | aagaaatcgg | taagccaaac | 660 |
| tacgctgatt | actttccaat | tttgggttac | gttgatccat | tcggtatcag | aagaagattg | 720 |
| gctgcttact | tcgaccaatt | gattgctgtt | ttccaagaca | tcatccagaa | gagacaaaag | 780 |
| attaggtcta | ccaatggtgc | caagcaaact | aacgatattt | tggacacttt | gctgaacttg | 840 |
| cacgaagaaa | acgaattgtc | tatgggtgaa | atcaaccact | tgttggttga | tattttcgat | 900 |
| gctggtactg | ataccactgc | ttctactttg | aatgggcta | tggctgaatt | ggttagaaat | 960 |
| ccagaaatga | tgaccaaggt | ccagaacgaa | attgaacaag | ctattggtaa | gaactgcgcc | 1020 |
| accattcaag | aatctgatat | tccaaaattg | ccatacttgc | aggccatcat | caaagaaact | 1080 |
| ttgagattgc | atccaccaac | cgtcttttttg | ttgccaagaa | aagcagatgt | tgatgtcgag | 1140 |
| ttgtacggtt | atgttgttcc | aaagaacgca | caagttttgg | ttaacttgtg | ggctataggt | 1200 |
| agagatccaa | aggtttggaa | gaactccgaa | gttttttcac | cagaaagatt | cttggattgc | 1260 |
| gacatcgatt | ataagggtag | agattttgag | ttgttgccat | tggtgctgg | tagaagaatt | 1320 |
| tgtccaggtt | tgactttggc | atacaggatg | ttgaacttaa | tgatgggtaa | cttcttgcac | 1380 |
| tccttcgatt | ggaaattgga | agatggtatg | tctccaaagg | acttggatat | ggacgaaaag | 1440 |
| tttggtatca | ccttgcaaaa | ggttaagcca | ttgcaagtta | ttcccgttcc | aaagtga | 1497 |

<210> SEQ ID NO 48
<211> LENGTH: 498
<212> TYPE: PRT
<213> ORGANISM: Spinacia oleracea

<400> SEQUENCE: 48

Met Glu Asn Thr Thr Leu Ala Phe Ile Leu Ser Ile Ser Phe Val Cys
1               5                   10                  15

-continued

```
Phe His Val Ile Arg Ser Phe Ile Ser Lys Ala Arg Ser Lys Ser Ser
             20                  25                  30
Lys Leu Pro Pro Gly Pro Lys Arg Met Pro Ile Phe Gly Asn Ile Phe
         35                  40                  45
Asp Leu Gly Glu Lys Pro His Arg Ser Phe Ala Asn Leu Ser Lys Ile
     50                  55                  60
His Gly Pro Leu Ile Ser Leu Lys Leu Gly Ser Ile Thr Thr Ile Val
 65                  70                  75                  80
Val Ser Ser Ala Asp Val Ala Lys Glu Met Phe Leu Lys Asn Asp Gln
                 85                  90                  95
Ala Leu Ala Asn Arg Thr Ile Pro Asp Ser Val Arg Ala Gly Asp His
             100                 105                 110
Asp Lys Leu Ser Ile Ser Trp Leu Pro Val Ser Ala Lys Trp Arg Asn
         115                 120                 125
Leu Arg Lys Ile Ser Ala Val Gln Leu Leu Ser Asn Gln Arg Leu Asp
     130                 135                 140
Ala Ser Gln Ala His Arg Gln Ala Lys Val Glu Gln Leu Leu Thr Tyr
145                 150                 155                 160
Val Lys Asp Cys Ser Lys Lys Gly Leu Pro Val Asp Ile Gly Arg Ala
                 165                 170                 175
Ala Phe Thr Thr Ser Leu Asn Leu Leu Ser Asn Thr Phe Phe Ser Val
             180                 185                 190
Glu Leu Ala Ser His Glu Ser Ser Ala Ser Gln Glu Phe Lys Gln Leu
         195                 200                 205
Met Trp Asn Ile Met Glu Glu Ile Gly Lys Pro Asn Tyr Ala Asp Tyr
     210                 215                 220
Phe Pro Ile Leu Gly Tyr Val Asp Pro Phe Gly Ile Arg Arg Arg Leu
225                 230                 235                 240
Ala Ala Tyr Phe Asp Gln Leu Ile Ala Val Phe Gln Asp Ile Ile Gln
                 245                 250                 255
Lys Arg Gln Lys Ile Arg Ser Thr Asn Gly Ala Lys Gln Thr Asn Asp
             260                 265                 270
Ile Leu Asp Thr Leu Leu Asn Leu His Glu Glu Asn Glu Leu Ser Met
         275                 280                 285
Gly Glu Ile Asn His Leu Leu Val Asp Ile Phe Asp Ala Gly Thr Asp
     290                 295                 300
Thr Thr Ala Ser Thr Leu Glu Trp Ala Met Ala Glu Leu Val Arg Asn
305                 310                 315                 320
Pro Glu Met Met Thr Lys Val Gln Asn Glu Ile Glu Gln Ala Ile Gly
                 325                 330                 335
Lys Asn Cys Ala Thr Ile Gln Glu Ser Asp Ile Pro Lys Leu Pro Tyr
             340                 345                 350
Leu Gln Ala Ile Ile Lys Glu Thr Leu Arg Leu His Pro Pro Thr Val
         355                 360                 365
Phe Leu Leu Pro Arg Lys Ala Asp Val Asp Val Glu Leu Tyr Gly Tyr
     370                 375                 380
Val Val Pro Lys Asn Ala Gln Val Leu Val Asn Leu Trp Ala Ile Gly
385                 390                 395                 400
Arg Asp Pro Lys Val Trp Lys Asn Ser Glu Val Phe Ser Pro Glu Arg
                 405                 410                 415
Phe Leu Asp Cys Asp Ile Asp Tyr Lys Gly Arg Asp Phe Glu Leu Leu
             420                 425                 430
Pro Phe Gly Ala Gly Arg Arg Ile Cys Pro Gly Leu Thr Leu Ala Tyr
```

```
          435                 440                 445
Arg Met Leu Asn Leu Met Met Gly Asn Phe Leu His Ser Phe Asp Trp
    450                 455                 460

Lys Leu Glu Asp Gly Met Ser Pro Lys Asp Leu Asp Met Asp Glu Lys
465                 470                 475                 480

Phe Gly Ile Thr Leu Gln Lys Val Lys Pro Leu Gln Val Ile Pro Val
                485                 490                 495

Pro Lys

<210> SEQ ID NO 49
<211> LENGTH: 1503
<212> TYPE: DNA
<213> ORGANISM: Chenopodium quinoa

<400> SEQUENCE: 49
atggactcta ccaccttggt tatggttgtc atttccatct tgttcgtgtt cttgtaccac     60
gtcaagtcat tcttcatcag gtacttctct aatagattgc caccaggtcc aaaacctaag    120 ccaattttg gtaacatctt cgacttgggt gaaaagccac atagatcttt tgctaacttg    180
gctaagattt tcggtccctt gatttctttg aagttgggta atgttactac cgtcgttgtc    240
tcttcttcat acgttgctga agaaatgttc ttgaagaacg atcaatcctt cgccaacaga    300
actattccag attctgttag agctggtaac cacgataagt tgtctatgtc ttggttgcca    360
atttctccac aatggcgtaa cttgagaaag atttccgctg tccaattatt gtctacccaa    420
agattggatg cttcccaagc tttgagacaa gctaaagttt ctcaattgca tgcctacgtt    480
caagactgtt ctaaaaagtt gcaaccagtc aacattggta gagctgcttt tactacttcc    540
ctgaacttgt tgtctaacac cttcttctct attgaattgg cctctcatga atcctctacc    600
tctcaagaat tcaagcaatt gatgtggaac atcatggaag aaatcggtag accaaattac    660
gctgattact tcccaatctt gggttacatt gatccattcg gtatcagaag aagattggct    720
tcttacttcg atgaactgat cgtcgttttc caaaacatca tttgcgaaag cagaacatc    780 agatcctctg atgattcttc tgctaagcac actaacgatg tcttggatac tttgttgaac    840
ctgtacgaca agaacgaatt gtctatggac gaaatcaacc acttgttggt tgatattttc    900
aacgctggta ctgataccac tgcttctact ttggaatgga ctatgaccga gttgattaag    960
aacccaaagt ccatgattat ctgccagaac gaaattgaac aagccttagg taaaggctcc   1020
ttgtccattc aagaatccga tatttctaag ctgccatact tgcaagccat tatgaaggaa   1080
actttgagat tgcatccacc aaccgttttt tgttgccaa gaaaagctga ttccgatgtt   1140
gaattgtgtg gttacgttgt tcctaaacat gcccaagttt tggttaactt gtgggctata   1200
ggtagagatc caaggtttg ggaaaatcca gaagttttct caccagaaag attcttggat   1260
tgcgaaattg acttgaaggg tcaagatttt gagttgttgc catttggtgc tggtagaaga   1320
atttgtccag gtttgaattt ggcctacagg atgttgaact tgatgttggc tactctgttg   1380
cataactaca actggaaatt ggaagatggc atgaccttga cgatttggga tatggatgag   1440
aagttcggta ttaccttgca aaaggttaag ccattgcaag ttgttccaat tccaaggtac   1500
tga                                                                 1503

<210> SEQ ID NO 50
<211> LENGTH: 500
<212> TYPE: PRT
<213> ORGANISM: Chenopodium quinoa
```

<400> SEQUENCE: 50

```
Met Asp Ser Thr Thr Leu Val Met Val Ile Ser Ile Leu Phe Val
1               5                   10                  15

Phe Leu Tyr His Val Lys Ser Phe Phe Ile Arg Tyr Phe Ser Asn Arg
            20                  25                  30

Leu Pro Pro Gly Pro Lys Pro Lys Pro Ile Phe Gly Asn Ile Phe Asp
            35                  40                  45

Leu Gly Glu Lys Pro His Arg Ser Phe Ala Asn Leu Ala Lys Ile Phe
        50                  55                  60

Gly Pro Leu Ile Ser Leu Lys Leu Gly Asn Val Thr Thr Val Val
65                  70                  75                  80

Ser Ser Ser Tyr Val Ala Glu Glu Met Phe Leu Lys Asn Asp Gln Ser
                85                  90                  95

Phe Ala Asn Arg Thr Ile Pro Asp Ser Val Arg Ala Gly Asn His Asp
            100                 105                 110

Lys Leu Ser Met Ser Trp Leu Pro Ile Ser Pro Gln Trp Arg Asn Leu
            115                 120                 125

Arg Lys Ile Ser Ala Val Gln Leu Leu Ser Thr Gln Arg Leu Asp Ala
        130                 135                 140

Ser Gln Ala Leu Arg Gln Ala Lys Val Ser Gln Leu His Ala Tyr Val
145                 150                 155                 160

Gln Asp Cys Ser Lys Lys Leu Gln Pro Val Asn Ile Gly Arg Ala Ala
                165                 170                 175

Phe Thr Thr Ser Leu Asn Leu Leu Ser Asn Thr Phe Phe Ser Ile Glu
            180                 185                 190

Leu Ala Ser His Glu Ser Ser Thr Ser Gln Glu Phe Lys Gln Leu Met
            195                 200                 205

Trp Asn Ile Met Glu Glu Ile Gly Arg Pro Asn Tyr Ala Asp Tyr Phe
    210                 215                 220

Pro Ile Leu Gly Tyr Ile Asp Pro Phe Gly Ile Arg Arg Arg Leu Ala
225                 230                 235                 240

Ser Tyr Phe Asp Glu Leu Ile Val Val Phe Gln Asn Ile Ile Cys Glu
                245                 250                 255

Arg Gln Asn Ile Arg Ser Ser Asp Asp Ser Ser Ala Lys His Thr Asn
            260                 265                 270

Asp Val Leu Asp Thr Leu Leu Asn Leu Tyr Asp Lys Asn Glu Leu Ser
            275                 280                 285

Met Asp Glu Ile Asn His Leu Leu Val Asp Ile Phe Asn Ala Gly Thr
        290                 295                 300

Asp Thr Thr Ala Ser Thr Leu Glu Trp Thr Met Thr Glu Leu Ile Lys
305                 310                 315                 320

Asn Pro Lys Ser Met Ile Ile Cys Gln Asn Glu Ile Glu Gln Ala Leu
                325                 330                 335

Gly Lys Gly Ser Leu Ser Ile Gln Glu Ser Asp Ile Ser Lys Leu Pro
            340                 345                 350

Tyr Leu Gln Ala Ile Met Lys Glu Thr Leu Arg Leu His Pro Pro Thr
            355                 360                 365

Val Phe Leu Leu Pro Arg Lys Ala Asp Ser Asp Val Glu Leu Cys Gly
        370                 375                 380

Tyr Val Val Pro Lys His Ala Gln Val Leu Val Asn Leu Trp Ala Ile
385                 390                 395                 400

Gly Arg Asp Pro Lys Val Trp Glu Asn Pro Glu Val Phe Ser Pro Glu
                405                 410                 415
```

```
Arg Phe Leu Asp Cys Glu Ile Asp Leu Lys Gly Gln Asp Phe Glu Leu
            420                 425                 430

Leu Pro Phe Gly Ala Gly Arg Arg Ile Cys Pro Gly Leu Asn Leu Ala
        435                 440                 445

Tyr Arg Met Leu Asn Leu Met Leu Ala Thr Leu Leu His Asn Tyr Asn
    450                 455                 460

Trp Lys Leu Glu Asp Gly Met Thr Leu Asn Asp Leu Asp Met Asp Glu
465                 470                 475                 480

Lys Phe Gly Ile Thr Leu Gln Lys Val Lys Pro Leu Gln Val Val Pro
                485                 490                 495

Ile Pro Arg Tyr
            500

<210> SEQ ID NO 51
<211> LENGTH: 1497
<212> TYPE: DNA
<213> ORGANISM: Spinacia oleracea

<400> SEQUENCE: 51
atggactaca ccaccttggt catcatcttg tctattatgt tcgtttgctt ccacctgttg      60 aagtctttt tcactactcc atcctctcat aagttgccac caggtccaaa acctattcca     120
attttcggta acatcttcta cttgggtgaa aagccacata gatcttttgc taacttggct     180
aagattcacg gtccattgat ttctttgaag ttgggttctg ttacgacgat cgttgtttct     240
tcttcatacg ttgctgaaga gatgttcttg aaacatgata gagctttcgc caacagaacc     300
attccagatt ctattagagc ttgcgatcac gacaaattgt ctatgtcttg gttgcccatt     360
tccttgaatt ggagaaactt gaggaagatc tcttccgttc agttgttgtc aatcaaaga     420 ttggatgctt ctcaagctca tagacaagct caagtcgaac aattattggc ttacgttcaa     480
gactgctcca ttaagggtat tccagttgat attggtagag ctgcttttac cacttccttg     540
aacttgttgt ctaacaccct tcttctctgt tgaattggcct ctcatgaatc ttcagcttcc     600
caagaattca agcaattgat gtggaacatc atggaagaaa tcggtaagcc aaattacgct     660
gattacttcc aatttttggc ctacgtagat ccatttggtg ttagaagaag attggctgcc     720
tacttcgacc aattgattga tgttttccag acatcatca aagagcgtca aaagatcaga     780
ttgaagaacg gttcatctgc caagcaaact aacgatattt ggacaccctt gttgaacttg     840
cacgacgaaa atgaattatc catgggtgaa atcaaccact gttggttga tattttcaac     900 gctggtactg ataccactgc ttctactttg aatgggcta tgactgaatt ggttagaaac     960
cctagaatca tgggtagagt tcaacacgaa attgaacaag ctttggaaaa ggactgctcc    1020
tctattcaag aagcctacat tttgaaactg ccatacttgc aggccattat caagaaact    1080 ttgagattgc atccaccaac cgtttttttg ttgccaagaa aggctaacat cgaagtcgaa    1140
ttgcatggtt ttactgttcc aaagaacgcc caaatcttgg ttaatttgtg ggctgttggt    1200
agagatccaa aggtttggga aaatcctaag gttttcatcc cagacagatt cttggaatgc    1260
gatattgatg ttaagggtca gaactttgag ttgttgcctt ttggtgctgg tagaagaatt    1320
tgtccaggtt gggtttagc ttacaggatg ttgaattga tcttggccac cttgatccat    1380
aactacgatt ggaaattgga ggatggtatg aacgttaacg atttggatat ggacgaaaag    1440
ttcggtatca ccttgcaaaa agttgttcca ttgaaggtta tccccgttcc aagataa      1497

<210> SEQ ID NO 52
```

<211> LENGTH: 498
<212> TYPE: PRT
<213> ORGANISM: Spinacia oleracea

<400> SEQUENCE: 52

```
Met Asp Tyr Thr Thr Leu Val Ile Ile Leu Ser Ile Met Phe Val Cys
1               5                   10                  15

Phe His Leu Leu Lys Ser Phe Phe Thr Thr Pro Ser Ser His Lys Leu
            20                  25                  30

Pro Pro Gly Pro Lys Pro Ile Pro Ile Phe Gly Asn Ile Phe Tyr Leu
        35                  40                  45

Gly Glu Lys Pro His Arg Ser Phe Ala Asn Leu Ala Lys Ile His Gly
    50                  55                  60

Pro Leu Ile Ser Leu Lys Leu Gly Ser Val Thr Thr Ile Val Val Ser
65                  70                  75                  80

Ser Ser Tyr Val Ala Glu Glu Met Phe Leu Lys His Asp Arg Ala Phe
                85                  90                  95

Ala Asn Arg Thr Ile Pro Asp Ser Ile Arg Ala Cys Asp His Asp Lys
            100                 105                 110

Leu Ser Met Ser Trp Leu Pro Ile Ser Leu Asn Trp Arg Asn Leu Arg
        115                 120                 125

Lys Ile Ser Ser Val Gln Leu Leu Ser Asn Gln Arg Leu Asp Ala Ser
    130                 135                 140

Gln Ala His Arg Gln Ala Gln Val Glu Gln Leu Leu Ala Tyr Val Gln
145                 150                 155                 160

Asp Cys Ser Ile Lys Gly Ile Pro Val Asp Ile Gly Arg Ala Ala Phe
                165                 170                 175

Thr Thr Ser Leu Asn Leu Leu Ser Asn Thr Phe Phe Ser Val Glu Leu
            180                 185                 190

Ala Ser His Glu Ser Ser Ala Ser Gln Glu Phe Lys Gln Leu Met Trp
        195                 200                 205

Asn Ile Met Glu Glu Ile Gly Lys Pro Asn Tyr Ala Asp Tyr Phe Pro
    210                 215                 220

Ile Leu Ala Tyr Val Asp Pro Phe Gly Val Arg Arg Arg Leu Ala Ala
225                 230                 235                 240

Tyr Phe Asp Gln Leu Ile Asp Val Phe Gln Asp Ile Ile Lys Glu Arg
                245                 250                 255

Gln Lys Ile Arg Leu Lys Asn Gly Ser Ser Ala Lys Gln Thr Asn Asp
            260                 265                 270

Ile Leu Asp Thr Leu Leu Asn Leu His Asp Glu Asn Glu Leu Ser Met
        275                 280                 285

Gly Glu Ile Asn His Leu Leu Val Asp Ile Phe Asn Ala Gly Thr Asp
    290                 295                 300

Thr Thr Ala Ser Thr Leu Glu Trp Ala Met Thr Glu Leu Val Arg Asn
305                 310                 315                 320

Pro Arg Ile Met Gly Arg Val Gln His Glu Ile Glu Gln Ala Leu Glu
                325                 330                 335

Lys Asp Cys Ser Ser Ile Gln Glu Ala Tyr Ile Leu Lys Leu Pro Tyr
            340                 345                 350

Leu Gln Ala Ile Ile Lys Glu Thr Leu Arg Leu His Pro Pro Thr Val
        355                 360                 365

Phe Leu Leu Pro Arg Lys Ala Asn Ile Glu Val Glu Leu His Gly Phe
    370                 375                 380

Thr Val Pro Lys Asn Ala Gln Ile Leu Val Asn Leu Trp Ala Val Gly
```

```
                385               390               395               400
Arg Asp Pro Lys Val Trp Glu Asn Pro Lys Val Phe Ile Pro Asp Arg
                405                   410                   415

Phe Leu Glu Cys Asp Ile Asp Val Lys Gly Gln Asn Phe Glu Leu Leu
                420                   425                   430

Pro Phe Gly Ala Gly Arg Arg Ile Cys Pro Gly Leu Gly Leu Ala Tyr
                435                   440                   445

Arg Met Leu Asn Leu Ile Leu Ala Thr Leu Ile His Asn Tyr Asp Trp
                450                   455                   460

Lys Leu Glu Asp Gly Met Asn Val Asn Asp Leu Asp Met Asp Glu Lys
465                   470                   475                   480

Phe Gly Ile Thr Leu Gln Lys Val Val Pro Leu Lys Val Ile Pro Val
                485                   490                   495

Pro Arg

<210> SEQ ID NO 53
<211> LENGTH: 1491
<212> TYPE: DNA
<213> ORGANISM: Mirabilis jalapa

<400> SEQUENCE: 53
atggacttct tgaccctggt catgatcttg tctattatct tcttcttcta caacctgctg      60
aagatgaagt tcactactca ttctgatgct caattgccac caggtccaaa acctatgcca     120 attttttggta acatcttcga gttgggtgaa agccacata gatcttttgc taacttggct      180
aaaactcacg gtccattgat gtctttgaga ttgggttctg ttactaccat cgttgtttca     240
tctgctgaag ttgccaaaga atgttcttg aagaacgatc aatccttggc cgatagatct      300
gttccaaatt ctgttacagc tggtgatcat cataagttga ctatgtcttg gttgccagtt     360
tctccaaagt ggaagaactt cagaaagatt accgctgttc atttgttgtc cccacaaaga     420
ttggatgctt gtcatgcttt gagacatgct aaagttaagc agttgtacga atacgttcaa     480
gaatgtgctt tgaagggtga agctgttgat attggtaaag ctgctttcac cacttccttg     540
aacttgttgt ctaacttgtt cttctccgtt gaattggcta accatacttc taacacctct     600
caagaattca agcaattgat ctgggacatc atggaagata tcggtaagcc aaaattacgct    660 gattacttcc ccttgttgaa atacgttgat ccatccggta ttagaagaag gttggctgct     720
aatttcgata gttgatcga cgttttccag tccttcatct ctaagagatt atcctctgct      780
tactcttctg ctacctcttt ggatgatgtt ttggatgtct tgttaagtt gttgaaagaa     840 aaagaactga acatgggcga atcaaccat tgttggttg atatttttga tgccggtact       900
gataccacct ctaatacttt tgaatgggct atggctgaat tgatgagaaa cccaattatg     960
atgaagagag cccaaaacga aattgccttg gttttgggta agataacgc caccattcaa     1020 gaatccgata ttgctaatat gccatacttg caggccatca tcaaagaaac attgagattg    1080
catccaccaa ccgttttttt gttgccaaga aaggctatta ccaacgtcaa gttgtatggt    1140
tacatcgttc caaagaacgc ccaaatcttg gttaatttgt gggctattgg tagagatcca    1200
aaggtttgga gaatccaaa cgaattcttg ccagataggt tcttgaactc tgatatcgat    1260 gttaaggta gagactttgg tttgttacca tttggtctg gtagaagaat tgtccaggt       1320 atgaatttgg cctacagaat gttgactttg atgttggcta ctctgttgca atctttcgat    1380
tggaagttgc ctcatagaaa ctctccattg gatttggata tggacgaaaa gtttggtatc    1440
gccttgcaaa aaactaagcc attggaaatc atcccactga tcaagtactg a            1491
```

<210> SEQ ID NO 54
<211> LENGTH: 496
<212> TYPE: PRT
<213> ORGANISM: Mirabilis jalapa

<400> SEQUENCE: 54

```
Met Asp Phe Leu Thr Leu Val Met Ile Leu Ser Ile Ile Phe Phe Phe
1               5                   10                  15

Tyr Asn Leu Leu Lys Met Lys Phe Thr Thr His Ser Asp Ala Gln Leu
            20                  25                  30

Pro Pro Gly Pro Lys Pro Met Pro Ile Phe Gly Asn Ile Phe Glu Leu
        35                  40                  45

Gly Glu Lys Pro His Arg Ser Phe Ala Asn Leu Ala Lys Thr His Gly
    50                  55                  60

Pro Leu Met Ser Leu Arg Leu Gly Ser Val Thr Thr Ile Val Val Ser
65                  70                  75                  80

Ser Ala Glu Val Ala Lys Glu Met Phe Leu Lys Asn Asp Gln Ser Leu
                85                  90                  95

Ala Asp Arg Ser Val Pro Asn Ser Val Thr Ala Gly Asp His His Lys
            100                 105                 110

Leu Thr Met Ser Trp Leu Pro Val Ser Pro Lys Trp Lys Asn Phe Arg
        115                 120                 125

Lys Ile Thr Ala Val His Leu Leu Ser Pro Gln Arg Leu Asp Ala Cys
    130                 135                 140

His Ala Leu Arg His Ala Lys Val Lys Gln Leu Tyr Glu Tyr Val Gln
145                 150                 155                 160

Glu Cys Ala Leu Lys Gly Glu Ala Val Asp Ile Gly Lys Ala Ala Phe
                165                 170                 175

Thr Thr Ser Leu Asn Leu Leu Ser Asn Leu Phe Phe Ser Val Glu Leu
            180                 185                 190

Ala Asn His Thr Ser Asn Thr Ser Gln Glu Phe Lys Gln Leu Ile Trp
        195                 200                 205

Asp Ile Met Glu Asp Ile Gly Lys Pro Asn Tyr Ala Asp Tyr Phe Pro
    210                 215                 220

Leu Leu Lys Tyr Val Asp Pro Ser Gly Ile Arg Arg Arg Leu Ala Ala
225                 230                 235                 240

Asn Phe Asp Lys Leu Ile Asp Val Phe Gln Ser Phe Ile Ser Lys Arg
                245                 250                 255

Leu Ser Ser Ala Tyr Ser Ser Thr Ser Leu Asp Asp Val Leu Asp
            260                 265                 270

Val Leu Leu Lys Leu Leu Lys Glu Lys Glu Leu Asn Met Gly Glu Ile
    275                 280                 285

Asn His Leu Leu Val Asp Ile Phe Asp Ala Gly Thr Asp Thr Thr Ser
290                 295                 300

Asn Thr Phe Glu Trp Ala Met Ala Glu Leu Met Arg Asn Pro Ile Met
305                 310                 315                 320

Met Lys Arg Ala Gln Asn Glu Ile Ala Leu Val Leu Gly Lys Asp Asn
                325                 330                 335

Ala Thr Ile Gln Glu Ser Asp Ile Ala Asn Met Pro Tyr Leu Gln Ala
            340                 345                 350

Ile Ile Lys Glu Thr Leu Arg Leu His Pro Pro Thr Val Phe Leu Leu
        355                 360                 365

Pro Arg Lys Ala Ile Thr Asn Val Lys Leu Tyr Gly Tyr Ile Val Pro
```

| | | | | | | | | | | | | |
|---|---|---|---|---|---|---|---|---|---|---|---|---|
| | | 370 | | | | 375 | | | | 380 | | |
| Lys | Asn | Ala | Gln | Ile | Leu | Val | Asn | Leu | Trp | Ala | Ile | Gly | Arg | Asp | Pro |
| 385 | | | | | 390 | | | | | 395 | | | | | 400 |

Lys Asn Ala Gln Ile Leu Val Asn Leu Trp Ala Ile Gly Arg Asp Pro
385             390              395              400

Lys Val Trp Lys Asn Pro Asn Glu Phe Leu Pro Asp Arg Phe Leu Asn
            405              410              415

Ser Asp Ile Asp Val Lys Gly Arg Asp Phe Gly Leu Leu Pro Phe Gly
            420              425              430

Ala Gly Arg Arg Ile Cys Pro Gly Met Asn Leu Ala Tyr Arg Met Leu
            435              440              445

Thr Leu Met Leu Ala Thr Leu Leu Gln Ser Phe Asp Trp Lys Leu Pro
450              455              460

His Arg Asn Ser Pro Leu Asp Leu Asp Met Asp Glu Lys Phe Gly Ile
465              470              475              480

Ala Leu Gln Lys Thr Lys Pro Leu Glu Ile Ile Pro Leu Ile Lys Tyr
            485              490              495

<210> SEQ ID NO 55
<211> LENGTH: 1491
<212> TYPE: DNA
<213> ORGANISM: Mirabilis multiflora

<400> SEQUENCE: 55

| | | |
|---|---|---|
| atggacttct tgaccctggt catgatcttg tctatgatct tcttcttcta caacctgctg | 60 |
| aagatgattt tcactaccca ttctgatgct caattgccac caggtccaaa acctatgcca | 120 |
| attttggta acatcttcga gttgggtgaa aagccacata gatcttttgc taacttggct | 180 |
| aaaactcacg gtccattgat gtctttgaga ttgggtagag ttactaccat cgttgtttca | 240 |
| tctgctgaag ttgccaaaga aatgttcttg aagaacgatc aatccttggc cgatagatct | 300 |
| gttccaaatt ctgttactgc tggtgatcat cataagttga ctatgtcttg gttgccagtt | 360 |
| tctccaaagt ggaagaactt cagaaagatt accgctgttc atttgttgtc cccacaaaga | 420 |
| ttggatgctt gtaatgcttt gagacatgct aaggttaagc agttgtacga atacgttcaa | 480 |
| gaatgtgctt tgaagggtga agctgttgat attggtaaag ctgctttcac cacttccttg | 540 |
| aacttgttgt ctaacttgtt cttctccgtt gaattggcta accatacttc taacacctct | 600 |
| caagaattca agcaattgat ctgggacatc atggaagata tcggtaagcc aaattacgct | 660 |
| gattacttcc ccttgttgaa atacgttgat ccatccggta ttagaagaag gttggctgct | 720 |
| aatttcgata gttgatcga cgttttccag tccttcatct gtaagagatt atcctctgct | 780 |
| tactcttctg ctacctcttt ggatgatgtt ttggatgtct tgttgaagct gtacaaagaa | 840 |
| aaagaattga acatgggcga gatcaaccac ttgttggttg atatttttga tgccggtact | 900 |
| gataccacct ctaatacttt tgaatgggcc atgtccgaat tgattagaaa cccaactatg | 960 |
| atgaagagag cccaaaacga aattgctttg gttttgggta agataacgg caccattcaa | 1020 |
| gaatccgata ttgctaatat gccatacttg caggccatca tcaaagaaac attgagattg | 1080 |
| catccaccaa ccgttttttt gttgccaaga aaggctatta cctacgtcaa gttgtatggt | 1140 |
| tacatcgttc aaagaacgc ccaaatcttg gttaatttgt gggctattgg tagagatcca | 1200 |
| aaggtttgga gaatccaaa cgaattcttg ccagatagg tcttgaactc tgatatcgat | 1260 |
| gttaagggta gagctttgg tttgttacca tttggtgctg gtagaagaat ttgtccaggt | 1320 |
| atgaatttgg cctacagaat gttgactttg atgttggcta ctctgttgca atctttcgat | 1380 |
| tggaaattgc cacatggtaa ctctccaatg gatttggata tggacgaaaa gtttggtatc | 1440 |

```
gccttgcaaa aaactaagcc cttggaaatt atccccgtca tcaagtacta a            1491
```

<210> SEQ ID NO 56
<211> LENGTH: 496
<212> TYPE: PRT
<213> ORGANISM: Mirabilis multiflora

<400> SEQUENCE: 56

```
Met Asp Phe Leu Thr Leu Val Met Ile Leu Ser Met Ile Phe Phe Phe
1               5                   10                  15

Tyr Asn Leu Leu Lys Met Ile Phe Thr Thr His Ser Asp Ala Gln Leu
            20                  25                  30

Pro Pro Gly Pro Lys Pro Met Pro Ile Phe Gly Asn Ile Phe Glu Leu
        35                  40                  45

Gly Glu Lys Pro His Arg Ser Phe Ala Asn Leu Ala Lys Thr His Gly
    50                  55                  60

Pro Leu Met Ser Leu Arg Leu Gly Arg Val Thr Thr Ile Val Val Ser
65                  70                  75                  80

Ser Ala Glu Val Ala Lys Glu Met Phe Leu Lys Asn Asp Gln Ser Leu
                85                  90                  95

Ala Asp Arg Ser Val Pro Asn Ser Val Thr Ala Gly Asp His His Lys
            100                 105                 110

Leu Thr Met Ser Trp Leu Pro Val Ser Pro Lys Trp Lys Asn Phe Arg
        115                 120                 125

Lys Ile Thr Ala Val His Leu Leu Ser Pro Gln Arg Leu Asp Ala Cys
130                 135                 140

Asn Ala Leu Arg His Ala Lys Val Lys Gln Leu Tyr Glu Tyr Val Gln
145                 150                 155                 160

Glu Cys Ala Leu Lys Gly Glu Ala Val Asp Ile Gly Lys Ala Ala Phe
                165                 170                 175

Thr Thr Ser Leu Asn Leu Leu Ser Asn Leu Phe Phe Ser Val Glu Leu
            180                 185                 190

Ala Asn His Thr Ser Asn Thr Ser Gln Glu Phe Lys Gln Leu Ile Trp
        195                 200                 205

Asp Ile Met Glu Asp Ile Gly Lys Pro Asn Tyr Ala Asp Tyr Phe Pro
    210                 215                 220

Leu Leu Lys Tyr Val Asp Pro Ser Gly Ile Arg Arg Arg Leu Ala Ala
225                 230                 235                 240

Asn Phe Asp Lys Leu Ile Asp Val Phe Gln Ser Phe Ile Cys Lys Arg
                245                 250                 255

Leu Ser Ser Ala Tyr Ser Ser Ala Thr Ser Leu Asp Asp Val Leu Asp
            260                 265                 270

Val Leu Leu Lys Leu Tyr Lys Glu Lys Glu Leu Asn Met Gly Glu Ile
        275                 280                 285

Asn His Leu Leu Val Asp Ile Phe Asp Ala Gly Thr Asp Thr Thr Ser
    290                 295                 300

Asn Thr Phe Glu Trp Ala Met Ser Glu Leu Ile Arg Asn Pro Thr Met
305                 310                 315                 320

Met Lys Arg Ala Gln Asn Glu Ile Ala Leu Val Leu Gly Lys Asp Asn
                325                 330                 335

Gly Thr Ile Gln Glu Ser Asp Ile Ala Asn Met Pro Tyr Leu Gln Ala
            340                 345                 350

Ile Ile Lys Glu Thr Leu Arg Leu His Pro Pro Thr Val Phe Leu Leu
        355                 360                 365
```

```
Pro Arg Lys Ala Ile Thr Tyr Val Lys Leu Tyr Gly Tyr Ile Val Pro
    370             375                 380

Lys Asn Ala Gln Ile Leu Val Asn Leu Trp Ala Ile Gly Arg Asp Pro
385                 390                 395                 400

Lys Val Trp Lys Asn Pro Asn Glu Phe Leu Pro Asp Arg Phe Leu Asn
                405                 410                 415

Ser Asp Ile Asp Val Lys Gly Arg Asp Phe Gly Leu Leu Pro Phe Gly
                420                 425                 430

Ala Gly Arg Arg Ile Cys Pro Gly Met Asn Leu Ala Tyr Arg Met Leu
                435                 440                 445

Thr Leu Met Leu Ala Thr Leu Leu Gln Ser Phe Asp Trp Lys Leu Pro
    450                 455                 460

His Gly Asn Ser Pro Met Asp Leu Asp Met Asp Glu Lys Phe Gly Ile
465                 470                 475                 480

Ala Leu Gln Lys Thr Lys Pro Leu Glu Ile Ile Pro Val Ile Lys Tyr
                485                 490                 495
```

<210> SEQ ID NO 57
<211> LENGTH: 1500
<212> TYPE: DNA
<213> ORGANISM: Beta vulgaris

<400> SEQUENCE: 57

```
atggatcatg ctaccttggc tatgattttg gccatcttgt tcattagctt ccacttcatc    60
aagctgttgt tctctcaaca aactaccaag ttgttgccac caggtccaaa accattgcca   120
attattggta acatcttgga ggttggtaag aagccacata gatcttttgc taatttggcc   180
aagattcacg gtccattgat ttctttgaga ttgggttctg ttacgaccat cgttgtttct   240
tcagctgatg ttgctaaaga gatgttcttg aagaaggatc acccattgtc caacagaact   300
attccaaatt ctgttaccgc tggtgatcat cataagttga ctatgtcttg gttgccagtt   360
tctccaaagt ggcgtaattt cagaaagatt accgctgttc atttgttgtc cccacaaaga   420
ttggatgctt gtcaaacttt tagacacgct aaggttcaac agttgtacga atacgttcaa   480
gaatgtgctc aaaaaggtca agccgttgat attggtaaag ctgcttttac tacctccttg   540
aacttgctgt ctaagttgtt cttctctgtt gaattggctc atcacaagtc tcatacctct   600
caagaattca agagctgat ctggaacatc atggaagata tcggtaagcc aaattacgct   660
gattacttcc aatttgggg ttgcgttgat ccatctggta ttagaagaag attggcttgc   720
tctttcgata gttgattgc tgttttccaa ggtatcatct gtgaaagatt agccccagat   780
tcttctacta ctacaactac taccactgat gatgttttgg atgtgttgtt gcagttgttc   840
aagcaaaacg aattgaccat gggtgaaatc aaccacttgt tggttgatat tttcgatgct   900
ggtactgata ccacttcctc tactttggaa tgggttatga ccgaattgat cagaaaccca   960
gaaatgatgg aaaaggccca agaagagatt aagcaagttt gggtaaaga caagcagatc  1020
caagaatccg atattatcaa cttgccatac ttgcaggcca tcatcaaaga acattgaga  1080
ttgcatccac caaccgtttt tttgttgcca agaaaagctg ataccgatgt tgagttgtat  1140
ggttacatcg ttccaaagga tgcccaaatc ttggttaatt tgtgggctat ggtagagat  1200
ccaaatgctt ggcaaaacgc cgatattttc tcaccagaaa ggttcattgg ttgcgaaatt  1260
gatgttaagg gtagagactt tggtttgttg ccttttggtg ctggtagaag gatttgtcca  1320
ggtatgaatt tggctatcag aatgttgact ttgatgctgg ctactctgtt gcaattttc  1380
aactggaaat tggagggtga catctcacca aaagatttgg atatggacga aaagttcggt  1440
```

```
atcgccttgc aaaaaactaa gccattgaag ttgatcccca ttcctagata cggttcttga    1500
```

<210> SEQ ID NO 58
<211> LENGTH: 499
<212> TYPE: PRT
<213> ORGANISM: Beta vulgaris

<400> SEQUENCE: 58

```
Met Asp His Ala Thr Leu Ala Met Ile Leu Ala Ile Leu Phe Ile Ser
1               5                   10                  15

Phe His Phe Ile Lys Leu Leu Phe Ser Gln Gln Thr Thr Lys Leu Leu
            20                  25                  30

Pro Pro Gly Pro Lys Pro Leu Pro Ile Ile Gly Asn Ile Leu Glu Val
        35                  40                  45

Gly Lys Lys Pro His Arg Ser Phe Ala Asn Leu Ala Lys Ile His Gly
50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
        275                 280                 285

Glu Ile Asn His Leu Leu Val Asp Ile Phe Asp Ala Gly Thr Asp Thr
290                 295                 300

Thr Ser Ser Thr Leu Glu Trp Val Met Thr Glu Leu Ile Arg Asn Pro
305                 310                 315                 320

Glu Met Met Glu Lys Ala Gln Glu Ile Lys Gln Val Leu Gly Lys
                325                 330                 335

Asp Lys Gln Ile Gln Glu Ser Asp Ile Ile Asn Leu Pro Tyr Leu Gln
            340                 345                 350

Ala Ile Ile Lys Glu Thr Leu Arg Leu His Pro Pro Thr Val Phe Leu
        355                 360                 365
```

```
Leu Pro Arg Lys Ala Asp Thr Asp Val Glu Leu Tyr Gly Tyr Ile Val
        370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415

Gly Cys Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
    450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr Gly Ser

<210> SEQ ID NO 59
<211> LENGTH: 1419
<212> TYPE: DNA
<213> ORGANISM: Origin unknown

<400> SEQUENCE: 59
atgaccccag aacaattcag acaatacggt caccaattga ttgatttgat cgccgattac    60
agacaaaccg ttggtgaaag accagttatg gctcaagttg aaccaggtta tttgaaagct   120
gctttgccag ctactgctcc acaacaaggt gaaccatttg ctgctatttt ggatgatgtt   180
aacaacttgg ttatgccagg tttgtctcat ggcaacatc cagattttta cggttacttt   240
ccatccaacg gtactttgtc atctgttttg ggtgatttct gtctactgg tttgggtgtt   300 ttaggtttgt catggcaatc ttctccagct ttgtcagaat ggaagaaac tactttggat   360 tggttgagac agttgttggg tttatctggt caatggtctg gtgttattca agatactgct   420
tctacttcta ccttggttgc tttgattcct gctagagaaa gagctactga ttacgctttg   480
gttagaggtg gtttacaagc tgaacctaaa ccattgatcg tttacgtttc tgctcatgcc   540
cattcttcag ttgataaggc tgctttgttg gctggttttg gtagagataa cattagattg   600
attccaaccg acgaaagata cgccttaaga ccagaagctt acaagcagc tattgaacaa   660 gatttggctg ctggtaatca accatgtgct gttgttgcta ctactggtac tactactaca   720
actgctttgg atccattaag acctgtaggt gaaattgctc aagctaatgg tttgtggttg   780
catgttgatt cagctatggc tggttctgct atgattttgc agaatgtag atggatgtgg   840 gatggtattg aattggctga ttctgttgtt gttaacgccc ataagtggtt gggtgttgct   900
tttgattgct ctatctacta cgttagagat ccacaacact tgatcagagt catgtctact   960
aatccatcct acttgcaatc tgctgttgat ggtgaagtta agaacttgag agattgggt   1020 attccattgg gtagaagatt cagagctttg aagttgtggt ttatgttgag atccgaaggt  1080
gttgatgcat gcaagctag attgagaaga gatttggata tgctcaatg gttggctgga  1140 caagttgaag ctgctgctga atgggaagtt ttggctccag ttcaattgca aaccttgtgc  1200
attagacata gaccagcagg tttggaaggt gaagctttgg atgctcatac aaaaggttgg  1260
gctgaaagat tgaatgcttc tggtgctgct tatgttactc cagctacttt agatggaaga  1320
```

-continued

```
tggatggtta gagtttccat tggtgcttta ccaactgaaa gaggtgacgt tcaaagattg    1380
tgggctagat tacaagatgt catcaaaggt ggttcctaa                           1419
```

<210> SEQ ID NO 60
<211> LENGTH: 472
<212> TYPE: PRT
<213> ORGANISM: Origin unknown

<400> SEQUENCE: 60

```
Met Thr Pro Glu Gln Phe Arg Gln Tyr Gly His Gln Leu Ile Asp Leu
1               5                   10                  15

Ile Ala Asp Tyr Arg Gln Thr Val Gly Glu Arg Pro Val Met Ala Gln
            20                  25                  30

Val Glu Pro Gly Tyr Leu Lys Ala Ala Leu Pro Ala Thr Ala Pro Gln
        35                  40                  45

Gln Gly Glu Pro Phe Ala Ala Ile Leu Asp Asp Val Asn Asn Leu Val
    50                  55                  60

Met Pro Gly Leu Ser His Trp Gln His Pro Asp Phe Tyr Gly Tyr Phe
65                  70                  75                  80

Pro Ser Asn Gly Thr Leu Ser Ser Val Leu Gly Asp Phe Leu Ser Thr
                85                  90                  95

Gly Leu Gly Val Leu Gly Leu Ser Trp Gln Ser Ser Pro Ala Leu Ser
            100                 105                 110

Glu Leu Glu Glu Thr Thr Leu Asp Trp Leu Arg Gln Leu Leu Gly Leu
        115                 120                 125

Ser Gly Gln Trp Ser Gly Val Ile Gln Asp Thr Ala Ser Thr Ser Thr
    130                 135                 140

Leu Val Ala Leu Ile Ser Ala Arg Glu Arg Ala Thr Asp Tyr Ala Leu
145                 150                 155                 160

Val Arg Gly Gly Leu Gln Ala Glu Pro Lys Pro Leu Ile Val Tyr Val
                165                 170                 175

Ser Ala His Ala His Ser Ser Val Asp Lys Ala Ala Leu Leu Ala Gly
            180                 185                 190

Phe Gly Arg Asp Asn Ile Arg Leu Ile Pro Thr Asp Glu Arg Tyr Ala
        195                 200                 205

Leu Arg Pro Glu Ala Leu Gln Ala Ala Ile Glu Gln Asp Leu Ala Ala
    210                 215                 220

Gly Asn Gln Pro Cys Ala Val Val Ala Thr Thr Gly Thr Thr Thr Thr
225                 230                 235                 240

Thr Ala Leu Asp Pro Leu Arg Pro Val Gly Glu Ile Ala Gln Ala Asn
                245                 250                 255

Gly Leu Trp Leu His Val Asp Ser Ala Met Ala Gly Ser Ala Met Ile
            260                 265                 270

Leu Pro Glu Cys Arg Trp Met Trp Asp Gly Ile Glu Leu Ala Asp Ser
        275                 280                 285

Val Val Val Asn Ala His Lys Trp Leu Gly Val Ala Phe Asp Cys Ser
    290                 295                 300

Ile Tyr Tyr Val Arg Asp Pro Gln His Leu Ile Arg Val Met Ser Thr
305                 310                 315                 320

Asn Pro Ser Tyr Leu Gln Ser Ala Val Asp Gly Glu Val Lys Asn Leu
                325                 330                 335

Arg Asp Trp Gly Ile Pro Leu Gly Arg Arg Phe Arg Ala Leu Lys Leu
            340                 345                 350

Trp Phe Met Leu Arg Ser Glu Gly Val Asp Ala Leu Gln Ala Arg Leu
```

```
            355                 360                 365
Arg Arg Asp Leu Asp Asn Ala Gln Trp Leu Ala Gly Gln Val Glu Ala
370                 375                 380

Ala Ala Glu Trp Glu Val Leu Ala Pro Val Gln Leu Gln Thr Leu Cys
385                 390                 395                 400

Ile Arg His Arg Pro Ala Gly Leu Glu Gly Ala Leu Asp Ala His
                405                 410                 415

Thr Lys Gly Trp Ala Glu Arg Leu Asn Ala Ser Gly Ala Ala Tyr Val
            420                 425                 430

Thr Pro Ala Thr Leu Asp Gly Arg Trp Met Val Arg Val Ser Ile Gly
            435                 440                 445

Ala Leu Pro Thr Glu Arg Gly Asp Val Gln Arg Leu Trp Ala Arg Leu
        450                 455                 460

Gln Asp Val Ile Lys Gly Gly Ser
465                 470

<210> SEQ ID NO 61
<211> LENGTH: 196
<212> TYPE: PRT
<213> ORGANISM: C. Japonica

<400> SEQUENCE: 61

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Gly Glu Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190

Lys Ser Ser Glu
        195

<210> SEQ ID NO 62
<211> LENGTH: 346
<212> TYPE: PRT
<213> ORGANISM: P. somniferum

<400> SEQUENCE: 62

Met Glu Thr Val Ser Lys Ile Asp Gln Gln Asn Gln Ala Lys Ile Trp
```

-continued

```
1               5                   10                  15
Lys Gln Ile Tyr Gly Phe Ala Glu Ser Leu Val Leu Lys Cys Ala Val
                20                  25                  30
Gln Leu Glu Ile Ala Glu Thr Leu His Asn Asn Val Lys Pro Met Ser
                35                  40                  45
Leu Ser Glu Leu Ala Ser Lys Leu Pro Val Ala Gln Pro Val Asn Glu
        50                  55                  60
Asp Arg Leu Phe Arg Ile Met Arg Tyr Leu Val His Met Glu Leu Phe
65                  70                  75                  80
Lys Ile Asp Ala Thr Thr Gln Lys Tyr Ser Leu Ala Pro Pro Ala Lys
                85                  90                  95
Tyr Leu Leu Arg Gly Trp Glu Lys Ser Met Val Asp Ser Ile Leu Cys
                100                 105                 110
Ile Asn Asp Lys Asp Phe Leu Ala Pro Trp His His Leu Gly Asp Gly
                115                 120                 125
Leu Thr Gly Asn Cys Asp Ala Phe Glu Lys Ala Leu Gly Lys Ser Ile
        130                 135                 140
Trp Val Tyr Met Ser Val Asn Pro Glu Lys Asn Gln Leu Phe Asn Ala
145                 150                 155                 160
Ala Met Ala Cys Asp Thr Arg Leu Val Thr Ser Ala Leu Ala Asn Glu
                165                 170                 175
Cys Lys Ser Ile Phe Ser Asp Gly Ile Ser Thr Leu Val Asp Val Gly
                180                 185                 190
Gly Gly Thr Gly Thr Ala Val Lys Ala Ile Ser Lys Ala Phe Pro Asp
                195                 200                 205
Ile Lys Cys Thr Ile Tyr Asp Leu Pro His Val Ile Ala Asp Ser Pro
210                 215                 220
Glu Ile Pro Asn Ile Thr Lys Ile Ser Gly Asp Met Phe Lys Ser Ile
225                 230                 235                 240
Pro Ser Ala Asp Ala Ile Phe Met Lys Cys Ile Leu His Asp Trp Asn
                245                 250                 255
Asp Asp Glu Cys Ile Gln Ile Leu Lys Arg Cys Lys Glu Ala Leu Pro
                260                 265                 270
Lys Gly Gly Lys Val Ile Ile Val Asp Val Val Ile Asp Met Asp Ser
                275                 280                 285
Thr His Pro Tyr Ala Lys Ile Arg Leu Thr Leu Asp Leu Asp Met Met
                290                 295                 300
Leu Asn Thr Gly Gly Lys Glu Arg Thr Lys Glu Glu Trp Lys Thr Leu
305                 310                 315                 320
Phe Asp Ala Ala Gly Phe Ala Ser His Lys Val Thr Gln Ile Ser Ala
                325                 330                 335
Val Gln Ser Val Ile Glu Ala Tyr Pro Tyr
                340                 345

<210> SEQ ID NO 63
<211> LENGTH: 350
<212> TYPE: PRT
<213> ORGANISM: P. somniferum

<400> SEQUENCE: 63

Met Gln Leu Lys Ala Lys Glu Glu Leu Leu Arg Asn Met Glu Leu Gly
1               5                   10                  15
Leu Ile Pro Asp Gln Glu Ile Arg Gln Leu Ile Arg Val Glu Leu Glu
                20                  25                  30
```

```
Lys Arg Leu Gln Trp Gly Tyr Lys Glu Thr His Glu Glu Gln Leu Ser
             35                  40                  45

Gln Leu Leu Asp Leu Val His Ser Leu Lys Gly Met Lys Met Ala Thr
 50                  55                  60

Glu Met Glu Asn Leu Asp Leu Lys Leu Tyr Glu Ala Pro Met Glu Phe
 65                  70                  75                  80

Leu Lys Ile Gln His Gly Ser Asn Met Lys Gln Ser Ala Gly Tyr Tyr
                 85                  90                  95

Thr Asp Glu Ser Thr Thr Leu Asp Glu Ala Glu Ile Ala Met Leu Asp
            100                 105                 110

Leu Tyr Met Glu Arg Ala Gln Ile Lys Asp Gly Gln Ser Val Leu Asp
            115                 120                 125

Leu Gly Cys Gly Leu Gly Ala Val Ala Leu Phe Gly Ala Asn Lys Phe
130                 135                 140

Lys Lys Cys Gln Phe Thr Gly Val Thr Ser Ser Val Glu Gln Lys Asp
145                 150                 155                 160

Tyr Ile Glu Gly Lys Cys Lys Glu Leu Lys Leu Thr Asn Val Lys Val
                165                 170                 175

Leu Leu Ala Asp Ile Thr Thr Tyr Glu Thr Glu Glu Arg Phe Asp Arg
            180                 185                 190

Ile Phe Ala Val Glu Leu Ile Glu His Met Lys Asn Tyr Gln Leu Leu
            195                 200                 205

Leu Lys Lys Ile Ser Glu Trp Met Lys Asp Asp Gly Leu Leu Phe Val
            210                 215                 220

Glu His Val Cys His Lys Thr Leu Ala Tyr His Tyr Glu Pro Val Asp
225                 230                 235                 240

Ala Glu Asp Trp Tyr Thr Asn Tyr Ile Phe Pro Ala Gly Thr Leu Thr
                245                 250                 255

Leu Ser Ser Ala Ser Met Leu Leu Tyr Phe Gln Asp Asp Val Ser Val
            260                 265                 270

Val Asn Gln Trp Thr Leu Ser Gly Lys His Tyr Ser Arg Ser His Glu
            275                 280                 285

Glu Trp Leu Lys Asn Met Asp Lys Asn Ile Val Glu Phe Lys Glu Ile
290                 295                 300

Met Arg Ser Ile Thr Lys Thr Glu Lys Glu Ala Ile Lys Leu Leu Asn
305                 310                 315                 320

Phe Trp Arg Ile Phe Cys Met Cys Gly Ala Glu Leu Phe Gly Tyr Lys
                325                 330                 335

Asn Gly Glu Glu Trp Met Leu Thr His Leu Leu Phe Lys Lys
            340                 345                 350

<210> SEQ ID NO 64
<211> LENGTH: 1613
<212> TYPE: DNA
<213> ORGANISM: E. californica
<220> FEATURE:
<221> NAME/KEY: misc_feature
<222> LOCATION: (612)..(612)
<223> OTHER INFORMATION: n is a, c, g, or t

<400> SEQUENCE: 64
aagtccgagt gagaagcaga gttagagaaa aaaaaaatgg aggttgtcac agtagcactt      60
attgcagtaa taattctttc aatactctac ctcctctttg gtagtagtgg tcacaaaaat     120
ctcccaccag gaccaaaacc atggccaata gtaggaaatc ttctccaact tggtgagaaa     180
ccacacgctc aattcgccga actagctcaa acctatggtg acattttcac tcttaaaatg     240
```

```
ggtactgaaa ctgtagttgt tgcatcaaca tcttcggcag cttccgaaat actaaaaacc      300
catgatcgaa ttctatccgc tcgttacgtt tttcaaagtt ttcgagtaaa agggcatgta      360
gaaaattcaa tagtttggtc agattgtact gaaacttgga agaatttaag aaaagtttgt      420
aggacggaac ttttcacaca gaagatgata gaaagtcaag ctcatgttag agagaaaaaa      480
tgtgaagaaa tggttgaata cttgatgaaa aaacaagggg aagaagtgaa aattgtggaa      540
gtaatatttg gaacattagt gaatatattc ggaaatttga tattttcaca gaatatattt      600
gaattgggtg anccaaatag tggaagttca gagttcaagg aatatctatg gaggatgttg      660
gaattaggga attcaacaaa tccagctgat tattttccaa tgttgggtaa atttgatttg      720
tttggacaga ggaaagaagt tgcagagtgt ttaaaaggga tttatgctat tgggggagct      780
atgcttcaag aaaggaaatt agctaaaaaa gttgatggat accaaagcaa gaatgatttt      840
gttgatgttt gtcttgattc tggacttaat gattatcaga tcaatgcctt gcttatggaa      900
ttatttgggg caggcacaga aacaagcgca tcgacaattg agtgggccat gactgaacta      960
acaaagaatc caaagataac agctaagctt agatcagaac ttcaaacagt ggtaggcgag     1020
agatcggtaa aagaatccga cttcccccaat cttccatacc ttgaagctac tgttaaagaa     1080
accctaagac ttcacccacc aactccattg ctactcccac gtcgagcact tgaaacctgt     1140
acaatcctca actacaccat cccaaaagat tgtcaaatta tggtcaacgc ttggggaatc     1200
ggacgtgatc ccaagacttg gatcgatccg ttgactttct caccagagag attcttgaat     1260
tctagtgttg actttagggg gaatgatttc agtttgatac catttggtgc aggaagaagg     1320
atatgccccg gtctgccaat agcaaatcag tttattgcat tgctagtggc aacatttgtg     1380
caaaatttgg attggtgtct accaaatggg atgagtgttg accatttgat agtggaggag     1440
aagtttgggt tgactcttca aaaagaacca cctctattca ttgttcctaa atcaagggtt     1500
tgatcttctc atcatggttc atgtgaaaac tagattatct attgtgaagg ctatgtatgt     1560
tttctttcct tcctataaaa aaaaaaaaaa aaaaaaaaaa aaaaaaaaaa aaa            1613
```

<210> SEQ ID NO 65
<211> LENGTH: 488
<212> TYPE: PRT
<213> ORGANISM: E. californica
<220> FEATURE:
<221> NAME/KEY: misc_feature
<222> LOCATION: (192)..(192)
<223> OTHER INFORMATION: Xaa can be any naturally occurring amino acid

<400> SEQUENCE: 65

Met Glu Val Val Thr Val Ala Leu Ile Ala Val Ile Ile Ser Ser Ile
1               5                   10                  15

Leu Tyr Leu Leu Phe Gly Ser Ser Gly His Lys Asn Leu Pro Pro Gly
            20                  25                  30

Pro Lys Pro Trp Pro Ile Val Gly Asn Leu Leu Gln Leu Gly Glu Lys
        35                  40                  45

Pro His Ala Gln Phe Ala Glu Leu Ala Gln Thr Tyr Gly Asp Ile Phe
    50                  55                  60

Thr Leu Lys Met Gly Thr Glu Thr Val Val Ala Ser Thr Ser
65                  70                  75                  80

Ala Ala Ser Glu Ile Leu Lys Thr His Asp Arg Ile Leu Ser Ala Arg
                85                  90                  95

Tyr Val Phe Gln Ser Phe Arg Val Lys Gly His Val Glu Asn Ser Ile
            100                 105                 110

```
Val Trp Ser Asp Cys Thr Glu Thr Trp Lys Asn Leu Arg Lys Val Cys
        115                 120                 125

Arg Thr Glu Leu Phe Thr Gln Lys Met Ile Glu Ser Gln Ala His Val
    130                 135                 140

Arg Glu Lys Lys Cys Glu Glu Met Val Glu Tyr Leu Met Lys Lys Gln
145                 150                 155                 160

Gly Glu Glu Val Lys Ile Val Glu Val Ile Phe Gly Thr Leu Val Asn
                165                 170                 175

Ile Phe Gly Asn Leu Ile Phe Ser Gln Asn Ile Phe Glu Leu Gly Xaa
            180                 185                 190

Pro Asn Ser Gly Ser Ser Glu Phe Lys Glu Tyr Leu Trp Arg Met Leu
        195                 200                 205

Glu Leu Gly Asn Ser Thr Asn Pro Ala Asp Tyr Phe Pro Met Leu Gly
    210                 215                 220

Lys Phe Asp Leu Phe Gly Gln Arg Lys Glu Val Ala Glu Cys Leu Lys
225                 230                 235                 240

Gly Ile Tyr Ala Ile Trp Gly Ala Met Leu Gln Glu Arg Lys Leu Ala
                245                 250                 255

Lys Lys Val Asp Gly Tyr Gln Ser Lys Asn Asp Phe Val Asp Val Cys
            260                 265                 270

Leu Asp Ser Gly Leu Asn Asp Tyr Gln Ile Asn Ala Leu Leu Met Glu
        275                 280                 285

Leu Phe Gly Ala Gly Thr Glu Thr Ser Ala Ser Thr Ile Glu Trp Ala
    290                 295                 300

Met Thr Glu Leu Thr Lys Asn Pro Lys Ile Thr Ala Lys Leu Arg Ser
305                 310                 315                 320

Glu Leu Gln Thr Val Val Gly Glu Arg Ser Val Lys Glu Ser Asp Phe
                325                 330                 335

Pro Asn Leu Pro Tyr Leu Glu Ala Thr Val Lys Glu Thr Leu Arg Leu
            340                 345                 350

His Pro Pro Thr Pro Leu Leu Leu Pro Arg Arg Ala Leu Glu Thr Cys
        355                 360                 365

Thr Ile Leu Asn Tyr Thr Ile Pro Lys Asp Cys Gln Ile Met Val Asn
    370                 375                 380

Ala Trp Gly Ile Gly Arg Asp Pro Lys Thr Trp Ile Asp Pro Leu Thr
385                 390                 395                 400

Phe Ser Pro Glu Arg Phe Leu Asn Ser Ser Val Asp Phe Arg Gly Asn
                405                 410                 415

Asp Phe Ser Leu Ile Pro Phe Gly Ala Gly Arg Arg Ile Cys Pro Gly
            420                 425                 430

Leu Pro Ile Ala Asn Gln Phe Ile Ala Leu Leu Val Ala Thr Phe Val
        435                 440                 445

Gln Asn Leu Asp Trp Cys Leu Pro Asn Gly Met Ser Val Asp His Leu
    450                 455                 460

Ile Val Glu Glu Lys Phe Gly Leu Thr Leu Gln Lys Glu Pro Pro Leu
465                 470                 475                 480

Phe Ile Val Pro Lys Ser Arg Val
                485

<210> SEQ ID NO 66
<211> LENGTH: 357
<212> TYPE: PRT
<213> ORGANISM: P. somniferum
```

<400> SEQUENCE: 66

```
Met Gly Ser Leu Asp Ala Lys Pro Ala Ala Thr Gln Glu Val Ser
1               5                   10                  15

Ile Lys Asp Gln Ala Gln Leu Trp Asn Ile Ile Tyr Gly Phe Ala Asp
            20                  25                  30

Ser Leu Val Leu Arg Cys Ala Val Glu Ile Gly Ile Ala Asp Ile Ile
        35                  40                  45

Lys Asn Asn Asp Gly Ala Ile Thr Leu Ala Gln Leu Ala Ala Lys Leu
    50                  55                  60

Pro Ile Thr Asn Val Ser Ser Asp Tyr Leu Tyr Arg Met Val Arg Tyr
65                  70                  75                  80

Leu Val His Leu Asn Ile Ile Glu Gln Glu Thr Cys Asn Gly Gly Val
                85                  90                  95

Glu Lys Val Tyr Ser Leu Lys Pro Val Gly Thr Leu Leu Leu Arg Asp
            100                 105                 110

Ala Glu Arg Ser Met Val Pro Met Ile Leu Gly Met Thr Gln Lys Asp
        115                 120                 125

Phe Met Val Ser Trp His Phe Met Lys Glu Gly Leu Gly Asn Gly Ser
    130                 135                 140

Thr Thr Ala Phe Glu Lys Gly Met Gly Met Asp Ile Trp Lys Tyr Leu
145                 150                 155                 160

Glu Gly Asn Pro Asp Gln Ser Gln Leu Phe Asn Glu Gly Met Ala Gly
                165                 170                 175

Glu Thr Arg Leu Leu Thr Lys Thr Leu Ile Glu Asp Cys Arg Asp Thr
            180                 185                 190

Phe Gln Gly Leu Asp Ser Leu Val Asp Ile Gly Gly Gly Asn Gly Thr
        195                 200                 205

Thr Ile Lys Ala Ile Tyr Glu Ala Phe Pro His Ile Lys Cys Thr Leu
    210                 215                 220

Tyr Asp Leu Pro His Val Val Ala Asn Ser His Asp Leu Pro Asn Ile
225                 230                 235                 240

Glu Lys Val Pro Gly Asp Met Phe Lys Ser Val Pro Ser Ala Gln Ala
                245                 250                 255

Ile Leu Leu Lys Leu Ile Leu His Asp Trp Thr Asp Glu Glu Cys Val
            260                 265                 270

Asn Ile Leu Lys Lys Cys Lys Glu Ala Ile Pro Lys Glu Thr Gly Lys
        275                 280                 285

Val Ile Ile Val Asp Val Ala Leu Glu Glu Ser Asn His Glu Leu
    290                 295                 300

Thr Lys Thr Arg Leu Ile Leu Asp Ile Asp Met Leu Val Asn Thr Gly
305                 310                 315                 320

Gly Arg Glu Arg Thr Ala Asp Asp Trp Glu Asn Leu Leu Lys Arg Ala
                325                 330                 335

Gly Phe Arg Ser His Lys Ile Arg Pro Ile Arg Ala Ile Gln Ser Val
            340                 345                 350

Ile Glu Ala Phe Pro
        355
```

<210> SEQ ID NO 67
<211> LENGTH: 2664
<212> TYPE: DNA
<213> ORGANISM: P. bracteatum

<400> SEQUENCE: 67

```
atggaattgc aatacttctc ctacttccaa cctacctctt ctgttgttgc tttgttgttg    60
gcattggtca gtatcttgtt ttccgttgtt gttttgagaa agaccttctc caacaactat   120
tcttctccag cttcttctac tgaaaccgct gttttgtgtc atcaaagaca caatcttgc    180
gccttgccaa tttctggttt gttgcatgtt ttcatgaaca agaacggttt gatccatgtt   240
accttgggta atatggctga taagtacggt ccaatttttct cttttccaac cggttctcat   300
agaaccttgg ttgtttcttc ttgggaaatg gtcaaagaat gtttcaccgg taacaacgat   360
accttcttta gtaacagacc aattccattg gccttcaaga ttattttcta tgccggtggt   420
gttgactctt atggtttggc tttggttcca tacggtaaat attggagaga attgagaaag   480
atctgcgtcc acaacttgtt gtccaatcaa caattattga agttcagaca cttgatcatc   540
tcccaagttg atacctcctt caacaagtta tacgaattgt gcaagaactc cgaagataat   600
caaggtatgg ttagaatgga tgattggttg gctcaattgt ccttctcagt tattggtaga   660
atcgtttgcg gtttccaatc tgatccaaaa actggtgctc catctagagt cgaacaattc   720
aaagaagcta ttaacgaagc ctcctacttc atgtctactt ctccagtttc tgataacgtt   780
ccaatgttgg gttggatcga tcaattgact ggtttgacta gaaacatgac ccattgtggt   840
aagaagttgg atttggttgt cgaatccatc atcaacgatc acagacaaaa gagaagattc   900
tccagaacaa aagtggtgga cgaaaaggat gatgaacaag atgatttcat cgacatctgc   960
ttgtccatta tggaacaacc acaattgcca ggtaacaaca atccaccaaa aatcccaatc  1020
aagtccatcg ttttggatat gattggtggt ggtactgata ccactaagtt gactactatt  1080
tggaccttgt ccttgttgtt gaacaaccca catgttttgg acaaggctaa caagaagtt   1140
gacgctcatt tcttgaccaa gagaagaagt acaaacgacg ctgctgttgt tgatttcgat  1200
gacattagaa acttggtcta catccaagcc attatcaaag aatccatgag attatacca   1260
gcctctccag ttgttgaaag attgtctggt gaagattgtg ttgttggtgg ttttcatgtt  1320
ccagctggta ctagattgtg ggttaatgtt tggaagatgc aaagagatcc taacgtttgg  1380
gctgatccaa tggttttag accagaaaga ttcttgtccc acggtcaaaa aaagatggtt   1440
gatgttagag gtaagaacta cgaattattg ccatttggtg ccggtagaag aatttgtcca  1500
ggtatttctt tctccttgga tttgatgcaa ttggtcttga ccagattgat cttggaattc  1560
gaaatgaagt ctccatccgg taaggttgat atgactgcta ctccaggttt gatgtcttac  1620
aaagttgttc cattggacat cttgttgacc catagaagaa tcaagtcttg cgttcaattg  1680
gcctcttctg aaagagatat ggaatcttct ggtgttccag ttatcacttt gagatctggt  1740
aaagttatgc cagttttggg tatgggtact tttgaaaaag ctggtaaggg ttccgaaaga  1800
gaaagattgg ctattttgaa ggccatcgaa gttggttaca gatactttga tactgctgct  1860
gcttacgaaa ccgaagaagt tttaggtgaa gctattgctg aagccttgca attgggttta  1920
atcaagtcaa gagatgaatt attcatttcc tccatgttgt ggtgtactga tgctcatcca  1980
gatagagttt tgttggcatt gcaaaactca ttgagaaact tgaagttgga atacgtcgac  2040
ttgtacatgt tgccatttcc agcttcattg aagccaggta agattaccat ggatatccca  2100
gaagaagata tctgcccaat ggattataga tctgttggt ctgctatgga agaatgccaa  2160
aatttgggtt tgaccaagtc cattggtgtc tctaatttct cctgcaaaaa gttggaagaa  2220
ttgatggcta ctgctaacat tccaccagct gtaaatcaag ttgaaatgtc tccagctttc  2280
caacaaaaga agttgagaga atactgcaac gctaacaaca ttttggtttc cgccgttttct  2340
attttgggtt ctaatggtac tccatggggt tcaaatgctg ttttaggttc tgaagtcttg  2400
```

-continued

```
aaaaagattg ctatggccaa gggtaaatcc gttgctcaag tttcaatgag atgggtttat    2460
gaacaaggtg cttccttggt tgttaagtcc tttagtgaag aaagattaag agaaaacttg    2520
aacatcttcg actggcaatt gaccaaagaa gataacgaaa agatcggtga atcccacaa     2580 tgcagaattt tgtctgctta cttcttggtt agtccaaagg gtccattcaa gtctcaagaa    2640
gaattatggg atgataaggc ttaa                                           2664

<210> SEQ ID NO 68
<211> LENGTH: 887
<212> TYPE: PRT
<213> ORGANISM: P. bracteatum

<400> SEQUENCE: 68
```

Met Glu Leu Gln Tyr Phe Ser Tyr Phe Gln Pro Thr Ser Val Val
1               5                   10                  15

Ala Leu Leu Ala Leu Val Ser Ile Leu Phe Ser Val Val Leu
            20                  25                  30

Arg Lys Thr Phe Ser Asn Asn Tyr Ser Ser Pro Ala Ser Ser Thr Glu
            35                  40                  45

Thr Ala Val Leu Cys His Gln Arg Gln Gln Ser Cys Ala Leu Pro Ile
50                  55                  60

Ser Gly Leu Leu His Val Phe Met Asn Lys Asn Gly Leu Ile His Val
65                  70                  75                  80

Thr Leu Gly Asn Met Ala Asp Lys Tyr Gly Pro Ile Phe Ser Phe Pro
                85                  90                  95

Thr Gly Ser His Arg Thr Leu Val Val Ser Ser Trp Glu Met Val Lys
            100                 105                 110

Glu Cys Phe Thr Gly Asn Asn Asp Thr Phe Phe Ser Asn Arg Pro Ile
        115                 120                 125

Pro Leu Ala Phe Lys Ile Ile Phe Tyr Ala Gly Gly Val Asp Ser Tyr
    130                 135                 140

Gly Leu Ala Leu Val Pro Tyr Gly Lys Tyr Trp Arg Glu Leu Arg Lys
145                 150                 155                 160

Ile Cys Val His Asn Leu Leu Ser Asn Gln Gln Leu Leu Lys Phe Arg
                165                 170                 175

His Leu Ile Ile Ser Gln Val Asp Thr Ser Phe Asn Lys Leu Tyr Glu
            180                 185                 190

Leu Cys Lys Asn Ser Glu Asp Asn Gln Gly Met Val Arg Met Asp Asp
        195                 200                 205

Trp Leu Ala Gln Leu Ser Phe Ser Val Ile Gly Arg Ile Val Cys Gly
    210                 215                 220

Phe Gln Ser Asp Pro Lys Thr Gly Ala Pro Ser Arg Val Glu Gln Phe
225                 230                 235                 240

Lys Glu Ala Ile Asn Glu Ala Ser Tyr Phe Met Ser Thr Ser Pro Val
                245                 250                 255

Ser Asp Asn Val Pro Met Leu Gly Trp Ile Asp Gln Leu Thr Gly Leu
            260                 265                 270

Thr Arg Asn Met Thr His Cys Gly Lys Lys Leu Asp Leu Val Val Glu
        275                 280                 285

Ser Ile Ile Asn Asp His Arg Gln Lys Arg Phe Ser Arg Thr Lys
    290                 295                 300

Gly Gly Asp Glu Lys Asp Asp Glu Gln Asp Phe Ile Asp Ile Cys
305                 310                 315                 320

```
Leu Ser Ile Met Glu Gln Pro Gln Leu Pro Gly Asn Asn Asn Pro Pro
                325                 330                 335

Lys Ile Pro Ile Lys Ser Ile Val Leu Asp Met Ile Gly Gly Gly Thr
            340                 345                 350

Asp Thr Thr Lys Leu Thr Thr Ile Trp Thr Leu Ser Leu Leu Leu Asn
        355                 360                 365

Asn Pro His Val Leu Asp Lys Ala Lys Gln Glu Val Asp Ala His Phe
    370                 375                 380

Leu Thr Lys Arg Arg Ser Thr Asn Asp Ala Val Val Asp Phe Asp
385                 390                 395                 400

Asp Ile Arg Asn Leu Val Tyr Ile Gln Ala Ile Ile Lys Glu Ser Met
                405                 410                 415

Arg Leu Tyr Pro Ala Ser Pro Val Val Glu Arg Leu Ser Gly Glu Asp
            420                 425                 430

Cys Val Val Gly Gly Phe His Val Pro Ala Gly Thr Arg Leu Trp Val
        435                 440                 445

Asn Val Trp Lys Met Gln Arg Asp Pro Asn Val Trp Ala Asp Pro Met
    450                 455                 460

Val Phe Arg Pro Glu Arg Phe Leu Ser His Gly Gln Lys Lys Met Val
465                 470                 475                 480

Asp Val Arg Gly Lys Asn Tyr Glu Leu Leu Pro Phe Gly Ala Gly Arg
                485                 490                 495

Arg Ile Cys Pro Gly Ile Ser Phe Ser Leu Asp Leu Met Gln Leu Val
            500                 505                 510

Leu Thr Arg Leu Ile Leu Glu Phe Glu Met Lys Ser Pro Ser Gly Lys
        515                 520                 525

Val Asp Met Thr Ala Thr Pro Gly Leu Met Ser Tyr Lys Val Val Pro
    530                 535                 540

Leu Asp Ile Leu Leu Thr His Arg Arg Ile Lys Ser Cys Val Gln Leu
545                 550                 555                 560

Ala Ser Ser Glu Arg Asp Met Glu Ser Ser Gly Val Pro Val Ile Thr
                565                 570                 575

Leu Arg Ser Gly Lys Val Met Pro Val Leu Gly Met Gly Thr Phe Glu
            580                 585                 590

Lys Ala Gly Lys Gly Ser Glu Arg Glu Arg Leu Ala Ile Leu Lys Ala
        595                 600                 605

Ile Glu Val Gly Tyr Arg Tyr Phe Asp Thr Ala Ala Ala Tyr Glu Thr
    610                 615                 620

Glu Glu Val Leu Gly Glu Ala Ile Ala Glu Ala Leu Gln Leu Gly Leu
625                 630                 635                 640

Ile Lys Ser Arg Asp Glu Leu Phe Ile Ser Ser Met Leu Trp Cys Thr
                645                 650                 655

Asp Ala His Pro Asp Arg Val Leu Leu Ala Leu Gln Asn Ser Leu Arg
            660                 665                 670

Asn Leu Lys Leu Glu Tyr Val Asp Leu Tyr Met Leu Pro Phe Pro Ala
        675                 680                 685

Ser Leu Lys Pro Gly Lys Ile Thr Met Asp Ile Pro Glu Glu Asp Ile
    690                 695                 700

Cys Pro Met Asp Tyr Arg Ser Val Trp Ser Ala Met Glu Glu Cys Gln
705                 710                 715                 720

Asn Leu Gly Leu Thr Lys Ser Ile Gly Val Ser Asn Phe Ser Cys Lys
                725                 730                 735

Lys Leu Glu Glu Leu Met Ala Thr Ala Asn Ile Pro Pro Ala Val Asn
```

```
                    740                745                750
Gln Val Glu Met Ser Pro Ala Phe Gln Gln Lys Lys Leu Arg Glu Tyr
                755                760                765

Cys Asn Ala Asn Asn Ile Leu Val Ser Ala Val Ser Ile Leu Gly Ser
                770                775                780

Asn Gly Thr Pro Trp Gly Ser Asn Ala Val Leu Gly Ser Glu Val Leu
785                790                795                800

Lys Lys Ile Ala Met Ala Lys Gly Lys Ser Val Ala Gln Val Ser Met
                805                810                815

Arg Trp Val Tyr Glu Gln Gly Ala Ser Leu Val Val Lys Ser Phe Ser
                820                825                830

Glu Glu Arg Leu Arg Glu Asn Leu Asn Ile Phe Asp Trp Gln Leu Thr
                835                840                845

Lys Glu Asp Asn Glu Lys Ile Gly Glu Ile Pro Gln Cys Arg Ile Leu
                850                855                860

Ser Ala Tyr Phe Leu Val Ser Pro Lys Gly Pro Phe Lys Ser Gln Glu
865                870                875                880

Glu Leu Trp Asp Asp Lys Ala
                885

<210> SEQ ID NO 69
<211> LENGTH: 1512
<212> TYPE: DNA
<213> ORGANISM: P. bracteatum

<400> SEQUENCE: 69
atggccccaa tcaacatcga agaaaatgat ttctggatga ttgcctgcac cgttattatc         60 gttttttgcct tgatgaagtt catggtttcc ttctaccaat ctgctaacac tactgaatgg       120
ccagaaggtc caaaaacctt gccaattatt ggtaacttgc atcaattggg tggtggtgtt       180
ccattgcaag ttgctttagc taatttggct aaagtttacg gtggtgcttt caccatttgg       240
attggttctt gggttccaat gatcgttatc tccgatattg ataacgccag agaagttttg       300
gttaacaagt ctgctgatta ctccgctaga gatgttccag atattttgaa gattattacc       360
gccaacggta gaacattgc tgattgtgat tctggtccat tctggcatca tttgaagaag       420
ggtttacaat cctgcatcaa cccatctaac gttatgtctt gtccagattg caagaaaag       480 gacatgcaaa acttgattaa gtccatgcaa gaaagagcct ctcaacaaaa cggtatcttg       540
aaaccattgg atcatgctaa gaagcctcc atcagattat tgtccagagt tatttttcggt       600 caagacttct ccaacgaaga tttggttatt ggtgttaagg atgccttgga cgaaatggtt       660
agaatttctg gtttggcttc tttggctgat gctttcaaaa ttgctaagta cttgccatcc       720
caaaaaaaga acatcagaga tatgtacgcc accagagata gagtttacaa cttgattcaa       780
ccacacatcg tcagtaattt gccagccaat tcattcttgc atttcttgac ctctcaagac       840
tactctgacg aaatcatcta ctccatggtt ttggaaattt tcggttttggg tgttgattct       900 actgctgcta cagctgtttg gcttttgtct ttttttggttg gtgaacaaga aatccaagaa       960
aagttgtaca gagaaatcaa caacttgacc ggtggtcaaa gaccagttaa ggttgttgac      1020
ttgaaagaat tgccatactt gcaagccgtt atgaaagaaa ccttgagaat gaagccaatt      1080
gctccattgg ctgttccaca tgttgctgct aaagatacca cttttaaggg tagaagaatc      1140
gtcaagggta ctaaggttat ggttaacttg tacgccattc atcacgatcc aaatgttttt      1200
ccagctccat acaagttcat gcctgaaaga tttttgaagg tgttaactc cgatggtaga      1260
```

-continued

```
tacggtgata ttaacaccat ggaatcctca ttgattccat ttggtgctgg tatgagaatt    1320
tgcggtggtg ttgaattggc aaaacaaatg gttggttttg ctttggcctc tatggtcaat    1380
gaatttaagt gggattgtgt ctccgaaggt aacttaccag atttgtctga agctatctcc    1440
ttcatcttgt acatgaagaa tccattggaa gctaaggtta ccccaagaac taagccattc    1500
gattctagat ga                                                       1512
```

<210> SEQ ID NO 70
<211> LENGTH: 503
<212> TYPE: PRT
<213> ORGANISM: P. bracteatum

<400> SEQUENCE: 70

| | | | | | | | | | | | | | | |
|---|---|---|---|---|---|---|---|---|---|---|---|---|---|---|
| Met | Ala | Pro | Ile | Asn | Ile | Glu | Glu | Asn | Asp | Phe | Trp | Met | Ile | Ala | Cys |
| 1 | | | | 5 | | | | | 10 | | | | | 15 | |
| Thr | Val | Ile | Ile | Val | Phe | Ala | Leu | Met | Lys | Phe | Met | Val | Ser | Phe | Tyr |
| | | | 20 | | | | | 25 | | | | | 30 | | |
| Gln | Ser | Ala | Asn | Thr | Thr | Glu | Trp | Pro | Glu | Gly | Pro | Lys | Thr | Leu | Pro |
| | | | 35 | | | | | 40 | | | | | 45 | | |
| Ile | Ile | Gly | Asn | Leu | His | Gln | Leu | Gly | Gly | Gly | Val | Pro | Leu | Gln | Val |
| | 50 | | | | | 55 | | | | | 60 | | | | |
| Ala | Leu | Ala | Asn | Leu | Ala | Lys | Val | Tyr | Gly | Gly | Ala | Phe | Thr | Ile | Trp |
| 65 | | | | | 70 | | | | | 75 | | | | | 80 |
| Ile | Gly | Ser | Trp | Val | Pro | Met | Ile | Val | Ile | Ser | Asp | Ile | Asp | Asn | Ala |
| | | | | 85 | | | | | 90 | | | | | 95 | |
| Arg | Glu | Val | Leu | Val | Asn | Lys | Ser | Ala | Asp | Tyr | Ser | Ala | Arg | Asp | Val |
| | | | | 100 | | | | | 105 | | | | | 110 | |
| Pro | Asp | Ile | Leu | Lys | Ile | Ile | Thr | Ala | Asn | Gly | Lys | Asn | Ile | Ala | Asp |
| | | | 115 | | | | | 120 | | | | | 125 | | |
| Cys | Asp | Ser | Gly | Pro | Phe | Trp | His | His | Leu | Lys | Lys | Gly | Leu | Gln | Ser |
| 130 | | | | | 135 | | | | | 140 | | | | | |
| Cys | Ile | Asn | Pro | Ser | Asn | Val | Met | Ser | Leu | Ser | Arg | Leu | Gln | Glu | Lys |
| 145 | | | | | 150 | | | | | 155 | | | | | 160 |
| Asp | Met | Gln | Asn | Leu | Ile | Lys | Ser | Met | Gln | Glu | Arg | Ala | Ser | Gln | Gln |
| | | | | 165 | | | | | 170 | | | | | 175 | |
| Asn | Gly | Ile | Leu | Lys | Pro | Leu | Asp | His | Ala | Lys | Glu | Ala | Ser | Ile | Arg |
| | | | 180 | | | | | 185 | | | | | 190 | | |
| Leu | Leu | Ser | Arg | Val | Ile | Phe | Gly | Gln | Asp | Phe | Ser | Asn | Glu | Asp | Leu |
| | | | 195 | | | | | 200 | | | | | 205 | | |
| Val | Ile | Gly | Val | Lys | Asp | Ala | Leu | Asp | Glu | Met | Val | Arg | Ile | Ser | Gly |
| | | 210 | | | | | 215 | | | | | 220 | | | |
| Leu | Ala | Ser | Leu | Ala | Asp | Ala | Phe | Lys | Ile | Ala | Lys | Tyr | Leu | Pro | Ser |
| 225 | | | | | 230 | | | | | 235 | | | | | 240 |
| Gln | Lys | Lys | Asn | Ile | Arg | Asp | Met | Tyr | Ala | Thr | Arg | Asp | Arg | Val | Tyr |
| | | | | 245 | | | | | 250 | | | | | 255 | |
| Asn | Leu | Ile | Gln | Pro | His | Ile | Val | Ser | Asn | Leu | Pro | Ala | Asn | Ser | Phe |
| | | | 260 | | | | | 265 | | | | | 270 | | |
| Leu | His | Phe | Leu | Thr | Ser | Gln | Asp | Tyr | Ser | Asp | Glu | Ile | Ile | Tyr | Ser |
| | | | 275 | | | | | 280 | | | | | 285 | | |
| Met | Val | Leu | Glu | Ile | Phe | Gly | Leu | Gly | Val | Asp | Ser | Thr | Ala | Ala | Thr |
| | | 290 | | | | | 295 | | | | | 300 | | | |
| Ala | Val | Trp | Ala | Leu | Ser | Phe | Leu | Val | Gly | Glu | Gln | Glu | Ile | Gln | Glu |
| 305 | | | | | 310 | | | | | 315 | | | | | 320 |
| Lys | Leu | Tyr | Arg | Glu | Ile | Asn | Asn | Leu | Thr | Gly | Gly | Gln | Arg | Pro | Val |

-continued

```
                325                 330                 335
Lys Val Val Asp Leu Lys Glu Leu Pro Tyr Leu Gln Ala Val Met Lys
            340                 345                 350
Glu Thr Leu Arg Met Lys Pro Ile Ala Pro Leu Ala Val Pro His Val
            355                 360                 365
Ala Ala Lys Asp Thr Thr Phe Lys Gly Arg Arg Ile Val Lys Gly Thr
            370                 375                 380
Lys Val Met Val Asn Leu Tyr Ala Ile His His Asp Pro Asn Val Phe
385                 390                 395                 400
Pro Ala Pro Tyr Lys Phe Met Pro Glu Arg Phe Leu Lys Gly Val Asn
                405                 410                 415
Ser Asp Gly Arg Tyr Gly Asp Ile Asn Thr Met Glu Ser Ser Leu Ile
            420                 425                 430
Pro Phe Gly Ala Gly Met Arg Ile Cys Gly Gly Val Glu Leu Ala Lys
            435                 440                 445
Gln Met Val Gly Phe Ala Leu Ala Ser Met Val Asn Glu Phe Lys Trp
            450                 455                 460
Asp Cys Val Ser Glu Gly Asn Leu Pro Asp Leu Ser Glu Ala Ile Ser
465                 470                 475                 480
Phe Ile Leu Tyr Met Lys Asn Pro Leu Glu Ala Lys Val Thr Pro Arg
                485                 490                 495
Thr Lys Pro Phe Asp Ser Arg
            500

<210> SEQ ID NO 71
<211> LENGTH: 311
<212> TYPE: PRT
<213> ORGANISM: P. bracteatum

<400> SEQUENCE: 71

Met Pro Glu Thr Cys Pro Asn Thr Val Thr Lys Met Arg Cys Ala Val
1               5                   10                  15
Val Thr Gly Gly Asn Lys Gly Ile Gly Phe Glu Ile Cys Lys Gln Leu
            20                  25                  30
Ser Ser Ser Gly Ile Met Val Val Leu Thr Cys Arg Asp Val Thr Arg
        35                  40                  45
Gly Leu Glu Ala Val Glu Lys Leu Lys Asn Ser Asn His Glu Asn Val
    50                  55                  60
Val Phe His Gln Leu Asp Val Thr Asp Pro Ile Thr Thr Met Ser Ser
65                  70                  75                  80
Leu Ala Asp Phe Ile Lys Ala Arg Phe Gly Lys Leu Asp Ile Leu Val
                85                  90                  95
Asn Asn Ala Gly Val Ala Gly Phe Ser Val Asp Ala Asp Arg Phe Lys
            100                 105                 110
Ala Met Ile Ser Asp Ile Gly Glu Asp Ser Glu Glu Val Val Lys Ile
            115                 120                 125
Tyr Glu Lys Pro Glu Ala Gln Glu Leu Met Ser Glu Thr Tyr Glu Leu
            130                 135                 140
Ala Glu Glu Cys Leu Lys Ile Asn Tyr Tyr Gly Val Lys Ser Val Thr
145                 150                 155                 160
Glu Val Leu Leu Pro Leu Leu Gln Leu Ser Asp Ser Pro Arg Ile Val
                165                 170                 175
Asn Val Ser Ser Ser Thr Gly Ser Leu Lys Tyr Val Ser Asn Glu Thr
            180                 185                 190
```

```
Ala Leu Glu Ile Leu Gly Asp Gly Asp Ala Leu Thr Glu Arg Ile
            195                 200                 205

Asp Met Val Val Asn Met Leu Leu Lys Asp Phe Lys Glu Asn Leu Ile
    210                 215                 220

Glu Thr Asn Gly Trp Pro Ser Phe Gly Ala Ala Tyr Thr Thr Ser Lys
225                 230                 235                 240

Ala Cys Leu Asn Ala Tyr Thr Arg Val Leu Ala Lys Lys Ile Pro Lys
                245                 250                 255

Phe Gln Val Asn Cys Val Cys Pro Gly Leu Val Lys Thr Glu Met Asn
                260                 265                 270

Tyr Gly Ile Gly Asn Tyr Thr Ala Asp Glu Gly Ala Lys His Val Val
            275                 280                 285

Arg Ile Ala Leu Phe Pro Asp Asp Gly Pro Ser Gly Phe Phe Tyr Asp
    290                 295                 300

Cys Ser Glu Leu Ser Ala Phe
305                 310

<210> SEQ ID NO 72

<400> SEQUENCE: 72

000

<210> SEQ ID NO 73
<211> LENGTH: 474
<212> TYPE: PRT
<213> ORGANISM: P. somniferum

<400> SEQUENCE: 73

Met Ala Thr Met Tyr Ser Ala Ala Val Glu Val Ile Ser Lys Glu Thr
1               5                   10                  15

Ile Lys Pro Thr Thr Pro Thr Pro Ser Gln Leu Lys Asn Phe Asn Leu
                20                  25                  30

Ser Leu Leu Asp Gln Cys Phe Pro Leu Tyr Tyr Val Pro Ile Ile
                35                  40                  45

Leu Phe Tyr Pro Ala Thr Ala Ala Asn Ser Thr Gly Ser Ser Asn His
    50                  55                  60

His Asp Asp Leu Asp Leu Leu Lys Ser Ser Leu Ser Lys Thr Leu Val
65                  70                  75                  80

His Phe Tyr Pro Met Ala Gly Arg Met Ile Asp Asn Ile Leu Val Asp
                85                  90                  95

Cys His Asp Gln Gly Ile Asn Phe Tyr Lys Val Lys Ile Arg Gly Lys
                100                 105                 110

Met Cys Glu Phe Met Ser Gln Pro Asp Val Pro Leu Ser Gln Leu Leu
            115                 120                 125

Pro Ser Glu Val Val Ser Ala Ser Val Pro Lys Glu Ala Leu Val Ile
    130                 135                 140

Val Gln Val Asn Met Phe Asp Cys Gly Gly Thr Ala Ile Cys Ser Ser
145                 150                 155                 160

Val Ser His Lys Ile Ala Asp Ala Ala Thr Met Ser Thr Phe Ile Arg
                165                 170                 175

Ser Trp Ala Ser Thr Thr Lys Thr Ser Arg Ser Gly Gly Ser Thr Ala
            180                 185                 190

Ala Val Thr Asp Gln Lys Leu Ile Pro Ser Phe Asp Ser Ala Ser Leu
    195                 200                 205

Phe Pro Pro Ser Glu Arg Leu Thr Ser Pro Ser Gly Met Ser Glu Ile
```

```
                210                 215                 220

Pro Phe Ser Ser Thr Pro Glu Asp Thr Glu Asp Lys Thr Val Ser
225                 230                 235                 240

Lys Arg Phe Val Phe Asp Phe Ala Lys Ile Thr Ser Val Arg Glu Lys
                245                 250                 255

Leu Gln Val Leu Met His Asp Asn Tyr Lys Ser Arg Arg Gln Thr Arg
                260                 265                 270

Val Glu Val Val Thr Ser Leu Ile Trp Lys Ser Val Met Lys Ser Thr
                275                 280                 285

Pro Ala Gly Phe Leu Pro Val Val His His Ala Val Asn Leu Arg Lys
                290                 295                 300

Lys Met Asp Pro Pro Leu Gln Asp Val Ser Phe Gly Asn Leu Ser Val
305                 310                 315                 320

Thr Val Ser Ala Phe Leu Pro Ala Thr Thr Thr Thr Thr Thr Asn Ala
                325                 330                 335

Val Asn Lys Thr Ile Asn Ser Thr Ser Ser Glu Ser Gln Val Val Leu
                340                 345                 350

His Glu Leu His Asp Phe Ile Ala Gln Met Arg Ser Glu Ile Asp Lys
                355                 360                 365

Val Lys Gly Asp Lys Gly Ser Leu Glu Lys Val Ile Gln Asn Phe Ala
                370                 375                 380

Ser Gly His Asp Ala Ser Ile Lys Lys Ile Asn Asp Val Glu Val Ile
385                 390                 395                 400

Asn Phe Trp Ile Ser Ser Trp Cys Arg Met Gly Leu Tyr Glu Ile Asp
                405                 410                 415

Phe Gly Trp Gly Lys Pro Ile Trp Val Thr Val Asp Pro Asn Ile Lys
                420                 425                 430

Pro Asn Lys Asn Cys Phe Met Asn Asp Thr Lys Cys Gly Glu Gly
                435                 440                 445

Ile Glu Val Trp Ala Ser Phe Leu Glu Asp Asp Met Ala Lys Phe Glu
                450                 455                 460

Leu His Leu Ser Glu Ile Leu Glu Leu Ile
465                 470

<210> SEQ ID NO 74
<211> LENGTH: 537
<212> TYPE: DNA
<213> ORGANISM: Coptis japonica

<400> SEQUENCE: 74
atggaaagat tgatcttcaa tggtagacct tgttgcaca gagttaccaa agaagaaacc        60
gttatgttgt accacgaatt ggaagttgct gcttctgctg atgaagtttg gtctgttgaa      120
ggttctccag aattgggttt acatttgcca gatttgttgc cagctggtat ttttgccaag      180
ttcgaaatta ctggtgatgg tggtgaaggt tccatttggg atatgacttt tccaccaggt      240
caattcccac atcattacag agaaaagttc gtcttttcg accacaagaa cagatacaag      300
ttggtcgaac aaatcgatgg tgatttcttc gatttgggtg ttacttacta catggacacc      360
attagagttg ttgctactgg tccagattct tgcgttatta gtctactac tgaataccac      420 gtcaagccag aatttgctaa atcgttaag ccattgatcg ataccgttcc attggctatt      480
atgtctgaag ctattgccaa ggttgtcttg gaaacaaac acaagtcatc tgaatga        537

<210> SEQ ID NO 75
<211> LENGTH: 178
```

<212> TYPE: PRT
<213> ORGANISM: Coptis Japonica

<400> SEQUENCE: 75

```
Met Glu Arg Leu Ile Phe Asn Gly Arg Pro Leu Leu His Arg Val Thr
1               5                   10                  15
Lys Glu Glu Thr Val Met Leu Tyr His Glu Leu Glu Val Ala Ala Ser
            20                  25                  30
Ala Asp Glu Val Trp Ser Val Glu Gly Ser Pro Glu Leu Gly Leu His
        35                  40                  45
Leu Pro Asp Leu Leu Pro Ala Gly Ile Phe Ala Lys Phe Glu Ile Thr
    50                  55                  60
Gly Asp Gly Gly Glu Gly Ser Ile Leu Asp Met Thr Phe Pro Pro Gly
65                  70                  75                  80
Gln Phe Pro His His Tyr Arg Glu Lys Phe Val Phe Asp His Lys
                85                  90                  95
Asn Arg Tyr Lys Leu Val Glu Gln Ile Asp Gly Asp Phe Phe Asp Leu
            100                 105                 110
Gly Val Thr Tyr Tyr Met Asp Thr Ile Arg Val Val Ala Thr Gly Pro
        115                 120                 125
Asp Ser Cys Val Ile Lys Ser Thr Thr Glu Tyr His Val Lys Pro Glu
    130                 135                 140
Phe Ala Lys Ile Val Lys Pro Leu Ile Asp Thr Val Pro Leu Ala Ile
145                 150                 155                 160
Met Ser Glu Ala Ile Ala Lys Val Val Leu Glu Asn Lys His Lys Ser
                165                 170                 175
Ser Glu
```

<210> SEQ ID NO 76
<211> LENGTH: 705
<212> TYPE: PRT
<213> ORGANISM: Beta vulgaris

<400> SEQUENCE: 76

```
Met Asp Ser Asn Ser Ile Lys Val Ser Pro Leu Asp Leu Met Ser Ala
1               5                   10                  15
Leu Leu Lys Gly Asn Phe Glu Gln Leu Asn Ala Ser Phe Glu Asp Ser
            20                  25                  30
Ser Ala Ala Ala Leu Ile Val Glu Asn Arg Glu Val Leu Met Phe Val
        35                  40                  45
Thr Thr Ser Ile Ala Val Leu Ile Gly Cys Ala Phe Leu Phe Ile Trp
    50                  55                  60
Lys Lys Ser Asn Gly Gly Lys Ser Ser Lys Val Val Ser Glu Leu Pro
65                  70                  75                  80
Lys Pro Leu Ile Leu Lys Asp Asp Val Glu Val Asp Gly Lys
                85                  90                  95
Lys Lys Val Thr Val Phe Phe Gly Thr Gln Thr Gly Thr Ala Glu Gly
            100                 105                 110
Phe Ala Lys Ala Leu Val Glu Glu Ala Lys Ala Arg Tyr Glu Lys Ala
        115                 120                 125
Thr Phe Lys Ile Val Asp Leu Asp Asp Tyr Ala Gly Asp Asp Asp Glu
    130                 135                 140
Tyr Glu Arg Lys Leu Lys Lys Glu Asn Leu Ala Phe Phe Leu Ala
145                 150                 155                 160
Thr Tyr Gly Asp Gly Glu Pro Thr Asp Asn Ala Ala Arg Phe Tyr Lys
```

```
            165                 170                 175
Trp Phe Leu Glu Gly Lys Asp Arg Gly Glu Trp Leu Gln Asn Leu Glu
        180                 185                 190
Tyr Gly Val Phe Gly Leu Gly Asn Arg Gln Tyr Glu His Phe Asn Lys
        195                 200                 205
Val Gly Lys Glu Ile Asp Glu Leu Leu Ala Glu Gln Gly Ala Lys Arg
        210                 215                 220
Leu Val Pro Val Gly Leu Gly Asp Asp Gln Cys Ile Glu Asp Asp
225                 230                 235                 240
Phe Thr Ala Trp Lys Asp Leu Val Trp Pro Glu Leu Asp Arg Leu Leu
                    245                 250                 255
Arg Asp Glu Asp Asp Val Ala Val Ser Thr Pro Tyr Thr Ala Thr Ile
        260                 265                 270
Pro Glu Tyr Arg Val Val Phe His Glu Ala Ala Glu Val Ala Gln Gln
        275                 280                 285
Asp Lys Ser Trp Ala Asn Ala Asn Gly His Ala Val Phe Asp Ala Gln
        290                 295                 300
His Pro Cys Arg Ser Asn Val Ala Val Arg Arg Glu Leu His Thr Pro
305                 310                 315                 320
Ala Ser Asp Arg Ser Cys Thr His Leu Glu Phe Asp Val Ser Gly Thr
                    325                 330                 335
Gly Leu Lys Tyr Glu Thr Gly Asp His Val Gly Val Tyr Cys Glu Asn
        340                 345                 350
Leu Val Glu Thr Val Glu Glu Ala Glu Arg Leu Leu Gly Leu Lys Asp
        355                 360                 365
Thr Tyr Phe Ser Ile His Thr Asp Asn Glu Asp Gly Thr Pro Val Ala
        370                 375                 380
Gly Thr Ser Leu Pro Pro Pro Phe Pro Pro Cys Thr Leu Arg Ser Ala
385                 390                 395                 400
Leu Thr Arg Tyr Ala Asp Leu Leu Ser Ser Pro Lys Lys Ser Ala Leu
                    405                 410                 415
Leu Ala Leu Ala Ala His Ala Ser Asp Pro Asn Glu Ala Lys Arg Leu
                    420                 425                 430
Lys Tyr Leu Ala Ser Pro Ala Gly Lys Asp Glu Tyr Ser Gln Trp Val
        435                 440                 445
Val Ala Ser Gln Arg Ser Leu Leu Glu Val Met Ala Glu Phe Pro Ser
        450                 455                 460
Ala Lys Pro Pro Leu Gly Val Phe Phe Ala Ala Val Ala Pro Arg Leu
465                 470                 475                 480
Gln Pro Arg Tyr Tyr Ser Ile Ser Ser Pro Arg Val Ala Pro Ser
                    485                 490                 495
Arg Ile His Val Thr Cys Ala Leu Val Leu Asp Lys Met Pro Thr Gly
                    500                 505                 510
Arg Ile His Lys Gly Val Cys Ser Thr Trp Met Lys Asn Ser Val Ala
                    515                 520                 525
Gln Gly Glu Ser His Asp Cys Ser Trp Ala Pro Ile Phe Val Arg Gln
        530                 535                 540
Ser Asn Phe Lys Leu Pro Ala Asp Ser Ser Val Pro Ile Ile Met Ile
545                 550                 555                 560
Gly Pro Gly Thr Gly Leu Ala Pro Phe Arg Gly Phe Leu Gln Glu Arg
                    565                 570                 575
Ser Ala Leu Lys Glu Asp Gly Val Asp Leu Gly Gln Ala Ile Leu Phe
        580                 585                 590
```

```
Phe Gly Cys Arg Asn Arg Lys Val Asp Phe Ile Tyr Glu Asp Glu Leu
            595                 600                 605

Gln Asn Phe Val Glu Thr Gly Val Leu Ser Glu Leu Val Val Ala Phe
        610                 615                 620

Ser Arg Glu Gly Pro Thr Lys Glu Tyr Val Gln His Lys Met Met Glu
625                 630                 635                 640

Arg Ala Ser Asp Val Trp Asn Val Ile Asn Gln Gly Gly Tyr Val Tyr
                645                 650                 655

Val Cys Gly Asp Ala Lys Gly Met Ala Arg Asp Val His Arg Val Leu
            660                 665                 670

His Thr Ile Leu Gln Glu Gln Gly Gly Met Gly Ser Ser Gln Ala Glu
        675                 680                 685

Gly Met Val Lys Asn Leu Gln Thr Thr Gly Arg Tyr Leu Arg Asp Val
    690                 695                 700

Trp
705

<210> SEQ ID NO 77
<211> LENGTH: 256
<212> TYPE: PRT
<213> ORGANISM: S. cerevisiae

<400> SEQUENCE: 77

Met Asp Phe Thr Lys Pro Glu Thr Val Leu Asn Leu Gln Asn Ile Arg
1               5                   10                  15

Asp Glu Leu Val Arg Met Glu Asp Ser Ile Ile Phe Lys Phe Ile Glu
            20                  25                  30

Arg Ser His Phe Ala Thr Cys Pro Ser Val Tyr Glu Ala Asn His Pro
        35                  40                  45

Gly Leu Glu Ile Pro Asn Phe Lys Gly Ser Phe Leu Asp Trp Ala Leu
    50                  55                  60

Ser Asn Leu Glu Ile Ala His Ser Arg Ile Arg Arg Phe Glu Ser Pro
65                  70                  75                  80

Asp Glu Thr Pro Phe Phe Pro Asp Lys Ile Gln Lys Ser Phe Leu Pro
                85                  90                  95

Ser Ile Asn Tyr Pro Gln Ile Leu Ala Pro Tyr Ala Pro Glu Val Asn
            100                 105                 110

Tyr Asn Asp Lys Ile Lys Lys Val Tyr Ile Glu Lys Ile Ile Pro Leu
        115                 120                 125

Ile Ser Lys Arg Asp Gly Asp Asp Lys Asn Asn Phe Ser Ser Val Ala
    130                 135                 140

Thr Arg Asp Ile Glu Cys Leu Gln Ser Leu Ser Arg Arg Ile His Phe
145                 150                 155                 160

Gly Lys Phe Val Ala Glu Ala Lys Phe Gln Ser Asp Ile Pro Leu Tyr
                165                 170                 175

Thr Lys Leu Ile Lys Ser Lys Asp Val Glu Gly Ile Met Lys Asn Ile
            180                 185                 190

Thr Asn Ser Ala Val Glu Glu Lys Ile Leu Glu Arg Leu Thr Lys Lys
        195                 200                 205

Ala Glu Val Tyr Gly Val Asp Pro Thr Asn Glu Ser Gly Glu Arg Arg
    210                 215                 220

Ile Thr Pro Glu Tyr Leu Val Lys Ile Tyr Lys Glu Ile Val Ile Pro
225                 230                 235                 240

Ile Thr Lys Glu Val Glu Val Glu Tyr Leu Leu Arg Arg Leu Glu Glu
```

<210> SEQ ID NO 78
<211> LENGTH: 2118
<212> TYPE: DNA
<213> ORGANISM: beta vulgaris

<400> SEQUENCE: 78

| | | | | | |
|---|---|---|---|---|---|
| atggactcca | actccatcaa | ggtttctcca | ttggatttga | tgtctgcttt | gttgaagggt | 60 |
| aacttcgaac | aattgaacgc | ctctttcgaa | gattcttctg | ctgctgcttt | gatcgttgaa | 120 |
| aacagagaag | ttttgatgtt | cgtcaccacc | tctattgctg | ttttgattgg | ttgtgccttc | 180 |
| ttgttcatct | ggaaaaagtc | taacggtggc | aagtcctcta | agttgtttc | tgaattgcca | 240 |
| aagccactga | tcttgaagga | tgatgatgtt | gaagttgatg | acggtaagaa | gaaggttact | 300 |
| gttttcttcg | gtactcaaac | tggtactgct | gaaggttttg | ctaaagcttt | ggttgaagag | 360 |
| gctaaagcca | gatacgaaaa | ggctactttt | aagatcgttg | acttggatga | ttacgccggt | 420 |
| gatgatgacg | aatacgaaag | aaagttgaag | aaagagaacc | tggctttctt | cttcttggct | 480 |
| acttatggtg | atggtgaacc | tactgataat | gctgctagat | tttacaagtg | gttcttggaa | 540 |
| ggtaaggata | gaggtgaatg | gttgcaaaat | ttggagtacg | tgttttttgg | tttgggtaac | 600 |
| agacaatacg | aacacttcaa | caaggtcggt | aaagaaatcg | atgaactgtt | ggctgaacaa | 660 |
| ggtgctaaaa | gattggttcc | agttggttta | ggtgatgacg | atcaatgtat | cgaagatgat | 720 |
| tttaccgctt | ggaaagattt | ggtatggcca | gaattggaca | gactgttgag | agatgaagat | 780 |
| gatgtagctg | tttctactcc | atacactgct | actattccag | agtacagagt | tgtttttcat | 840 |
| gaagctgctg | aagttgccca | acaagataag | tcttgggcta | atgctaatgg | tcatgctgtt | 900 |
| tttgatgctc | aacatccatg | tagatctaac | gttgctgtta | aagagaatt | gcatactcca | 960 |
| gcttcagata | gatcttgtac | ccatttggaa | ttcgatgttt | ctggtactgg | tttgaagtac | 1020 |
| gaaactggtg | atcatgttgg | tgtttactgc | gaaaacttgg | ttgaaactgt | tgaagaagct | 1080 |
| gaaaggttgt | tgggtttgaa | ggataccac | ttctctatcc | ataccgataa | cgaagatggt | 1140 |
| actccagttg | ctggtacttc | tttgccacca | ccatttccac | catgtacttt | gagatctgct | 1200 |
| tgactagat | acgccgattt | gttgtcctct | ccaaaaaaat | ctgctttatt | ggccttggct | 1260 |
| gctcatgctt | ctgatccaaa | tgaagctaag | agattgaagt | acttggcttc | tccagctggt | 1320 |
| aaagatgaat | attctcaatg | ggttgttgcc | tctcagagat | ctttgttgga | agttatggct | 1380 |
| gaatttccat | ctgctaaacc | accattgggt | gtttttttg | ctgctgttgc | tccaagattg | 1440 |
| cagccaagat | attactccat | ttcatcttct | ccaagagttg | ccccatctag | aattcatgtt | 1500 |
| acttgtgctt | tggtgttgga | taagatgcca | actggtagaa | ttcacaaggg | tgtttgttca | 1560 |
| acctggatga | agaattctgt | tgctcaaggt | gaatctcatg | attgctcttg | ggctccaatt | 1620 |
| ttcgttagac | aatctaactt | taagttgccc | gctgattctt | ccgttccaat | tatcatgatt | 1680 |
| ggtccaggta | caggtttggc | tcctttaga | ggttttctac | aagaaaggtc | cgccttgaaa | 1740 |
| gaagatggcg | ttgatttggg | tcaagccatt | ttgttttttg | gctgcagaaa | cagaaaggtc | 1800 |
| gacttcatat | acgaagatga | gttgcaaaac | ttcgtcgaaa | caggtgtttt | gtccgaattg | 1860 |
| gttgttgctt | tttctagaga | aggtcccacc | aaagaatacg | ttcaacataa | gatgatggaa | 1920 |
| agagcttctg | acgtttggaa | cgttatcaat | caaggtggtt | acgtttacgt | ttgcggtgat | 1980 |
| gctaaaggta | tggcaagaga | tgttcataga | gtcttgcata | ccatcctaca | agagcaaggt | 2040 |
| ggtatgggtt | cttctcaagc | tgaaggtatg | gttaagaact | tgcaaactac | tggtagatac | 2100 | ttgagggatg tttggtaa                                              2118

<210> SEQ ID NO 79
<211> LENGTH: 180
<212> TYPE: PRT
<213> ORGANISM: P. somniferum

<400> SEQUENCE: 79

Met Asp Ser Ile Asn Ser Ser Ile Tyr Phe Cys Ala Tyr Phe Arg Glu
1               5                   10                  15

Leu Ile Ile Lys Leu Leu Met Ala Pro Leu Gly Val Ser Gly Leu Val
            20                  25                  30

Gly Lys Leu Ser Thr Glu Leu Glu Val Asp Cys Asp Ala Glu Lys Tyr
        35                  40                  45

Tyr Asn Met Tyr Lys His Gly Glu Asp Val Lys Lys Ala Val Pro His
    50                  55                  60

Leu Cys Val Asp Val Lys Ile Ile Ser Gly Asp Pro Thr Ser Ser Gly
65                  70                  75                  80

Cys Ile Lys Glu Trp Asn Val Asn Ile Asp Gly Lys Thr Ile Arg Ser
                85                  90                  95

Val Glu Glu Thr Thr His Asp Asp Glu Thr Lys Thr Leu Arg His Arg
            100                 105                 110

Val Phe Glu Gly Asp Val Met Lys Asp Phe Lys Lys Phe Asp Thr Ile
        115                 120                 125

Met Val Val Asn Pro Lys Pro Asp Gly Asn Gly Cys Val Val Thr Arg
    130                 135                 140

Ser Ile Glu Tyr Glu Lys Thr Asn Glu Asn Ser Pro Thr Pro Phe Asp
145                 150                 155                 160

Tyr Leu Gln Phe Gly His Gln Ala Ile Glu Asp Met Asn Lys Tyr Leu
                165                 170                 175

Arg Asp Ser Glu
            180

<210> SEQ ID NO 80
<211> LENGTH: 160
<212> TYPE: PRT
<213> ORGANISM: Papaver somniferum

<400> SEQUENCE: 80

Met Ala Pro Leu Gly Val Ser Gly Leu Val Gly Lys Leu Ser Thr Glu
1               5                   10                  15

Leu Glu Val Asp Cys Asp Ala Glu Lys Tyr Tyr Asn Met Tyr Lys His
            20                  25                  30

Gly Glu Asp Val Lys Lys Ala Val Pro His Leu Cys Val Asp Val Lys
        35                  40                  45

Ile Ile Ser Gly Asp Pro Thr Ser Ser Gly Cys Ile Lys Glu Trp Asn
    50                  55                  60

Val Asn Ile Asp Gly Lys Thr Ile Arg Ser Val Glu Glu Thr Thr His
65                  70                  75                  80

Asp Asp Glu Thr Lys Thr Leu Arg His Arg Val Phe Glu Gly Asp Val
                85                  90                  95

Met Lys Asp Phe Lys Lys Phe Asp Thr Ile Met Val Val Asn Pro Lys
            100                 105                 110

Pro Asp Gly Asn Gly Cys Val Val Thr Arg Ser Ile Glu Tyr Glu Lys
        115                 120                 125

```
Thr Asn Glu Asn Ser Pro Thr Pro Phe Asp Tyr Leu Gln Phe Gly His
    130                 135             140

Gln Ala Ile Glu Asp Met Asn Lys Tyr Leu Arg Asp Ser Glu Ser Asn
145             150                 155             160
```

RECOMBINANT HOST CELLS WITH IMPROVED PRODUCTION OF L-DOPA, DOPAMINE, S-NOROCLAURINE OR DERIVATIVES THEREOF

CROSS REFERENCE

This application is a U.S. national phase application under 35 U.S.C. § 371 of International Application No. PCT/EP2020/050610, filed Jan. 10, 2020, which claims the benefit of DK Application No. PA201900035, filed Jan. 11, 2019, the disclosures of each of which are explicitly incorporated by reference herein in their entirety.

FIELD OF THE INVENTION

The present invention relates to recombinant host cells producing the compounds L-DOPA, dopamine and (S)-Norcoclaurine or derivatives thereof using tyrosine hydroxylase; to recombinant polynucleotides comprising a sequence encoding tyrosine hydroxylase, operably linked to promoter nucleotide sequences facilitating expression of the tyrosine hydroxylase. Further, the invention relates to cell cultures comprising the host cell of the invention, to methods of producing the compounds of the invention; to fermentation liquids comprising the compounds resulting from such methods, to compositions comprising the fermentation liquid; to pharmaceutical preparations made from such compositions and to the use of such compositions and preparations.

BACKGROUND OF THE INVENTION

L-3,4-dihydroxyphenylalanine (L-DOPA) is an intermediate metabolite/precursor in the biosynthetic pathway for many compounds, including benzylisoquinoline alkaloids (BIAs), where L-DOPA is a key precursor in the formation of dopamine and in turn (S)-norcoclaurine, which is the first committed intermediate in BIA pathways. BIA are known to have diverse pharmaceutical properties including, for example, analgesic, antimicrobial, antitussive, antiparasitic, cytotoxic, and anticancer properties (Hagel & Facchini, 2013, Plant Cell Physiol. 54(5); 647-672). Thousands of distinct BIAS have been identified in plants, each of which derive from a common precursor: (S)-norcoclaurine (see e.g., Hagel & Facchini, 2013, Plant Cell Physiol. 54(5); 647-672; Fossati et al., 2015, PLoS ONE 10(4): e0124459).

While it is known that production of these complex alkaloid compounds, in planta, requires plant cells to perform a plethora of different enzyme mediated chemical reactions in concert (pathways). While it is in principle understood that plant enzyme polypeptides and polynucleotides encoding them, are instrumental for in planta synthesis of alkaloids, many aspects of alkaloid pathways are yet to be explored, not only which polypeptides are relevant for producing a particular alkaloids in nature, but also which polypeptides can be can be implemented to produce alkaloids ex planta, for example in heterologous host cells, and in particular which polypeptides are capable of producing better yields of desired alkaloids when produced by ex planta biosynthetic manufacturing methods.

L-tyrosine hydroxylases are polypeptides involved in hydroxylating L-tyrosine into L-DOPA. Galanie et al.: "Complete biosynthesis of opioids in yeast", Science, 2015, Vol 349, No. 6252, pages 1095-1100 pertains to an engineered biosynthetic pathway producing thebaine and hydrocodone in yeast including a genetically modified mammalian tyrosine hydroxylase from *Rattus norvegicus*. WO 2017/122189 (Yeda Research and Development Co) discloses sequences said to encode enzymes capable of converting tyrosine into L-DOPA and methods for producing L-DOPA in a cell using such enzymes. WO 2018/005553 (Facchini et al) asserts that BIAs can be produced in cells using the tyrosine hydroxylase CYP76AD1 for converting L-tyrosine to L-DOPA. WO2016/049364 (Martin et al.) and DELOACHE, C. W. et al.; Nature Chemical Biology; 2015; Vol. 11; pages 465-471, discloses a variant or mutant of CYP76AD1 tyrosine hydroxylases (referred to herein as SEQ ID NO: 58) said to provide for increased production of L-DOPA in host cells expressing this tyrosine hydroxylase.

SUMMARY OF THE INVENTION

The inventors of the present invention have identified L-tyrosine Hydroxylases (TyrH's), which not only surprisingly integrate and work in recombinant host cells, but also exhibit significant improvements in producing L-DOPA and subsequently dopamine, (S)-norcoclaurine or derivatives thereof in the host cell over hitherto known best TyrH's. Accordingly, in a first aspect the invention provides a recombinant microbial host cell comprising an operative biosynthetic metabolic pathway capable of producing one or more target compounds selected from the group consisting of L-dopa, dopamine, (S)-Norcoclaurine and derivatives thereof; said pathway comprising one or more heterologous L-tyrosine hydroxylases (TyrH) converting L-Tyrosine into L-dopa capable of increasing the cell production of the target compound(s) compared to a reference L-tyrosine hydroxylase having the sequence set forth in SEQ ID NO: 58.

In a further aspect the invention provides a nucleic acid construct comprising a polynucleotide sequence encoding the TyrH of the invention, operably linked to one or more control sequences heterologous to the TyrH encoding polynucleotide.

In a further aspect the invention provides an expression vector comprising the nucleic acid construct of the invention.

In a further aspect the invention provides a recombinant microbial host cell comprising the nucleic acid construct or the vector of the invention.

In a further aspect the invention provides a cell culture, comprising the host cell of the invention. and a growth medium.

In a further aspect the invention provides a method for producing at least one target compound selected from the group consisting of one or more of L-dopa, dopamine and (S)-Norcoclaurine or a derivative thereof comprising
a) culturing the cell culture of the invention at conditions allowing the host cell to produce the target compound; and
b) optionally recovering and/or isolating the target compound.

In a further aspect the invention provides a fermentation liquid comprising the at least one target compound selected from L-dopa, dopamine, (S)-Norcoclaurine and derivatives thereof comprised in the cell culture of the invention.

In a further aspect the invention provides a composition comprising the fermentation liquid of the invention and one or more agents, additives and/or excipients.

In a further aspect the invention provides a method for preparing a pharmaceutical preparation comprising subjecting a composition of the invention to one or more steps of converting the target compound in the composition to a pharmaceutically active derivative selected from the group consisting of Berberine, Papaverine, Morphine, Sanguinarine, Noscapine, Neomorphine, hydrocodone, Codeine, Oxycodone, Oxymorphone, Dihydromorphine and buprenorphine; and mixing the derivative with one or more pharmaceutical grade additives and/or adjuvants.

In a further aspect the invention provides a pharmaceutical preparation obtainable from the method of the invention for preparing the pharmaceutical preparation.

In a final aspect the invention provides a method for treating pain or opioid poisoning in a mammal comprising administering the pharmaceutical preparation of the invention to the mammal.

DESCRIPTION OF DRAWINGS AND FIGURES

INCORPORATION BY REFERENCE

Figure 1:
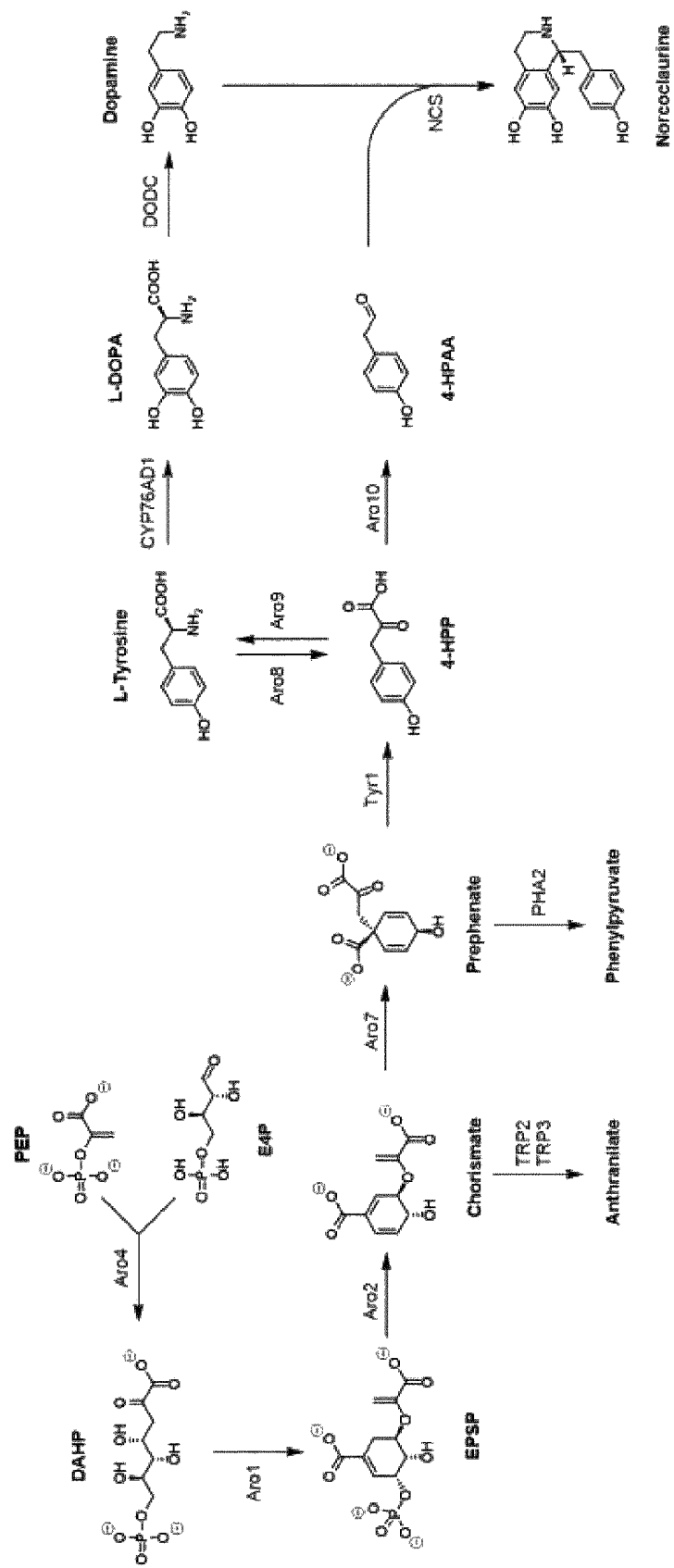
FIG. 1 depicts the Shikimate pathway to L-tyrosine and additional steps for producing (s)-norcoclaurine.
Figure 2:
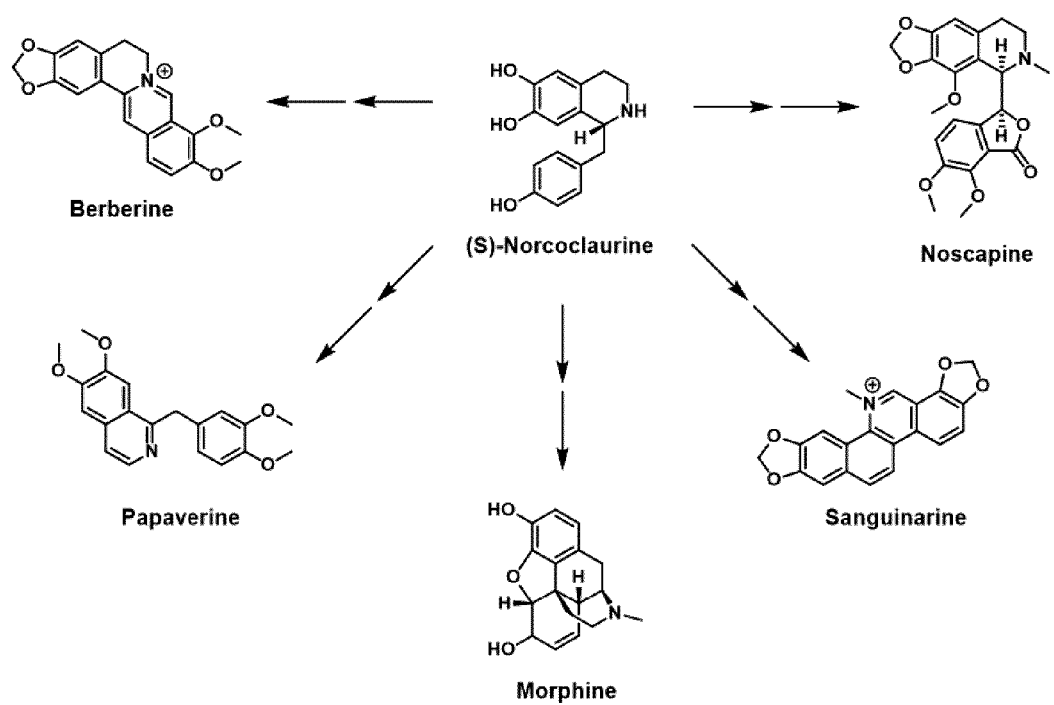
FIG. 2 depicts a range of compounds having pharmaceutical properties which are derivatives of (S)-norcoclaurine.
Figure 3:
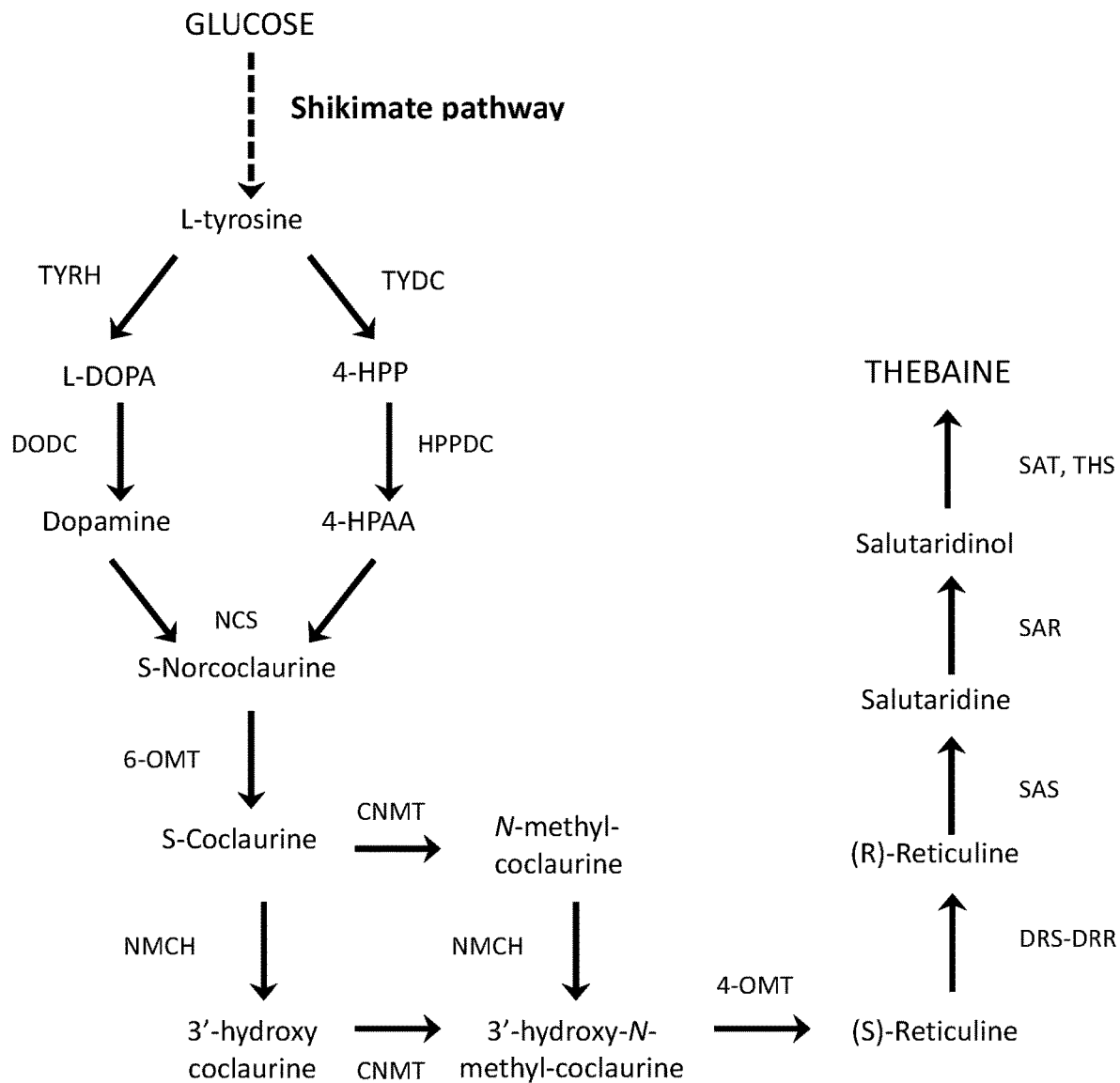
FIG. 3 depicts the pathway of steps for producing thebaine from glucose.

All publications, patents, and patent applications referred to herein are incorporated by reference to the same extent as if each individual publication, patent, or patent application was specifically and individually indicated to be incorporated by reference. In the event of a conflict between a term herein and a term in an incorporated reference, the term herein prevails and controls.

DETAILED DESCRIPTION OF THE INVENTION

Definitions

The term AUC as used herein refers to area under the curve, determined by the integration of the peaks representative of analytes described in Example 1.

The term "PEP" as used herein refers to phosphoenol pyruvate

The term "E4P" as used herein refers to erythrose-4-phosphate

The term "DAHP synthase" as used herein refers to an enzyme capable of DAHP synthase activity, thus having the ability to catalyze the reaction producing DAHP from PEP and E4P. Nonlimiting examples of DAHP synthases are ARO3; YDR035W; SGD:S000002442 and ARO4; YBR249C; SGD:S000000453 as disclosed in the *saccharomyces* genome database (SGD) at www.yeastgenome.org and natively found in *S. cerevisiae*.

The term "DAHP" as used herein refers to 3-deoxy-D-arabino-2-heptulosonic acid 7-phosphate.

The term "EPSP synthase" as used herein refers to an enzyme capable of catalyzing the conversion of DAHP into EPSP. A nonlimiting example of an EPSP synthase is ARO1; YDR127W; SGD:S000002534 as disclosed in the *saccharomyces* genome database (SGD) at www.yeastgenome.org and natively found in *S. cerevisiae*.

The term "EPSP" as used herein refers to 5-enolpyruvyl-shikimate-3-phosphate.

The term "chorismate synthase" as used herein refers to an enzyme capable of catalyzing the conversion of EPSP into chorismate. A nonlimiting example of a chorismite synthase is ARO2; YGL148W; SGD:S000003116 as disclosed in the *saccharomyces* genome database (SGD) at www.veastgenome.org; and natively found in *S. cerevisiae*.

The term "prephenate dehydrogenase" as used herein refers to an enzyme capable of catalyzing the conversion of prephenate into 4-HPP. A nonlimiting example of a prephenate dehydrogenase is TYR1 (YBR166C; SGD:S000000370 as disclosed in the *saccharomyces* genome database (SGD) at www.yeastgenome.org) natively found in *S. cerevisiae*.

The term "4-HPP" as used herein refers to 4-hydroxyphenylpyruvate

The term "aromatic aminotransferase" as used herein refers to an enzyme capable of catalyzing the conversion of 4-HPP into L-tyrosine. Nonlimiting examples of aromatic aminotransferases are ARO8 and ARO9 (YGL202W; SGD:S000003170 and YHR137W; SGD:S000001179 as disclosed in the *saccharomyces* genome database (SGD) at www.yeastgenome.org) natively found in *S. cerevisiae*.

The term "HPPDC" as used herein refers to hydroxyphenylpyruvate decarboxylase catalyzing 4-HPP into 4-HPAA. A nonlimiting example of an HPPDC is ARO10 (GenBank accession no. NP_010668.3) natively found in *S. cerevisiae*.

The term "4-HPAA" as used herein refers to 4-Hydroxyphenylacetaldehyde.

The term "TyrH" as used herein refers to tyrosine hydroxylase catalyzing L-tyrosine into L-DOPA.

The term "CPR" as used herein refers to P450 reductase catalyzing the electron transfer from NADPH to cytochrome P450, typically in the endoplasmic reticulum of a eukaryotic cell.

The term "Cytochrome P450 enzyme" or "P450 enzymes" or "P450" as used herein interchangeably refers to a family of monooxygenases enzymes containing heme as a cofactor. P450's are also known as "CYP's".

The term "DODC" and TYDC" as used herein refers to L-dopa decarboxylase and tyrosine decarboxylase respectively catalyzing conversion of L-DOPA into dopamine and tyrosine into 4-HPP.

The term "MAO" as used herein refers to monoamine oxidase catalyzing conversion of dopamine to 3,4 DHPAA The term "DHPAA" as used herein refers to 3,4-dihydroxyphenylacetaldehyde.

The term "NCS" as used herein refers to Norcoclaurine synthase catalyzing conversion of dopamine and 4-HPAA into Norcoclaurine.

The term "6-OMT" as used herein refers to 6-O-methyltransferase catalyzing conversion of (S)-norcoclaurine to (S)-Coclaurine The term "CNMT" as used herein refers to Coclaurine-N-methyltransferase catalyzing conversion of (S)-Coclaurine to (S)—N-Methylcoclaurine and (S)-3'-hydroxycoclaurine to (S)-3'-hydroxy-N-methylcoclaurine.

The term "NMCH" as used herein refers to N-methylcoclaurine 3'-monooxygenase catalyzing conversion of (S)-Coclaurine to (S)-3'-hydroxycoclaurine and (S)—N-Methylcoclaurine to (S)-3'-Hydroxy-N-Methylcoclaurine The term "4'-OMT" as used herein refers to 3'-hydroxy-N-methyl-(S)-coclaurine 4'-O-methyltransferase catalyzing conversion of (S)-3'-Hydroxy-N-Methylcoclaurine to (S)-Reticuline.

The term "DRS-DRR" as used herein refers to 1,2-dehydroreticuline synthase-1,2-dehydroreticuline reductase complex catalyzing conversion of (S)-Reticuline to (R)-Reticuline.

The term "SAS" as used herein refers to salutaridine synthase catalyzing conversion of (R)-Reticuline to Salutaridine.

The term "SAR" as used herein refers to salutaridine reductase catalyzing conversion of Salutaridine to Salutaridinol.

The term "SAT" as used herein refers to salutaridinol 7-O-acetyltransferase catalyzing conversion of Salutaridinol to 7-O-acylsalutaridinol.

The term "THS" as used herein refers to thebaine synthase catalyzing conversion of 7-O-acylsalutaridinol to thebaine.

The term "BIA" or "benzylisoquinoline alkaloid" as used herein refers to a compound of the general formula:

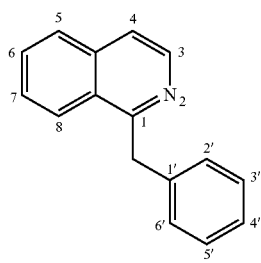

which is the structural backbone of many alkaloids with a wide variety of structures.

The term "heterologous" or "recombinant" and its grammatical equivalents as used herein refers to entities "derived from a different species or cell". For example, a heterologous or recombinant polynucleotide gene is a gene in a host cell not naturally containing that gene, i.e. the gene is modified to a non-naturally occurring form or it is from a different species or cell type than the host cell.

The term "recombinant host cell" as used herein refers to host cell comprising and expressing heterologous or recombinant polynucleotide genes.

The term "substrate" or "precursor", as used herein refers to any compound that can be converted into a different compound. For example, L-tyrosine can be a substrate for TyrH and can be converted into L-DOPA. For clarity, substrates and/or precursors include both compounds generated in situ by a enzymatic reaction in a cell or exogenously provided compounds, such as exogenously provided organic molecules which the host cell can metabolize into a desired compound.

The term "metabolic pathway" as used herein is intended to mean two or more enzymes acting sequentially in a live cell to convert chemical substrate(s) into chemical product (s). Enzymes are characterized by having catalytic activity, which can change the chemical structure of the substrate(s). An enzyme may have more than one substrate and produce more than one product. The enzyme may also depend on cofactors, which can be inorganic chemical compounds or organic compounds such as proteins for example enzymes (co-enzymes). The CPR that reduces the Cytochrome P450 is an example of an enzymatic co-factor. The term "operative biosynthetic metabolic pathway" refers to a metabolic pathway that occurs in a live recombinant host, as described herein.

The term "in vivo", as used herein refers to within a living cell, including, for example, a microorganism or a plant cell.

The term "in vitro", as used herein refers to outside a living cell, including, without limitation, for example, in a microwell plate, a tube, a flask, a beaker, a tank, a reactor and the like.

Term "endogenous" or "native" as used herein refers to a gene or a polypeptide in a host cell which originates from the same host cell.

The term "deletion" as used herein refers to manipulation of a gene so that it is no longer present or partially present, so that the gene is not expressed in a host cell.

The term "disruption" as used herein refers to the genetic manipulation of a gene or any of the machinery participating in the expression the gene, so that it is no longer expressed in a host cell. Non-limiting examples of methods of genetic disruption include nonsense mutations, knockouts, knock-ins, antisense silencing, and so on.

The term "attenuation" or "downregulation" as used herein refers to manipulation of a gene or any of the machinery participating in the expression the gene, so that it the expression of the gene is reduced as compared to expression without the manipulation.

The terms "substantially" or "approximately" or "about", as used herein refers to a reasonable deviation around a value or parameter such that the value or parameter is not significantly changed. These terms of deviation from a value should be construed as including a deviation of the value where the deviation would not negate the meaning of the value deviated from. For example, in relation to a reference numerical value the terms of degree can include a range of values plus or minus 10% from that value. For example, using these deviating terms can also include a range deviations plus or minus such as plus or minus 9%, 8%, 7%, 6%, 5%, 4%, 3%, 2%, or 1% from a specified value.

The term "and/or" as used herein is intended to represent an inclusive "or". The wording X and/or Y is meant to mean both X or Y and X and Y. Further the wording X, Y and/or Z is intended to mean X, Y and Z alone or any combination of X, Y, and Z.

The term "isolated" as used herein about a compound, refers to any compound, which by means of human intervention, has been put in a form or environment that differs from the form or environment in which it is found in nature. Isolated compounds include but is no limited to compounds of the invention for which the ratio of the compounds relative to other constituents with which they are associated in nature is increased or decreased. In an important embodiment the amount of compound is increased relative to other constituents with which the compound is associated in nature.

In an embodiment the compound of the invention may be isolated into a pure or substantially pure form. In this context a substantially pure compound means that the compound is separated from other extraneous or unwanted material present from the onset of producing the compound or generated in the manufacturing process. Such a substantially pure compound preparation contains less than 10%, such as less than 8%, such as less than 6%, such as less than 5%, such as less than 4%, such as less than 3%, such as less than 2%, such as less than 1%, such as less than 0.5% by weight of other extraneous or unwanted material usually associated with the compound when expressed natively or recombinantly. In an embodiment the isolated compound is at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by weight.

The term "non-naturally occurring" as used herein about a substance, refers to any substance that is not normally found in nature or natural biological systems. In this context the term "found in nature or in natural biological systems" does not include the finding of a substance in nature resulting from releasing the substance to nature by deliberate or accidental human intervention. Non-naturally occurring substances may include substances completely or partially synthetized by human intervention and/or substances prepared by human modification of a natural substance.

The term "% identity" is used herein about the relatedness between two amino acid sequences or between two nucleotide sequences.

The term "% identity" as used herein about amino acid sequences refers to the degree of identity in percent between two amino acid sequences obtained when using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$\frac{\text{identical amino acid residues}}{\text{Length of alignment} - \text{total number of gaps in alignment}} \times 100$$

The term "% identity" as used herein about nucleotide sequences refers to the degree of identity in percent between two nucleotide sequences obtained when using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$\frac{\text{identical deoxyribonucleotides}}{\text{Length of alignment} - \text{total number of gaps in alignment}} \times 100$$

The protein sequences of the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information.

BLASTP is used for amino acid sequences and BLASTN for nucleotide sequences. The BLAST program uses as defaults:
  Cost to open gap: default=5 for nucleotides/11 for proteins
  Cost to extend gap: default=2 for nucleotides/1 for proteins
  Penalty for nucleotide mismatch: default=−3
  Reward for nucleotide match: default=1
  Expect value: default=10
  Wordsize: default=11 for nucleotides/28 for megablast/3 for proteins Furthermore, the degree of local identity between the amino acid sequence query or nucleic acid sequence query and the retrieved homologous sequences is determined by the BLAST program. However only those sequence segments are compared that give a match above a certain threshold. Accordingly, the program calculates the identity only for these matching segments. Therefore, the identity calculated in this way is referred to as local identity.

The term "cDNA" refers to a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" refers to a nucleotide sequence, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequence" as used herein refers to a nucleotide sequence necessary for expression of a polynucleotide encoding a polypeptide. A control sequence may be native (i.e., from the same gene) or heterologous or foreign (i.e., from a different gene) to the polynucleotide encoding the polypeptide. Control sequences include, but are not limited to leader sequences, polyadenylation sequence, pro-peptide coding sequence, promoter sequences, signal peptide coding sequence, translation terminator (stop) sequences and transcription terminator (stop) sequences. To be operational control sequences usually must include promoter sequences, transcriptional and translational stop signals. Control sequences may be provided with linkers for the purpose of introducing specific restriction sites facilitating ligation of the control sequences with a coding region of a polynucleotide encoding a polypeptide.

The term "expression" includes any step involved in the production of a polypeptide including, but not limited to, transcription, post-transcriptional modification, translation, post-translational modification, and secretion.

The term "expression vector" refers to a DNA molecule, either single- or double stranded, either linear or circular, which comprises a polynucleotide encoding a polypeptide and is operably linked to control sequences that provide for its expression. Expression vectors include expression cassettes for the integration of genes into a host cell as well as plasmids and/or chromosomes comprising such genes.

The term "host cell" refers to any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "nucleic acid construct" refers to a nucleic acid molecule, either single- or double stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a control sequence is placed at an appropriate position relative to the coding polynucleotide such that the control sequence directs expression of the coding polynucleotide.

The terms "nucleotide sequence and "polynucleotide" are used herein interchangeably.

The term "comprise" and "include" as used throughout the specification and the accompanying claims as well as variations such as "comprises", "comprising", "includes" and "including" are to be interpreted inclusively. These words are intended to convey the possible inclusion of other elements or integers not specifically recited, where the context allows.

The articles "a" and "an" are used herein refers to one or to more than one (i.e. to one or at least one) of the grammatical object of the article. By way of example, "an element" may mean one element or more than one element.

Terms like "preferably", "commonly", "particularly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

The term "cell culture" as used herein refers to a culture medium comprising a plurality of recombinant host cells of the invention. A cell culture may comprise a single strain of recombinant host or may comprise two or more distinct host strains. The culture medium may be any medium that may comprise a recombinant host, e.g., a liquid medium (i.e., a culture broth) or a semi-solid medium, and may comprise additional components, e.g., a carbon source such as dextrose, sucrose, glycerol, or acetate; a nitrogen source such as ammonium sulfate, urea, or amino acids; a phosphate source; vitamins; trace elements; salts; amino acids; nucleobases; yeast extract; aminoglycoside antibiotics such as G418 and hygromycin B.

Recombinant Host Cells

The invention provides the first aspect recombinant microbial host cell comprising an operative biosynthetic metabolic pathway capable of producing one or more target compounds selected from the group consisting of L-dopa, dopamine, (S)-Norcoclaurine and derivatives thereof; said pathway comprising one or more heterologous L-tyrosine hydroxylases (TyrH) converting L-Tyrosine into L-dopa capable of increasing the cell production of the target compound(s) compared to a host cell using the hitherto best known reference TyrH having the sequence set forth in SEQ ID NO: 58. In a particular embodiment the host cell increases production of the target compound(s) by at least 50%, such as at least 100%, such as least 150%, such as at least 200%. In particular the inventors have found a group of TyrH which performs particularly well and in an embodiment the one or more TyrH of the invention has at least 70% identity to a polypeptide selected from the group consisting of SEQ ID NO: 2; to SEQ ID NO: 4; to SEQ ID NO: 10; to SEQ ID NO: 6; to SEQ ID NO: 24; to SEQ ID NO: 8; to SEQ ID NO: 12; to SEQ ID NO: 14; and/or to SEQ ID NO: 16. In a more specific embodiment the TyrH has at least 75%, such as at least 80%, such as at least 90%, such as at least 95%, such as at least 99%, such as at least 100% identity to a polypeptide selected from the group consisting of SEQ ID NO: 2; to SEQ ID NO: 4; to SEQ ID NO: 10; to SEQ ID NO: 6; to SEQ ID NO: 24; to SEQ ID NO: 8; to SEQ ID NO: 12; to SEQ ID NO: 14; and/or to SEQ ID NO: 16.

In an embodiment, the operative biosynthetic metabolic pathway in the host cell of the invention further comprises and expresses one or more genes encoding additional pathway enzyme polypeptides selected from the group consisting of:
a) DAHP synthase;
b) EPSP synthase
c) chorismate synthase;
d) chorismate mutase;
e) prephenate dehydrogenase;
f) aromatic aminotransferase;
g) CPR;
h) DODC;
i) TYDC;
j) HPPDC;
k) MAO;
l) NCS;
m) 6-OMT;
n) CNMT;
o) NMCH;
p) 4'-OMT;
q) DRS-DRR;
r) SAS;
s) SAR;
t) SAT and
u) THS.

In an embodiment the host cell comprise all enzyme polypeptides required to produce a desired compound from simple nutrient substrates such as glucose fed from a fermentation medium. However, since substrates and precursors may be provided to the host cell exogenously, the host cell pathway may comprise any combination of selected pathway enzyme polypeptides, depending on the exogenously provided precursor and the compound desired to be produced by the host cell.

In an embodiment the operative pathway in the host cell comprises DAHP synthase; EPSP synthase chorismate synthase; chorismate mutase; prephenate dehydrogenase; aromatic aminotransferase; CPR; DODC; TYDC; HPPDC; and NCS. More specifically the chorismate mutase; CPR; DODC; TYDC; and NCS may all be heterologous to the host cell.

In a further embodiment the operative pathway in the host cell comprises DAHP synthase; EPSP synthase chorismate synthase; chorismate mutase; prephenate dehydrogenase; aromatic aminotransferase; CPR; DODC; TYDC; HPPDC; NCS; 6-OMT; CNMT; NMCH; 4'-OMT; DRS-DRR; SAS; SAR; SAT; and optionally THS. Conversion of 7-O-acyl-salutaridinol into thebaine may occur to a certain extent spontaneously, but the rate can be significantly increased by inclusion of THS.

In an embodiment the corresponding:
a) DAHP synthase is a native yeast DAHP synthase, such as the ARO3; YDR035W; SGD:S000002442 or ARO4; YBR249C; SGD:S000000453 as disclosed in the *saccharomyces* genome database (SGD);
b) EPSP synthase is a native yeast EPSP synthase such as the ARO1; YDR127W; SGD:S000002534 as disclosed in the *saccharomyces* genome database (SGD);
c) chorismate synthase is a native yeast chorismate synthase such as the ARO2; YGL148W; SGD:S000003116 as disclosed in the *saccharomyces* genome database (SGD);
d) chorismate mutase is a native yeast chorismate mutase and/or chorismate mutase which has at least 70%, such as at least 75%, such as at least 80%, such as at least 90%, such as at least 95%, such as at least 99%, such as at least 100% identity to the chorismate synthase of SEQ ID NO: 77, or alternatively the ARO7; YPR060C; SGD:S000006264 as disclosed in the *saccharomyces* genome database (SGD);

e) prephenate dehydrogenase is a native yeast prephenate dehydrogenase such as the TYR1; YBR166C; SGD: S000000370 as disclosed in the *saccharomyces* genome database (SGD);

f) aromatic aminotransferase is a native yeast aromatic aminotransferase such as the ARO8; YGL202W; SGD: S000003170 or ARO9; YHR137W; SGD:S000001179 as disclosed in the *saccharomyces* genome database (SGD);

g) CPR has at least 70%, such as at least 75%, such as at least 80%, such as at least 90%, such as at least 95%, such as at least 99%, such as at least 100% identity to the CPR of SEQ ID NO: 76;

h) DODC has at least 70%, such as at least 75%, such as at least 80%, such as at least 90%, such as at least 95%, such as at least 99%, such as at least 100% identity to the DODC of SEQ ID NO: 60; and/or is encoded by the gene disclosed in GenBank accession no. AE015451.

i) TYDC is encoded by the gene disclosed in GenBank accession nos. P54768 (*Papaver somniferum*); GenBank accession nos. U08597 (*Papaver somniferum*); or GenBank accession no. AF314150 (Thalictrum flavum);

j) HPPDC is encoded by the gene disclosed in GenBank accession no. NP_010668.3 (*S. cerevisiae*);

k) MAO is encoded by the gene disclosed in GenBank accession no. AB010716 (*Micrococcus luteus*);

l) NCS has at least 70%, such as at least 75%, such as at least 80%, such as at least 90%, such as at least 95%, such as at least 99%, such as at least 100% identity to the NCS of SEQ ID NO: 61 or SEQ ID NO: 75; and/or is the NCS of SEQ ID NO: 24 disclosed in WO2018/029282 (*S. cerevisiae* codon optimised) or the NCS's disclosed in DK patent application PA 2017 70533 or is encoded by the gene disclosed in GenBank accession no. AB267399.2 (*Coptis japonica*):

m) 6-OMT has at least 70%, such as at least 75%, such as at least 80%, such as at least 90%, such as at least 95%, such as at least 99%, such as at least 100% identity to the 6-OMY of SEQ ID NO: 62; or is the 6-OMT encoded by the gene disclosed in GenBank accession no. Q6WUC1 (*Papaver somniferum*) or GenBank accession no. D29811 (*Coptis japonica*);

n) CNMT has at least 70%, such as at least 75%, such as at least 80%, such as at least 90%, such as at least 95%, such as at least 99%, such as at least 100% identity to the CNMT of SEQ ID NO: 63; or is the CNMT encoded by the gene disclosed in GenBank accession no. Q948P7 (*Coptis japonica*) or GenBank accession no. AY610508 (Thalictrum flavum) or GenBank accession no. AY217336 (*Papaver somniferum*);

o) NMCH has at least 70%, such as at least 75%, such as at least 80%, such as at least 90%, such as at least 95%, such as at least 99%, such as at least 100% identity to the NMCH of SEQ ID NO: 65; or is the NMCH encoded by the gene disclosed in GenBank accession no. 064899 (*Papaver somniferum*);

p) 4'-OMT has at least 70%, such as at least 75%, such as at least 80%, such as at least 90%, such as at least 95%, such as at least 99%, such as at least 100% identity to the 4'-OMT of SEQ ID NO: 66; or is the 4'-OMT encoded by the gene disclosed in GenBank accession no. Q9LEL5 (*Coptis japonica*);

q) DRS-DRR has at least 70%, such as at least 75%, such as at least 80%, such as at least 90%, such as at least 95%, such as at least 99%, such as at least 100% identity to the DRS-DRR of SEQ ID NO: 68; or is the DRS-DRR encoded by the gene disclosed in GenBank accession no. P0DKI7 (*Papaver somniferum*) or the DRS-DRR disclosed in Smolke et al.; Science. 2015 Sep. 4; 349(6252): 1095-1100;

r) SAS has at least 70%, such as at least 75%, such as at least 80%, such as at least 90%, such as at least 95%, such as at least 99%, such as at least 100% identity to the SAS of SEQ ID NO: 70; or is the SAS encoded by the gene disclosed in GenBank accession no. EF451150 (*Papaver somniferum*);

s) SAR has at least 70%, such as at least 75%, such as at least 80%, such as at least 90%, such as at least 95%, such as at least 99%, such as at least 100% identity to the SAR of SEQ ID NO: 71; or is the SAR encoded by the gene disclosed in GenBank accession no. DQ316261 (*Papaver somniferum*)

t) SAT has at least 70%, such as at least 75%, such as at least 80%, such as at least 90%, such as at least 95%, such as at least 99%, such as at least 100% identity to the SAT of SEQ ID NO: 73; or is the SAT encoded by the gene disclosed in GenBank accession no. AF339913 (*Papaver somniferum*); and u) THS has at least 70%, such as at least 75%, such as at least 80%, such as at least 90%, such as at least 95%, such as at least 99%, such as at least 100% identity to the THS of SEQ ID NO: 79 or SEQ ID NO: 80.

In a particular embodiment the operative biosynthetic metabolic pathway of the invention comprises:

a) chorismate mutase having at least 95% identity to the chorismate synthase of SEQ ID NO: 77;

b) CPR having at least 95% to the CPR of SEQ ID NO: 76;

c) DODC having at least 95% to the DODC of SEQ ID NO: 60;

d) TyrH having at least 95% to the TyrH of SEQ ID NO: 2;

e) NCS having at least 95% to the NCS of SEQ ID NO: 61 or SEQ ID NO: 75;

f) 6-OMT having at least 95% to the 6-OMT of SEQ ID NO: 62;

g) CNMT having at least 95% to the CNMT of SEQ ID NO: 63;

h) NMCH having at least 95% to the NMCH of SEQ ID NO: 65;

i) 4'-OMT having at least 95% to the 4'-OMT of SEQ ID NO: 66;

j) DRS-DRR having at least 95% to the DRS-DRR of SEQ ID NO: 68;

k) SAS which has at least 95% to the SAS of SEQ ID NO: 70;

l) SAR which has at least 95% to the SAR of SEQ ID NO: 71;

m) SAT having at least 95% to the SAT of SEQ ID NO: 73; and n) THS having at least 95% to the THS of SEQ ID NO: 79 or SEQ ID NO: 80.

The recombinant host cell of the invention is capable of producing one or more target compounds selected from L-dopa, dopamine and (S)-Norcoclaurine or derivatives thereof. In an embodiment the derivatives of L-dopa, dopamine and (S)-Norcoclaurine is a benzylisoquinoline alkaloid (BIA) and more specifically the BIA may selected from one or more of (5)-Norcoclaurine; (5)-Norlaudanosoline;

(5)-Coclaurine; (S)-3'-Hydroxy-coclaurine; (S)—N-Methylcoclaurine; (S)-3'-Hydroxy-N-Methylcoclaurine; (5)-Reticuline; (R)-Reticuline; Salutaridine; Salutaridinol; and Thebaine. In particular the BIA is Thebaine.

One or more enzyme polypeptides of the operative biosynthetic metabolic pathway of invention are heterologous to the recombinant host cell host and particularly a plurality of enzyme polypeptides are heterologous such as 2, 3, 4, 5, 6, 7, 8, 9, 10, 11, 12, 13, 14, 15, 16, 17, 17, 18, 19 or 20 of the pathway enzyme polypeptides are heterologous to the host cell.

The host cell is in one embodiment a eukaryotic cell selected from the group consisting of mammalian, insect, plant, or fungal cells. The host cell may be a fungal cell selected from phylas consisting of Ascomycota, Basidiomycota, Neocallimastigomycota, Glomeromycota, Blastocladiomycota, Chytridiomycota, Zygomycota, Oomycota and Microsporidia. In particular the host cell is a yeast cell selected from the group consisting of ascosporogenous yeast (Endomycetales), basidiosporogenous yeast, and Fungi Imperfecti yeast (Blastomycetes), particularly a yeast cell is selected from the genera consisting of *Saccharomyces, Kluveromyces, Candida, Pichia, Debaromyces, Hansenula, Yarrowia, Zygosaccharomyces*, and *Schizosaccharomyces*. For specific species the yeats host cell may be selected from the species consisting of *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, and *Yarrowia lipolytica*. In another embodiment the host cell is filamentous fungus. Suitable filamentous fungal host cell may be selected among the phylas consisting of Ascomycota, Eumycota and Oomycota, particularly selected from the genera of *Acremonium, Aspergillus, Aureobasidium, Bjerkandera, Ceriporiopsis, Chrysosporium, Coprinus, Corio/us, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma*. More specially a filamentous fungal host cell may be selected among the species of *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora*, Chrysosporiuminops, Chrysosporiumkeratinophilum, *Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminurn, Fusarium heterosporum, Fusarium negundi, Fusarium oxysporum, Fusarium reticulatum, Fusarium roseum, Fusarium sambucinurn, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenurn, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, and *Trichoderma viride*.

The host cell of the invention may also be further genetically modified to provide an increased amount of substrate for at least one enzyme polypeptide of the operative biosynthetic metabolic pathway and/or the host cell may be further genetically modified to exhibit increased tolerance towards one or more substrates, intermediates, or product molecules from enzyme polypeptides of the operative biosynthetic metabolic pathway.

In the alternative the host cell may be a plant cell for example of the genus *Physcomitrella*. In addition to plant cells the invention also provides an isolated plant, e.g., a transgenic plant, plant part comprising the pathway and TyrH of the invention and producing the compounds of the invention in useful quantities. The compound may be recovered from the plant or plant part. The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats. Also included within the scope of the present invention are the progeny of such plants, plant parts, and plant cells. The transgenic plant or plant cells comprising the operative pathway of the invention and produce the compound of the invention may be constructed in accordance with methods known in the art. In short, the plant or plant cell is constructed by incorporating one or more expression vectors of the invention into the plant host genome or chloroplast genome and propagating the resulting modified plant or plant cell into a transgenic plant or plant cell. The expression vector conveniently comprises the nucleic acid construct of the invention. The choice of regulatory sequences, such as promoter and terminator sequences and optionally signal or transit sequences, is determined, for example, on the basis of when, where, and how the pathway polypeptides is desired to be expressed. For instance, the expression of a gene encoding a pathway enzyme polypeptide may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506. For constitutive expression, the 358-CaMV, the maize ubiquitin 1, or the rice actin 1 promoter may be used (Franck et al., 1980, Cell 21: 285-294; Christensen et al., 1992, Plant Mol. Biol. 18: 675-689; Zhang et al., 1991, Plant Cell 3: 1155-1165). Organ-specific promoters may be, for example, a promoter from storage sink tissues such as seeds, potato tubers, and fruits (Edwards and Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant Cell Physiol. 39: 885-889), a *Vicia faba* promoter from the legumin B4 and the unknown seed protein gene from *Vicia faba* (Conrad et al., 1998, J. Plant Physiol. 152: 708-711), a promoter from a seed oil body protein (Chen et al., 1998, Plant Cell Physiol. 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiol. 102: 991-1000), the *chlorella* virus adenine methyltransferase gene promoter (Mitra and Higgins, 1994, Plant Mol. Biol. 26: 85-93), the aldP gene promoter from rice (Kagaya et al., 1995, Mol. Gen. Genet. 248: 668-674), or a wound inducible promoter such as the potato pint promoter (Xu et al., 1993, Plant Mol. Biol. 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals. A promoter enhancer element may also be used to achieve higher expression in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression. The selectable marker gene and any other parts of the expression construct may be chosen from those available in the art. The nucleic acid construct or expression vector is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274). *Agrobacterium tumefaciens*-mediated gene transfer is a method for generating transgenic dicots (for a review, see Hooykas and Schilperoort, 1992, Plant Mol. Biol. 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, Plant J. 2: 275-281; Shimamoto, 1994, Curr. Opin. Biotechnol. 5: 158-162; Vasil et al., 1992, Bio/Technology 10: 667-674). An alternative method for transformation of monocots is based on protoplast transformation as described by Omirulleh et al., 1993, Plant Mo/. Biol. 21: 415-428. Additional transformation methods include those described in U.S. Pat. Nos. 6,395,966 and 7, 151,204 (both incorporated herein by reference in their entirety). Following transformation, the transformants having incorporated the expression vector or nucleic acid construct of the invention are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase. In addition to direct transformation of a particular plant genotype with a nucleic acid construct of the invention, transgenic plants may be made by crossing a plant comprising the construct to a second plant lacking the construct. For example, a nucleic acid construct encoding a TyrH of the invention can be introduced into a particular plant variety by crossing, without the need for ever directly transforming a plant of that given variety. Therefore, the invention encompasses not only a plant directly regenerated from cells which have been transformed in accordance with the invention, but also the progeny of such plants. As used herein, progeny may refer to the offspring of any generation of a parent plant prepared in accordance with the present invention. Such progeny may include a nucleic acid construct of the invention. Crossing results in the introduction of a transgene into a plant line by cross pollinating a starting line with a donor plant line. Non-limiting examples of such steps are described in U.S. Pat. No. 7,151,204. Plants may be generated through a process of backcross conversion. For example, plants include plants referred to as a backcross converted genotype, line, inbred, or hybrid. Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

Nucleotide Constructs

The invention also provides a nucleic acid construct comprising a polynucleotide sequence encoding the TyrH of the invention, operably linked to one or more control sequences heterologous to the TyrH encoding polynucleotide.

Polynucleotides may be manipulated in a variety of ways allow expression of the TyrH. Manipulation of the polynucleotide prior to its insertion into an expression vector may be desirable or necessary depending on the expression vector. The techniques for modifying polynucleotides utilizing recombinant DNA methods are well known in the art.

The control sequence may be a promoter, which is a polynucleotide that is recognized by a host cell for expression of a polynucleotide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell. The promoter may be an inducible promoter.

Examples of suitable promoters for directing transcription of the nucleic acid construct of the invention in a filamentous fungal host cell are promoters obtained from the genes for *Aspergillus nidulans* acetamidase, *Aspergillus niger* neutral α-amylase, *Aspergillus niger* acid stable α-amylase, *Aspergillus niger* or *Aspergillus awamori* glucoamylase (glaA), *Aspergillus* gpdA promoter, *Aspergillus oryzae* TAKA amylase, *Aspergillus oryzae* alkaline protease, *Aspergillus oryzae* triose phosphate isomerase, *A. niger* or *A. awamori* endoxylanase (xlnA) or β-xylosidase (xlnD), *Fusarium oxysporum* trypsin-like protease (WO 96/00787), *Fusarium venenatum* amyloglucosidase (WO2000/56900), *Fusarium venenatum* Dania (WO200056900), *Fusarium venenatum* Quinn (WO200056900), *Rhizomucor miehei* lipase, *Rhizo-* mucor miehei aspartic proteinase, *Trichoderma reesei* β-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* β-xylosidase, as well as the NA2-tpi promoter and mutant, truncated, and hybrid promoters thereof. NA2-tpi promoter is a modified promoter from an *Aspergillus* neutral α-amylase gene in which the untranslated leader has been replaced by an untranslated leader from an *Aspergillus* triose phosphate isomerase gene. Examples of such promoters include modified promoters from an *Aspergillus niger* neutral α-amylase gene in which the untranslated leader has been replaced by an untranslated leader from an *Aspergillus nidulans* or *Aspergillus oryzae* triose phosphate isomerase gene. Other examples of promoters are the promoters described in WO2006/092396, WO2005/100573 and WO2008/098933, incorporated herein by reference.

Examples of suitable promoters for directing transcription of the nucleic acid construct of the invention in a yeast host include the glyceraldehyde-3-phosphate dehydrogenase promoter, PgpdA or promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488. Selecting a suitable promoter for expression in yeast is well know and is well understood by persons skilled in the art.

The control sequence may also be a transcription terminator, which is recognized by a host cell to terminate transcription. The terminator is operably linked to the 3'-terminus of the polynucleotide encoding the polypeptide. Any terminator that is functional in the host cell may be used.

Useful terminators for filamentous fungal host cells are obtained from the genes for *Aspergillus nidulans* anthranilate synthase, *Aspergillus niger* glucoamylase, *Aspergillus niger* α-glucosidase, *Aspergillus oryzae* TAKA amylase, and *Fusarium oxysporum* trypsin-like protease.

Useful terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* α-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Useful polyadenylation sequences for filamentous fungal host cells are obtained from the genes for *Aspergillus nidulans* anthranilate synthase, *Aspergillus niger* glucoamylase, *Aspergillus niger* α-glucosidase *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound.

In filamentous fungi, the *Aspergillus niger* glucoamylase promoter, *Aspergillus oryzae* TAKA α-amylase promoter, and *Aspergillus oryzae* glucoamylase promoter may be used.

In yeast, the ADH2 system or GAL 1 system may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals.

In a particular embodiment the TyrH encoding polynucleotide in the nucleic acid construct of the invention is selected from the group of:

a) a polynucleotide having at least 70%, such at least 75%, such as at least 80%, such as at least 90%, such as at least 95%, such as at least 99%, such as at least 100% identity to SEQ ID NO: 1;

b) a polynucleotide having at least 70%, such at least 75%, such as at least 80%, such as at least 90%, such as at least 95%, such as at least 99%, such as at least 100% identity to SEQ ID NO: 3;

c) a polynucleotide having at least 70%, such at least 75%, such as at least 80%, such as at least 90%, such as at least 95%, such as at least 99%, such as at least 100% identity to SEQ ID NO: 9;

d) a polynucleotide having at least 70%, such at least 75%, such as at least 80%, such as at least 90%, such as at least 95%, such as at least 99%, such as at least 100% identity to SEQ ID NO: 5;

e) a polynucleotide having at least 70%, such at least 75%, such as at least 80%, such as at least 90%, such as at least 95%, such as at least 99%, such as at least 100% identity to SEQ ID NO: 23;

f) a polynucleotide having at least 70%, such at least 75%, such as at least 80%, such as at least 90%, such as at least 95%, such as at least 99%, such as at least 100% identity to SEQ ID NO: 7;

g) a polynucleotide having at least 70%, such at least 75%, such as at least 80%, such as at least 90%, such as at least 95%, such as at least 99%, such as at least 100% identity to SEQ ID NO: 11;

h) a polynucleotide having at least 70%, such at least 75%, such as at least 80%, such as at least 90%, such as at least 95%, such as at least 99%, such as at least 100% identity to SEQ ID NO: 13; and
i) a polynucleotide having at least 70%, such at least 75%, such as at least 80%, such as at least 90%, such as at least 95%, such as at least 99%, such as at least 100% identity to SEQ ID NO: 15.

Expression Vectors

The invention also provides an expression vector comprising the nucleic acid construct of the invention. Various nucleotide sequences in addition to the nucleic acid construct of the invention may be joined together to produce a recombinant expression vector, which may include one or more convenient restriction sites to allow for insertion or substitution of the polynucleotide sequence encoding the TyrH of the invention at such sites. The recombinant expression vector may be any vector (e.g., a plasmid or virus) that can be conveniently subjected to recombinant DNA procedures and can bring about expression of the TyrH encoding polynucleotide. The choice of the vector will typically depend on the compatibility of the vector with the host cell into which the vector is to be introduced.

The vector may be a linear or closed circular plasmid. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may, when introduced into the host cell, integrate into the genome and replicate together with the chromosome(s) into which it has been integrated. Furthermore, a single vector or plasmid or two or more vectors or plasmids that together contain the total DNA to be introduced into the genome of the host cell, or a transposon, may be used. The vector may contain one or more selectable markers that permit easy selection of transformed, transfected, transduced, or the like cells. A selectable marker is a gene from which the product provides for biocide or viral resistance, resistance to heavy metals, prototrophy to auxotrophs, and the like.

Useful selectable markers for filamentous fungal host cell include amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. *Aspergillus nidulans* or *Aspergillus oryzae* amdS and pyrG genes and a *Streptomyces hygroscopicus* bar gene are particularly useful in *Aspergillus* cells.

Useful selectable markers for yeast host cells include, but are not limited to, ADE2, HIS3, LEU2, L YS2, MET3, TRP1, and URA3.

The vector preferably contains element(s) that permits integration of the vector into the host cell's genome or permits autonomous replication of the vector in the cell independent of the genome. For integration into the host cell genome, the vector may rely on the polynucleotide encoding the polypeptide or any other element of the vector for integration into the genome by homologous or non-homologous recombination. Alternatively, the vector may contain additional polynucleotides for directing integration by homologous recombination into the genome of the host cell at precise location(s) in the chromosome(s). To increase the likelihood of integration at a precise location, the integrational elements should contain a sufficient number of nucleic acids, such as 100 to 10,000 base pairs, such as 400 to 10,000 base pairs, and such as 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" refers to a polynucleotide that enables a plasmid or vector to replicate in vivo.

Useful origins of replication for filamentous fungal cell include AMA 1 and ANSI. (Gems et al., 1991, Gene 98: 61-67; Cullen et al., 1987, Nucleic Acids Res. 15: 9163-9175; WO 00/24883). Isolation of the AMA 1 gene and construction of plasmids or vectors comprising the gene can be accomplished using the methods disclosed in WO 00/24883.

Useful origins of replication for yeast host cell are the 2 micron origin of replication, ARS1, ARS4, the combination of ARS1 and CEN3, and the combination of ARS4 and CEN6.

More than one copy of a polynucleotide encoding the TyrH or other pathway enzyme polypeptides of the invention may be inserted into a host cell to increase production of an enzyme's polypeptide. An increase in the copy number can be obtained by integrating one or more additional copies of the enzyme coding sequence into the host cell genome or by including an amplifiable selectable marker gene with the polynucleotide, so that cells containing amplified copies of the selectable marker gene—and thereby additional copies of the polynucleotide—can be selected by cultivating the cells in the presence of the appropriate selectable agent. The procedures used to ligate the elements described above to construct the recombinant expression vectors of the present invention are well known to one skilled in the art (see, e.g., Sambrook et al., 1989, supra).

Accordingly, the invention also provides a recombinant host cell comprising the nucleic acid construct or the expression vector of the invention. In particular host cell comprise multiple copies of the TyrH coding polynucleotide sequence and/or of polynucleotide sequences encoding one or more pathway enzyme polypeptides of the invention. Moreover, one or more native genes of the host cell of the invention can be attenuated, disrupted and/or deleted. In one embodiment the host cell is a *S. cerevisiae* strain modified to delete the native gene ARI1; YGL157W; SGD:S000003125 as disclosed in the *saccharomyces* genome database (SGD) at www.yeastgenome.org.

Cultures

The invention also provides a cell culture, comprising the host cell of the invention. and a growth medium. Suitable growth medium for host cells such as plant cell lines, filamentous fungi and/or yeast are known in the art.

Methods of Producing Compounds of the Invention.

The invention also provides a method for producing at least one target compound selected from the group consisting of one or more of L-dopa, dopamine and (S)-Norcoclaurine or a derivative thereof comprising
a) culturing the cell culture of the invention at conditions allowing the host cell to produce the target compound; and b) optionally recovering and/or isolating the target compound.

The cell culture is cultivated in a nutrient medium suitable for production of the compound of the invention and/or propagating cell count using methods known in the art. For example, the culture may be cultivated by shake flask cultivation, or small-scale or large-scale fermentation (including continuous, batch, fed-batch, or solid-state fermentations) in laboratory or industrial fermenters in a suitable medium and under conditions allowing the pathway to operate to produce the compound of the invention and optionally to be recovered and/or isolated.

The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The selection of the appropriate medium may be based on the choice of host cell and/or based on the regulatory requirements for the host cell. Such media are in the art. The medium may, if desired, contain additional components favoring the transformed expression hosts over other potentially contaminating microorganisms. Accordingly, in an embodiment a suitable nutrient medium comprise a carbon source (e.g. glucose, maltose, molasses, starch, cellulose, xylan, pectin, lignocellolytic biomass hydrolysate, etc.), a nitrogen source (e. g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.).

The cultivating of the host cell may be performed over a period of from about 0.5 to about 30 days. The cultivation process may be a batch process, continuous or fed-batch process, suitably performed at a temperature in the range of 0-100° C. or 0-80° C., for example, from about 0° C. to about 50° C. and/or at a pH, for example, from about 2 to about 10. Preferred fermentation conditions for yeast and filamentous fungi are a temperature in the range of from about 25° C. to about 55° C. and at a pH of from about 3 to about 9. The appropriate conditions are usually selected based on the choice of host cell. Accordingly, in an embodiment the method of the invention further comprises one or more elements selected from:
a) culturing the cell culture in a nutrient medium;
b) culturing the cell culture under aerobic or anaerobic conditions
c) culturing the cell culture under agitation;
d) culturing the cell culture at a temperature of between 25 to 50° C.;
e) culturing the cell culture at a pH of between 3-9; and
f) culturing the cell culture for between 10 hours to 30 days.

The target compound(s) of the invention may be recovered and or isolated using methods known in the art. For example, the compound(s) may be recovered from the nutrient medium by conventional procedures including, but not limited to, collection, centrifugation, filtration, extraction, spray-drying, evaporation, or precipitation. The compound may be isolated by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989). In a particular embodiment the recovering and/or isolation step of the method of the invention comprises separating a liquid phase of the host cell or cell culture from a solid phase of the host cell or cell culture to obtain a supernatant comprising the at least one target compound and subjecting the supernatant to one or more steps selected from:
a) contacting the supernatant with one or more adsorbent resins in order to obtain at least a portion of the produced target compound;
b) contacting the supernatant with one or more ion exchange or reversed-phase chromatography columns in order to obtain at least a portion of the target compound; and
c) crystallizing or extracting the target compound from the supernatant; and
d) evaporating the solvent of the from the supernatant to concentrate or precipitate the target compound;
thereby recovering and/or isolating the target compound.

Not all conversion steps of pathway to produce the target compound of the invention need to occur in vivo in the host cell, so in a particular embodiment one or more of these steps are carried out in vitro. Accordingly, in an embodiment the method of the invention comprises at least one pathway step which is performed in vitro. Preferred target compounds to be produced using the method of the invention are listed supra.

Fermentation Liquids

The invention also provides a fermentation liquid comprising the at least one target compound of the invention comprised in the cultivated cell culture of the invention. Preferably, at least 50%, such as at least 75%, such as at least 95%, such as at least 99% of the host cells of the culture are lysed and preferably at least 50%, such as at least 75%, such as at least 95%, such as at least 99% of solid cellular material has separated from the liquid. In an embodiment the fermentation liquid further comprises one or more compounds selected from:
a) Precursor or products of the operative biosynthetic metabolic pathway producing the at least one target compound of the invention;
b) supplemental nutrients comprising trace metals, vitamins, salts, yeast nitrogen base, YNB, and/or amino acids; and
wherein the concentration of the compound of the invention at least 1 mg/L fermentation liquid.

Preferably, the concentration of the at least target compound in the fermentation liquid is at least 5 mg/L, such as at least 10 mg/L, such as at least 20 mg/l, such as at least 50 mg/L, such as at least 100 mg/L, such as at least 500 mg/L, such as at least 1000 mg/L, such as at least 5000 mg/L, such as at least 10000 mg/L, such as at least 50000 mg/L.

Compositions

In a further aspect the invention provides a composition comprising the fermentation liquid of the invention and one or more agents, additives and/or excipients. Agents, additives and/or excipients includes formulation additives, stabilising agent and fillers.

The composition of the invention may be formulated into a dry solid form by using methods known in the art. Further, the composition may be in dry form such as a spray dried, spray cooled, lyophilized, flash frozen, granular, microgranular, capsule or microcapsule form made using methods known in the art.

The composition of the invention may also be formulated into liquid stabilized form using methods known in the art. Further, the composition may be in liquid form such as a stabilized liquid comprising one or more stabilizers such as sugars and/or polyols (e.g. sugar alcohols) and/or organic acids (e.g. lactic acid).

Pharmaceutical Preparations

The invention further provides a method for preparing a pharmaceutical preparation comprising subjecting a composition of the invention to one or more steps of converting the target compound of the invention in the composition to a pharmaceutically active derivative selected from the group consisting of Berberine, Papaverine, Morphine, Sanguinarine, Noscapine, Neomorphine, hydrocodone, Codeine, Oxycodone, Oxymorphone, Dihydromorphine and buprenorphine; and mixing the derivative with one or more pharmaceutical grade additives and/or adjuvants. The target compound of the invention may be converted by chemical conversion, by in vitro enzymatic conversion or by in vivo enzymatic conversion or any combination of the said conversion methodology. In one embodiment the compound of the invention is thebaine and the thebaine is converted to a pharmaceutically active thebaine derivative selected from the group consisting of Morphine, neomorphine, hydrocodone, Codeine, Oxycodone, Oxymorphone, Dihydromorphine, etorphine and buprenorphine. In another embodiment the compound of the invention is (S)-norcoclaurine and the (S)-norcoclaurine is converted to a pharmaceutically active derivative selected from the group consisting of Berberine, Papaverine, Sanguinarine, and Noscapine.

Method of Use

The invention further provides a pharmaceutical preparation obtainable or obtained from the method of the invention converting the compound of the invention into a pharmaceutically active derivative. The pharmaceutical preparation may be used as a medicament to treat alleviate a disease or pathological conditions, particularly in a mammal. The pharmaceutical preparation may be used as an analgesic, an antimicrobial, an antitussive, an antiparasitic, an cytotoxic, an antipoisoning and/or an anticancer agent. In addition, the invention also provides a method for treating pain, infectious conditions, tussive conditions, parasitic conditions, cytotoxic conditions, opiate poisoning conditions and/or cancerous conditions in a mammal comprising administering a therapeutically effective amount of the pharmaceutical preparation of the invention to the mammal. The mammal is preferably a human, a livestock and/or pet animal.

Sequence Listings

The present application contains a Sequence Listing prepared in patent In submitted electronically in ST25 format which is hereby incorporated by reference in its entirety.

EXAMPLES

Materials and Methods
Materials

Chemicals used in the examples herein e.g. for buffers and substrates are commercial products of at least reagent grade.

Strains

S288C is a common strain of S. cerevisiae available eg. from American Type Culture Collection (ATCC #204508™).

The S. cerevisiae strain (BY4741) used throughout these examples can be derived from S288C using the methodology of Brachmann C B, et al.; Yeast 14(2):115-32; 1998 and/or Winston F, et al.; Yeast 11(1):53-5; 1995. BY4741 strains can also be obtained commercially from ATTC® or EUROSCARF.

Example 1—Analytical Procedures

Metabolites were separated and identified by reversed-phase UPLC-MS using an Agilent 1290 UPLC coupled to an Ultivo Triple Quadrupole using the following settings:

Mobile Phase A. 0.1% aqueous solution of formic acid;

Mobile Phase B: 0.1% solution of formic acid in Acetonitrile;

Column: Kinetex™ 1.7 µm XB-C18 100 Å, 2.1×100 mm from Phenomenex™.

The elution gradient shown in Table 1 was used with the UPLC conditions shown in Table 2. Table 3 shows the mass spectrometer settings and parameters used and table 4 shows the target compound, retention time, parent ion, transition ions (MRM) as well as dwell time, fragmentor voltage, and collision energy used.

TABLE 1

Gradient for UPLC

| Time (min) | % B |
|---|---|
| 0 | 2 |
| 0.30 | 2 |
| 3.00 | 25 |
| 3.40 | 100 |
| 3.90 | 100 |
| 4 | 2 |
| 5 | 2 |

TABLE 2

UPLC conditions

| Parameter | Setting |
|---|---|
| Injection volume | 2 µl |
| Column Temperature | 30° C. ± 4° C. |
| Injection method | Flow through needle |
| Flow | 0.4 mL/min |
| Auto sampler temperature | 10° C. ± 2° C. |
| Reconditioning wash | 2% Acetonitrile (in $H_2O$), 5 sec |
| Weak wash | 20% Methanol (in $H_2O$), 5 sec |
| Strong wash | 30% Acetonitrile, 30% Methanol, 30% 2-propanol, 10% $H_2O$, 10 sec |
| Seal wash | 20% 2-Propanol (in $H_2O$) |

TABLE 3

Mass spectrometer source and detector settings (Ultivo Triple Quadrupole)

| Source Parameter | Setting |
|---|---|
| Ion Source | Electrospray Positive Mode (ESI+) |
| Capillary Voltage | 3.5 kV |
| Nozzle Voltage | 500 V |
| Source Gas Temperature | 290° C. |
| Source Gas Flow | 12 L/min |
| Source Sheath Gas Temperature | 380° C. |
| Source Sheath Gas Flow | 12 L/min |
| Nebulizer | 30 psi |
| Mode | MS/MS |
| Collision | See Table 4 |

TABLE 4

Multiple reaction monitoring targets and conditions (ESI+)

| Target compound | Retention time (min) | Parent ion (m/z) | Daughter ion (m/z) | Dwell time (ms) | Fragmentor voltage (V) | Collision energy (V) |
|---|---|---|---|---|---|---|
| Dopamine | 0.7 | 154 | 137 | 200 | 110 | 5 |
| Norcoclaurine | 2.29 | 272 | 255 | 200 | 110 | 5 |

Example 2—Construction of a *Saccharomyces cerevisiae* Strain for Production of Dopamine and Norcoclaurine A BY4741 *S. cerevisiae* strain was modified to delete the native gene ARI1; YGL157W; SGD:S000003125 as disclosed in the *saccharomyces* genome database (SGD), by replacing the ORF encoding ARI1 with the KanMX dominant selection marker cassette (see Walker, M E et al.; FEMS Yeast Res. 2003 December; 4(3):339-47).

This strain was further modified to express an N-terminally truncated *Coptis japonica* Norcoclaurine Synthase (d19CjNCS—SEQ ID NO: 75). The truncation replaced the first 19 amino acids of SEQ ID NO: 75 with a methionine thereby removing a putative signal peptide. The gene was expressed using the well known *S. cerevisiae* PGK1 promoter, and the expression cassette was integrated in site XII-2 with the gene HIS3 as selection marker for growth on media lacking histidine (described by Mikkelsen, M D et al. (Metab. Eng. 14, Issue 2, 104-111 (2012)).

Using the *S. cerevisiae* gene integration and expression system developed by Mikkelsen, M D et al. (Metab. Eng. 14, Issue 2, 104-111 (2012)) (genes synthesized by Twist Bioscience, San Francisco, CA, USA, expression cassettes containing genes encoding the *Pseudomonas putida* DOPA decarboxylase (PpDODC—SEQ ID NO: 60), a *Beta vulgaris* CYP450 reductase (BvCPR1—SEQ ID NO: 76), a feed-back resistant *S. cerevisiae* ARO7 (ARO7fbr—SEQ ID NO: 77) and a gene encoding a CYP450 family 76 protein (SEQ ID NO: 2, 4, 6, 8, 10, 12, 14, 16, 18, 20, 22, 24, 26, 28. 30, 32, 34, 36, 38, 40, 42, 44, 46, 48, 50, 52, 54, 56 or 58) were integrated into the site XI-5 of the ARI1 deleted *S. cerevisiae* strain with Norcoclaurine Synthase expression described above. The twenty-nine CYP450s were tested separately for tyrosine hydroxylase activity in the strain background described. The genes were selected for testing based upon sequence homology to a double mutant to the CYP76AD1 from *Beta vulgaris* (CYP76AD1, W13L, F309L—SEQ ID NO: 58—also published in WO16049364) and the activities of the strains were compared to a strain containing the double mutant protein. Selection for transformants was done using the well known *Kluyveromyces lactis* LEU2 marker available e.g. from EUROSCARF and growth on media lacking leucine. Where all enzymes where expressed and active the recombinant *S. cerevisiae* strain produced norcoclaurine as the end product.

Example 3 Production of Norcoclaurine and Dopamine Using Different CYP76 Tyrosine Hydroxylases The recombinant *S. cerevisiae* transformants of example 2 were grown in triplicate in 96 deep-well plates in 500 µL liquid of the well known synthetic complete (SC) media available e.g. from Sigma Aldrich lacking histidine and leucine, for 3 days at 30° C. with shaking at 230 rpm in a Kuhner Climo-Shaker ISF1-X. Culture samples for LC-MS were prepared by extraction as follows: 96% ethanol and culture sample were mixed 1:1 and incubated on a heating block at 80° C. for 10 min. After heating, cells were pelleted in an Eppendorff tabletop centrifuge by centrifugation and the supernatant was then transferred to a new tube and diluted 1:5 in water.

As can be seen in table 5 (average of triplicate measurements), a number of tyrosine hydroxylases (CYP450 of family 76 (CYP76)) showed surprisingly good capabilities of producing L-dopa, dopamine and (S)-norcoclaurine when co-expressed with the DOPA decarboxylase (PpDODC—SEQ ID NO: 60) and Norcoclaurine Synthase (d19CjNCS—SEQ ID NO: 75) as described above. For several of the tested CYP76's production of L-dopa, dopamine and (S)-norcoclaurine was unexpectedly high compared to the modified CYP76AD1 disclosed by DeLoache, W. C. et al Nat. Chem. Biol., 11, 465-471 (2015), most notably by the spinach CYP76 SoCYP76ADr9. Other tested CYP450s are also more active than the modified CYP76AD1 as shown by the larger production of dopamine and/or norcoclaurine. Accordingly, it is contemplated that these CYP450s are tyrosine hydroxylases and not also cyclo-dopa synthases like the native BvCYP76AD1 from *B. vulgaris* described in WO16049364 A3.

TABLE 5

| Tyrosine Hydroxylase CYP76 | Sequence | Species | Norcoclaurine mg/l | Dopamine AUC |
|---|---|---|---|---|
| AnCYP76ADr17 | SEQ ID NO: 10 | *Abronia nealleyi* | 0.729 | 3991 |
| SoCYP76ADr9 | SEQ ID NO: 2 | *Spinacia oleracea* | 0.650 | 15010 |
| BvCYP76ADr10 | SEQ ID NO: 8 | *Beta vulgaris* | 0.647 | 5009 |
| BvCYP76ADr8 | SEQ ID NO: 12 | *Beta vulgaris* | 0.633 | 2897 |
| BvCYP76ADr7 | SEQ ID NO: 14 | *Beta vulgaris* | 0.517 | 2745 |
| BvCYP76ADr6 | SEQ ID NO: 16 | *Beta vulgaris* | 0.496 | 2535 |
| OfCYP76ADr12 | SEQ ID NO: 4 | *Opuntia ficus-indica* | 0.477 | 9549 |
| FlCYP76ADr11 | SEQ ID NO: 6 | *Froelichia latifolia* | 0.388 | 9301 |
| AoCYP76ADr16 | SEQ ID NO: 24 | *Acleisanthes obtuse* | 0.250 | 1080 |
| BvCYP76AD1 | SEQ ID NO: 58 | *Beta vulgaris* | 0.242 | 1109 |
| PdCYP76ADr21 | SEQ ID NO: 22 | *Phytolacca dioica* | 0.145 | 1113 |
| MmCYP76ADr18 | SEQ ID NO: 26 | *Mirabilis multiflora* | 0.142 | 816 |
| EvCYP76ADr20 | SEQ ID NO: 20 | *Ercilla volubilis* | 0.125 | 1236 |

TABLE 5-continued

| Tyrosine Hydroxylase CYP76 | Sequence | Species | Norcoclaurine mg/l | Dopamine AUC |
|---|---|---|---|---|
| PaCYP76ADr19 | SEQ ID NO: 32 | *Phytolacca americana* | 0.076 | 405 |
| CbCYP76ADr28 | SEQ ID NO: 18 | *Cleretum bellidiforme* | 0.075 | 2032 |
| AoCYP76ADr24 | SEQ ID NO: 28 | *Acleisanthes obtuse* | 0.075 | 739 |
| AnCYP76ADr27 | SEQ ID NO: 30 | *Abronia nealleyi* | 0.062 | 530 |
| CqCYP76ADr5 | SEQ ID NO: 34 | *Chenopodium quinoa* | 0.053 | 260 |
| CqCYP76ADr4 | SEQ ID NO: 38 | *Chenopodium quinoa* | 0.034 | 209 |
| MmCYP76ADr22 | SEQ ID NO: 36 | *Mirabilis multiflora* | 0.032 | 238 |
| AnCYP76ADr23 | SEQ ID NO: 42 | *Abronia nealleyi* | 0.008 | 139 |
| PaCYP76ADr14 | SEQ ID NO: 40 | *Phytolacca americana* | 0.008 | 157 |
| CqCYP76ADr13 | SEQ ID NO: 50 | *Chenopodium quinoa* | 0.000 | 54 |
| MjCYP76ADr26 | SEQ ID NO: 54 | *Mirabilis jalapa* | 0.000 | 12 |
| MmCYP76ADr25 | SEQ ID NO: 56 | *Mirabilis multiflora* | 0.000 | 10 |
| Neg K | — | — | 0.000 | 8 |
| SoCYP76ADr1 | SEQ ID NO: 48 | *Spinacia oleracea* | 0.000 | 71 |
| SoCYP76ADr15 | SEQ ID NO: 52 | *Spinacia oleracea* | 0.000 | 30 |
| SoCYP76ADr2 | SEQ ID NO: 44 | *Spinacia oleracea* | 0.000 | 111 |
| SoCYP76ADr3 | SEQ ID NO: 46 | *Spinacia oleracea* | 0.000 | 98 |

The invention claimed is:

1. A recombinant microbial host cell comprising an operative biosynthetic metabolic pathway capable of producing one or more target compounds selected from the group consisting of L-dopa, dopamine, (S)-Norcoclaurine, and derivatives thereof;
  wherein said pathway comprises one or more heterologous L-tyrosine hydroxylases (TyrH) capable of converting L-Tyrosine into L-dopa and capable of increasing the cell production of the one or more target compounds compared to a reference L-tyrosine hydroxylase having the sequence set forth in SEQ ID NO: 58, wherein the one or more heterologous TyrH is a polypeptide having at least 90% sequence identity to SEQ ID NO: 2.

2. The host cell of claim 1, wherein the operative biosynthetic metabolic pathway further comprises one or more enzymes of a benzylisoquinoline alkaloid (BIA) pathway.

3. The host cell of claim 1, wherein the one or more target compounds is a benzylisoquinoline alkaloid.

4. The host cell of claim 3, wherein the benzylisoquinoline alkaloid is selected from the group consisting of:
  a) (S)-Norcoclaurine;
  b) (S)-Norlaudanosoline;
  c) (S)-Coclaurine;
  d) (S)-3'-Hydroxy-coclaurine;
  e) (S)-N-Methylcoclaurine;
  f) (S)-3'-Hydroxy-N-Methylcoclaurine;
  g) (S)-Reticuline;
  h) (R)-Reticuline;
  i) Salutaridine;
  j) Salutaridinol; and
  k) Thebaine.

5. The host cell of claim 4, wherein the benzylisoquinoline alkaloid is Thebaine.

6. The host cell of claim 1, wherein the host cell is a yeast cell.

7. The host cell of claim 6, wherein the yeast cell is a S. cerevisiae strain modified by deletion, disruption or down-regulation of the native gene ARI1.

8. A cell culture, comprising the host cell of claim 1 and a fermentation liquid.

9. A method for producing at least one target compound selected from the group consisting of one or more of L-dopa, dopamine, (S)-Norcoclaurine, and derivatives thereof comprising:
  a) culturing the cell culture of claim 8 at conditions allowing the host cell to produce the at least one target compound; and
  b) optionally recovering and/or isolating the at least one target compound.

10. The method of claim 9, wherein at least one step of producing the at least one target compound is performed in vitro.

11. The method of claim 9, wherein the at least one target compound is a benzylisoquinoline alkaloid selected from the group consisting of:
  a) (S)-Norcoclaurine;
  b) (S)-Norlaudanosoline;
  c) (S)-Coclaurine;
  d) (S)-3'-Hydroxy-coclaurine;
  e) (S)-N-Methylcoclaurine;
  f) (S)-3'-Hydroxy-N-Methylcoclaurine;
  g) (S)-Reticuline;
  h) (R)-Reticuline;
  i) Salutaridine;
  j) Salutaridinol; and
  k) Thebaine.

12. A fermentation liquid comprising the cell culture of claim 8 and the at least one target compound selected from L-dopa, dopamine, (S)-Norcoclaurine, and derivatives thereof comprised in the cell culture of claim 8.

13. The fermentation liquid of claim 12, further comprising one or more compounds selected from:
  a) precursor or products of the operative biosynthetic metabolic pathway producing the at least one target compound;
  b) supplemental nutrients comprising salts; and
  wherein the concentration of the at least one target compound is at least 1 mg/l liquid.

14. A composition comprising the fermentation liquid of claim 12 and one or more agents, additives and/or excipients.

15. A method for preparing a pharmaceutical preparation comprising subjecting the composition of claim 14 to one or more steps of converting the target compound in the composition to a pharmaceutically active derivative selected from the group consisting of Berberine, Papaverine, Morphine, Sanguinarine, Noscapine, Neomorphine, hydrocodone, Codeine, Oxycodone, Oxymorphone, Dihydromorphine, and buprenorphine; and mixing the pharmaceutically active derivative with one or more pharmaceutical grade additives and/or adjuvants.

16. The method of claim 15, wherein the target compound is converted by chemical conversion, by in vitro enzymatic conversion or by in vivo enzymatic conversion or any combination of the said conversions.

17. The host cell of claim 2, wherein the one or more enzymes of the BIA pathway is selected from the group consisting of:
  a) 3-deoxy-D-arabino-2-heptulosonic acid 7-phosphate (DAHP) synthase;
  b) 5-enolpyruvylshikimate-3-phosphate (EPSP) synthase
  c) chorismate synthase;
  d) chorismate mutase, wherein the chorismate mutase has at least 70% sequence identity to SEQ ID NO: 77;
  e) prephenate dehydrogenase;
  f) aromatic aminotransferase;
  g) P450 reductase (CPR), wherein the CPR has at least 70% sequence identity to SEQ ID NO: 76;
  h) L-dopa decarboxylase (DODC), wherein the DODC has at least 70% sequence identity to SEQ ID NO: 60;
  i) Tyrosine decarboxylase (TYDC);
  j) hydroxyphenylpyruvate decarboxylase (HPPDC);

k) Norcoclaurin synthase (NCS), wherein the NCS has at least 70% sequence identity to SEQ ID NO: 61 or SEQ ID NO: 75;
l) 6-O-methyltransferase (6-OMT), wherein the 6-OMT has at least 70% sequence identity to SEQ ID NO: 62;
m) Coclaurine-N-methyltransferase (CNMT), wherein the CNMT has at least 70% sequence identity to SEQ ID NO: 63;
n) N-methylcoclaurine 3'-monooxygenase (NMCH), wherein the NMCH has at least 70% sequence identity to SEQ ID NO: 65;
o) 3'-hydroxy-N-methyl-(S)-coclaurine 4'-O-methyltransferase (4'-OMT), wherein the 4'-OMT has at least 70% sequence identity to SEQ ID NO: 66;
p) 1,2-dehydroreticuline synthase-1,2-dehydroreticuline reductase (DRS-DRR), wherein the DRS-DRR has at least 70% sequence identity to SEQ ID NO: 68;
q) salutaridine synthase (SAS), wherein the SAS has at least 70% sequence identity to SEQ ID NO: 70;
r) salutaridine reductase (SAR), wherein the SAR has at least 70% sequence identity to SEQ ID NO: 71;
s) salutaridinol 7-O-acetyltransferase (SAT), wherein the SAT has at least 70% sequence identity to SEQ ID NO: 73; and
t) Thebaine synthase (THS), wherein the THS has at least 80% sequence identity to SEQ ID NO: 79 or SEQ ID NO: 80.

* * * * *